United States Patent
Keusenkothen et al.

(10) Patent No.: US 9,505,680 B2
(45) Date of Patent: *Nov. 29, 2016

(54) METHOD AND APPARATUS FOR MANAGING THE CONVERSION OF HYDROCARBONS INTO OLEFINS

(75) Inventors: Paul F. Keusenkothen, Houston, TX (US); Frank Hershkowitz, Basking Ridge, NJ (US); Jason D. Davis, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 319 days.

This patent is subject to a terminal disclaimer.

(21) Appl. No.: 13/994,491

(22) PCT Filed: Dec. 20, 2011

(86) PCT No.: PCT/US2011/066186
§ 371 (c)(1),
(2), (4) Date: Sep. 18, 2013

(87) PCT Pub. No.: WO2012/099675
PCT Pub. Date: Jul. 26, 2012

(65) Prior Publication Data
US 2014/0163273 A1   Jun. 12, 2014

Related U.S. Application Data

(60) Provisional application No. 61/434,409, filed on Jan. 19, 2011, provisional application No. 61/434,411, filed on Jan. 19, 2011, provisional application No. 61/434,410, filed on Jan. 19, 2011, provisional
(Continued)

(30) Foreign Application Priority Data

Mar. 31, 2011   (EP) .................................... 11160754

(51) Int. Cl.
*C07C 5/05* (2006.01)
*C07C 4/04* (2006.01)

(52) U.S. Cl.
CPC .. *C07C 5/05* (2013.01); *C07C 4/04* (2013.01)

(58) Field of Classification Search
CPC ............ C07C 5/05; C07C 4/04; C07C 11/04; C07C 11/24; C07C 2/76; C07C 4/025
USPC ......................................................... 585/256
See application file for complete search history.

(56) References Cited

U.S. PATENT DOCUMENTS

| 1,134,677 A | 4/1915 | Heinemann |
| 1,860,624 A | 5/1932 | Sauerwein |

(Continued)

FOREIGN PATENT DOCUMENTS

| BE | 722895 | 10/1968 |
| DE | 875198 | 4/1953 |

(Continued)

OTHER PUBLICATIONS

Bullerwell, J.; Kenchenpur, A.; Whidden, T. K. "Stability of acetylene/methane and acetylene/hydrogen/methane gas mixtures at elevated temperatures and pressures", Fuel, 89, (Available online Jul. 2, 2009), pp. 254-256.*

(Continued)

*Primary Examiner* — Renee E Robinson
*Assistant Examiner* — Aaron Pierpont

(57) ABSTRACT

An apparatus and method are provided for processing hydrocarbon feeds. The method enhances the conversion of hydrocarbon feeds into ethylene. In particular, the present techniques expose feed containing hydrocarbons to high-severity operating conditions in a pyrolysis reactor and separate the reactor product from the reactor into a first product having hydrogen and a second product including ≥90 mole percent of the acetylene in the reactor product. Then, the second product is reacted with a catalyst in a converter to form ethylene.

11 Claims, 10 Drawing Sheets

Related U.S. Application Data application No. 61/434,417, filed on Jan. 19, 2011, provisional application No. 61/434,415, filed on Jan. 19, 2011, provisional application No. 61/434,413, filed on Jan. 19, 2011, provisional application No. 61/434,419, filed on Jan. 19, 2011, provisional application No. 61/481,999, filed on May 3, 2011, provisional application No. 61/500,854, filed on Jun. 24, 2011, provisional application No. 61/504,611, filed on Jul. 5, 2011.

(56) References Cited

U.S. PATENT DOCUMENTS

| | | |
|---|---|---|
| 2,319,679 A | 5/1943 | Hasche et al. |
| 2,678,339 A | 5/1954 | Harris |
| 2,692,819 A | 10/1954 | Hasche et al. |
| 3,024,094 A | 3/1962 | Coberly |
| 3,086,066 A * | 4/1963 | Breiter .................... C07C 7/177 502/202 |
| 3,093,697 A | 6/1963 | Kasbohm et al. |
| 3,156,733 A | 11/1964 | Happel et al. |
| 3,156,734 A * | 11/1964 | Happel .................... C07C 2/76 422/199 |
| 3,242,223 A | 3/1966 | Nonnenmacher et al. |
| 3,419,632 A | 12/1968 | Sogawa et al. |
| 3,617,495 A | 11/1971 | Zimmerman, Jr. et al. |
| 3,644,555 A | 2/1972 | Nagy et al. |
| 3,839,484 A | 10/1974 | Zimmerman, Jr et al. |
| 3,861,160 A * | 1/1975 | Walker .......................... 62/46.1 |
| 4,274,841 A | 6/1981 | Andresen et al. |
| 5,675,041 A | 10/1997 | Kiss et al. |
| 5,856,592 A | 1/1999 | Hagen |
| 6,049,011 A | 4/2000 | Kiss et al. |
| 6,121,503 A | 9/2000 | Janssen et al. |
| 6,177,600 B1 | 1/2001 | Netzer |
| 6,210,561 B1 | 4/2001 | Bradow et al. |
| 6,307,093 B1 | 10/2001 | Godwin et al. |
| 6,578,378 B2 | 6/2003 | Kaiser et al. |
| 7,045,670 B2 | 5/2006 | Johnson et al. |
| 7,115,789 B2 | 10/2006 | Kuechler et al. |
| 7,119,240 B2 | 10/2006 | Hall et al. |
| 7,138,047 B2 | 11/2006 | Stell et al. |
| 7,208,647 B2 | 4/2007 | Peterson et al. |
| 7,491,250 B2 | 2/2009 | Hershkowitz et al. |
| 7,815,873 B2 | 10/2010 | Sankaranarayanan et al. |
| 7,846,401 B2 | 12/2010 | Hershkowitz et al. |
| 7,943,808 B2 | 5/2011 | Hershkowitz et al. |
| 7,976,797 B2 | 7/2011 | Chun et al. |
| 8,158,837 B2 | 4/2012 | Mamadov et al. |
| 8,278,231 B2 | 10/2012 | Chun et al. |
| 8,440,070 B2 | 5/2013 | Keusenkothen |
| 8,512,663 B2 | 8/2013 | Chun et al. |
| 8,932,534 B2 | 1/2015 | Chun et al. |
| 2002/0000085 A1* | 1/2002 | Hall et al. .................... 60/39.02 |
| 2002/0098430 A1 | 7/2002 | Kawamura et al. |
| 2004/0002553 A1 | 1/2004 | Hall et al. |
| 2004/0192982 A1 | 9/2004 | Kuechler et al. |
| 2007/0090018 A1 | 4/2007 | Keusenkothen et al. |
| 2007/0090019 A1 | 4/2007 | Keusenkothen et al. |
| 2007/0090020 A1 | 4/2007 | Buchanan et al. |
| 2007/0191664 A1* | 8/2007 | Hershkowitz et al. ....... 585/539 |
| 2008/0142049 A1 | 6/2008 | Onishi et al. |
| 2008/0300438 A1 | 12/2008 | Keusenkothen et al. |
| 2009/0326288 A1* | 12/2009 | Mamadov et al. ........... 585/259 |
| 2010/0130803 A1 | 5/2010 | Keusenkothen et al. |
| 2010/0292523 A1 | 11/2010 | Hershkowitz et al. |

FOREIGN PATENT DOCUMENTS

| | | |
|---|---|---|
| DE | 1270537 | 6/1968 |
| DE | 2354217 | 5/1975 |
| EP | 1288182 | 3/2003 |
| EP | 1741691 | 1/2007 |
| EP | 2022772 | 2/2009 |
| GB | 795688 | 5/1958 |
| GB | 834419 | 5/1960 |
| GB | 846679 | 8/1960 |
| GB | 1007423 | 10/1965 |
| GB | 1090983 | 11/1967 |
| WO | 2005/097948 | 10/2005 |
| WO | 2011/008389 | 1/2011 |
| WO | 2012/099679 | 7/2012 |

OTHER PUBLICATIONS

Energy Fuels, 2007, 21(2), pp. 640-645.
Watt, L., "The Production of Acetlene from Methane by Partial Oxidation", Thesis University OG British Columbia, Sep. 1, 1951, pp. 1-50.
SRI Consulting Process Economics Program "Acetylene" Report 16 (1966) and 16A (1982).

\* cited by examiner

METHOD AND APPARATUS FOR MANAGING THE CONVERSION OF HYDROCARBONS INTO OLEFINS

CROSS-REFERENCE TO RELATED APPLICATIONS

This application claims priority from (i) U.S. Provisional Application Ser. No. 61/434,417, filed Jan. 19, 2011, EP Application No. 11160754.5, filed Mar. 31, 2011, and PCT/US2011/066186, filed Dec. 20, 2011; (ii) U.S. Provisional Application Ser. No. 61/434,409, filed Jan. 19, 2011, and PCT/US2011/066216, filed Dec. 20, 2011; (iii) U.S. Provisional Application Ser. No. 61/434,410, filed Jan. 19, 2011, and PCT/US2011/066202, filed Dec. 20, 2011; (iv) U.S. Provisional Application Ser. No. 61/434,411, filed Jan. 19, 2011, and PCT/US2011/066210, filed Dec. 20, 2011; (v) U.S. Provisional Application Ser. No. 61/434,413, filed Jan. 19, 2011, and PCT/US2011/066196, filed Dec. 20, 2011; (vi) U.S. Provisional Application Ser. No. 61/434,415, filed Jan. 19, 2011, and PCT/US2011/066152, filed Dec. 20, 2011; (vii) U.S. Provisional Application Ser. No. 61/434,419, filed Jan. 19, 2011, and PCT/US2011/066206, filed Dec. 20, 2011; (viii) U.S. Provisional Application Ser. No. 61/481,999, filed May 3, 2011, and PCT/US2011/066180, filed Dec. 20, 2011; (ix) U.S. Provisional Application Ser. No. 61/500,854, filed Jun. 24, 2011, and PCT/US2011/066174, filed Dec. 20, 2011; and (x) U.S. Provisional Application Ser. No. 61/504,611, filed Jul. 5, 2011, and PCT/US2011/066165, filed Dec. 20, 2011, the contents of each of which are incorporated by reference in their entirety.

FIELD

The present techniques relate to a method for managing the conversion of hydrocarbons into ethylene through a method that manages the hydrogen through an acetylene converter. The resulting conversion product may be further processed into the other products, such as polyolefins. Further, the present techniques relate to an apparatus used in the process, which enhances the conversion of hydrocarbons into conversion products, such as ethylene and other products, by managing the hydrogen and/or acetylene concentrations through the process.

BACKGROUND

The oil, gas and petrochemical industry desires to efficiently obtain hydrocarbons and process the hydrocarbons to produce desired products. Refining processes involve upgrading, converting or separating hydrocarbons (e.g., crude oil) into different streams, such as gases, light naphtha, heavy naphtha, kerosene, diesel, atmospheric gas oil, asphalt, petroleum coke and heavy hydrocarbons or fuel oil. Similarly, natural gas may be converted into industrial fuel gas, liquefied natural gas (LNG), ethane, propane, liquefied petroleum gas (LPG), and natural gas liquids (NGLs). The oil and gas processes are also often integrated with petrochemical systems to convert refinery streams into chemical products such as ethylene, propylene or polyolefins.

To convert hydrocarbon feeds into petrochemical or basic chemicals, chemical conversion processes may be utilized. These processes typically involve using thermal or catalytic reactors or furnaces to produce reactive hydrocarbon products, such as acetylene, ethylene or propylene in different proportions. As an example, steam cracking reactors are commonly utilized to convert the hydrocarbon feed into ethylene and acetylene, which may be further processed into various chemical products. The steam cracking reactors are utilized because they provide feed flexibility by being able to utilize gas (e.g., ethane) and liquid (e.g., naphtha) feeds. However, these feeds due to their high hydrogen content do not typically require hydrogen to manage reactor products from the process.

Historically, the oil and gas refineries utilize the higher value distillates from the hydrocarbon feed, which are typically fungible fuels, such as mogas, natural gas and diesel. As a result, the petrochemical refineries utilize the remaining fractions, such as ethane, propane, naphtha and virgin gas oil, in their processes. However, few chemical conversion processes are able to directly employ natural gas or the lower value refinery feeds, such as aromatic gas oils or fuel oils. As such, there is a need for a process that can produce ethylene and acetylene from different feeds, such as advantaged feeds (e.g., natural gas and/or aromatic gas oils, for example).

To process these feeds, high-severity conditions (e.g., more severe operating conditions, such as higher temperatures) are generally involved to produce products having a higher value than the feed. High-severity conditions enable methane cracking and aromatic ring cracking, which do not occur at appreciable rates at typical low-severity conditions (e.g., conventional steam cracking conditions). At high-severity conditions, the primary products of thermal chemical conversion processes are acetylene and ethylene along with hydrogen ($H_2$) and coke, which may vary in proportion depending on the temperatures, pressures, residence times and feed type utilized in the conversion process. Low-severity conditions may be still be used to convert higher hydrogen content refinery byproduct streams. At lower severity conditions, saturates may be converted to ethylene, propylene and butenes and alkyl aromatics may be converted to benzene, toluene and gasoline blend stock. Although high-severity operating conditions typically yield predominately acetylenes along with hydrogen, acetylene may be further hydrogenated to ethylene and ultimately polyethylene or other derivatives using conventional technology.

High-severity and low-severity conversion processes are typically based on different pyrolysis reactors, which may include pyrolysis alone or integrated with combustion chemistry. That is, the reactors may include pyrolysis chemistry (e.g., thermochemical decomposition of feed at elevated temperatures in the absence of oxygen) alone or in combination with combustion chemistry (i.e., exothermic chemical reactions between a fuel and an oxidant). These pyrolysis reactors can be divided into different types: partial combustion that burns part of the pyrolysis feed, indirect combustion that involves contacting the pyrolysis feed with combustion products, arc process that generate the electric arc or plasma to crack the pyrolysis feed, and thermal pyrolysis. Each of these pyrolysis types differs in the means of generating and transferring the heat for the pyrolysis, but can be broadly characterized as low-severity or high-severity.

Low-severity thermal processes, such as steam cracking or the Wulff process, are unable to significantly convert methane, which is a hydrogen rich hydrocarbon that yields excess hydrogen when cracked. Likewise, low-severity processes are unable to react severely hydrogen deficient feeds, such as aromatic rings, that require excess hydrogen or hydrogen rich feeds as a co-reactant. These processes feed higher hydrogen feeds that may crack at lower temperatures (e.g., ethane or naphtha), which favors high ethylene yields (e.g., acetylene yields are typically less than (<) 2 wt % of the reactor product).

Due to the low acetylene concentrations with low-severity processes and high ethylene concentrations, the reactor products may be managed without concern for acetylene autodecomposition. Typically, for low-severity operating conditions, the levels of acetylene are relatively low as compared to the ethylene concentrations produced, while high-severity operating conditions produce lower concentrations of ethylene and higher concentrations of acetylene. Accordingly, for high-severity processes, acetylene manufacture may involve special handling procedures if the acetylene concentrations above certain thresholds. That is, acetylene may be handled properly at low pressure and at low concentrations, but may be problematic at higher pressures and higher concentrations. Accordingly, special handling procedures and considerations are considered if operating with concentrated acetylene at elevated pressures to avoid autodecomposition or detonation.

Further, the acetylene concentrations are typically managed through different techniques. For instance, acetylene manufacturing plants absorb a raw acetylene stream into a polar liquid, such as dimethyl formamide (DMF), acetone, N-methyl pyrollidone (NMP) or methanol, to separate the acetylene from light gases. As an example, U.S. Pat. No. 7,208,647 describes using dilute absorbed acetylene by converting the liquid acetylene mixture to ethylene via an improved liquid phase hydrogenation process. Therefore, the reference avoids acetylene concentration at pressure, but has to remove substantially all the hydrogen from acetylene and then adds fresh hydrogen at the converter. Another process that operates at high severity is described in U.S. Patent App. Pub. No. 20090326288. In this process, the reference produces acetylene (up to 20 mol %) via methane pyrolysis and converts the reactor products (e.g., raw acetylene and hydrogen) to ethylene in a vapor phase wash coated hydrogenation reactor. The reference suggests that the selectivity to ethylene is maintained with a palladium titanate catalyst that has been additionally diluted with a solid dilutant and has been wash coated onto the walls of the reactor.

Although thermal pyrolysis reactors may be used to convert hydrocarbons into useful products, such as acetylene and ethylene, improved management of the hydrogen content is desired which can further enhance the processing of certain reactor products. Accordingly, it is desirable to provide a process that manages hydrogen in the conversion of hydrocarbon feeds into olefins in an enhanced manner.

SUMMARY

In one aspect, one or more embodiments of the present techniques provide a method for enhancing the conversion of feeds along with hydrogen into ethylene. In particular, the present techniques use a pyrolysis reactor that manages the hydrogen content to convert the hydrocarbons into ethylene and other petrochemical products in an enhanced manner. The pyrolysis processes may be managed by providing a converter diluent. Because of the concerns of high concentrations of acetylene at certain pressures, purification of the acetylene at an elevated pressure may be managed via converter dilution with an inert diluent in the vapor phase and/or liquid phase.

Further, in one or more embodiments, a method for processing hydrocarbons is described. The method of converting hydrocarbons comprising: exposing a pyrolysis feed under thermal pyrolysis high-severity operating conditions to produce a reactor product comprising hydrogen, ethylene, and X mole % acetylene per mole of reactor product; reacting at least a portion of the reactor product with a catalyst in a converter operated in at least partially in the vapor phase to form a conversion product comprising 0.0 mole % to Z mole % acetylene per mole of the conversion product, the portion of the reactor product comprising Y mole % of acetylene per mole of the portion of the reactor product and the portion of the reactor product having a hydrogen to acetylene molar ratio in the range of from 1.0 and 10.0; and wherein (i) X<90.0% of a first acetylene non-autodecomposition amount, (ii) Y<90.0% of a second acetylene non-autodecomposition amount, and (iii) Y>Z.

Further still, in one or more embodiments, a hydrogen separation unit, a mixing unit, and a converter are used for processing the reactor product. The hydrogen separation unit is configured to separate a reactor product into a hydrogen product and an acetylene rich product. The mixing unit is in fluid communication with the hydrogen separation unit and is configured to combine the acetylene rich product with a conversion recycle product to form a mixture, while the converter is in fluid communication with the mixing unit and is configured to react the mixture with a catalyst to form a conversion product comprising olefins. Further, a thermal pyrolysis reactor may be in fluid communication with the hydrogen separation unit and may be configured to expose a pyrolysis feed to a peak pyrolysis gas temperature ≥1540.0° C. within the thermal pyrolysis reactor to produce a reactor product comprising ethylene and acetylene. A polymerization unit may be in fluid communication with the converter and may be configured to convert at least a portion of the conversion product into polyethylene. Also, a splitter may be in fluid communication with the converter and the mixing unit and may be configured to separate the conversion recycle product from the conversion product.

The method may further comprise separating from the conversion product a converter recycle product comprising ethylene, and combining the converter recycle product with the retained portion of the reactor product upstream of the reacting; determining the X mole % acetylene per mole of reactor product; and adjusting the amount of converter recycle product mixed with the retained reactor product to maintain the mixture Y<90.0% of a second acetylene non-autodecomposition amount; determining a hydrogen content level for the retained reactor product; and adjusting the flow rate of at least one of the converter recycle product based on the X<90.0% of a first acetylene non-autodecomposition amount and the hydrogen content level in second product. Also, the method may include determining a hydrogen content level for the reactor product; and adjusting the amount of hydrogen separated from the reactor product based on this determination.

Further still, the method may include separating hydrogen from the reactor product upstream of the reacting, wherein the hydrogen is separated by means of a membrane (at a membrane inlet pressure in the range of 150 pounds per square inch gauge (psig) (1034 kiloPascal gauge (kPag)) to 250 psig (1724 kPag), by means of pressure swing adsorption (at a pressure swing adsorption inlet pressure in the range of 150 psig (1034 kPag) and 250 psig (1724 kPag)) and/or by means of liquid phase absorption and light gas desorbtion (performed at pressures in the range of 50 psig (345 kPag) to 250 psig (1724 kPag)).

Certain embodiments may include process control mechanisms. For instance, the apparatus may include an acetylene measurement device configured to measure the acetylene volume percent of the acetylene rich product; and a mixing flow rate unit configured to adjust the amount of converter recycle product mixed with the acetylene rich product to maintain the mixture at an acetylene non-autodecomposition amount. The embodiment may include a process control unit in communication with the mixing flow rate unit and the acetylene measurement device and configured to determine the acetylene volume percent of the acetylene rich product and provide an indication to the mixing flow rate unit to adjust the amount of converter recycle product mixed with the acetylene rich product. Further, an embodiment may include a hydrogen content measurement device configured to measure the hydrogen content of the reactor product; and a hydrogen separation control unit configured to adjust the amount of hydrogen product removed from the at least a portion of the reactor product in the hydrogen separation unit. A process control unit may be in communication with the hydrogen content measurement device and the hydrogen separation control unit and configured to determine the hydrogen content of the reactor product and provide an indication to the hydrogen separation control unit to adjust.

Figure 1A:
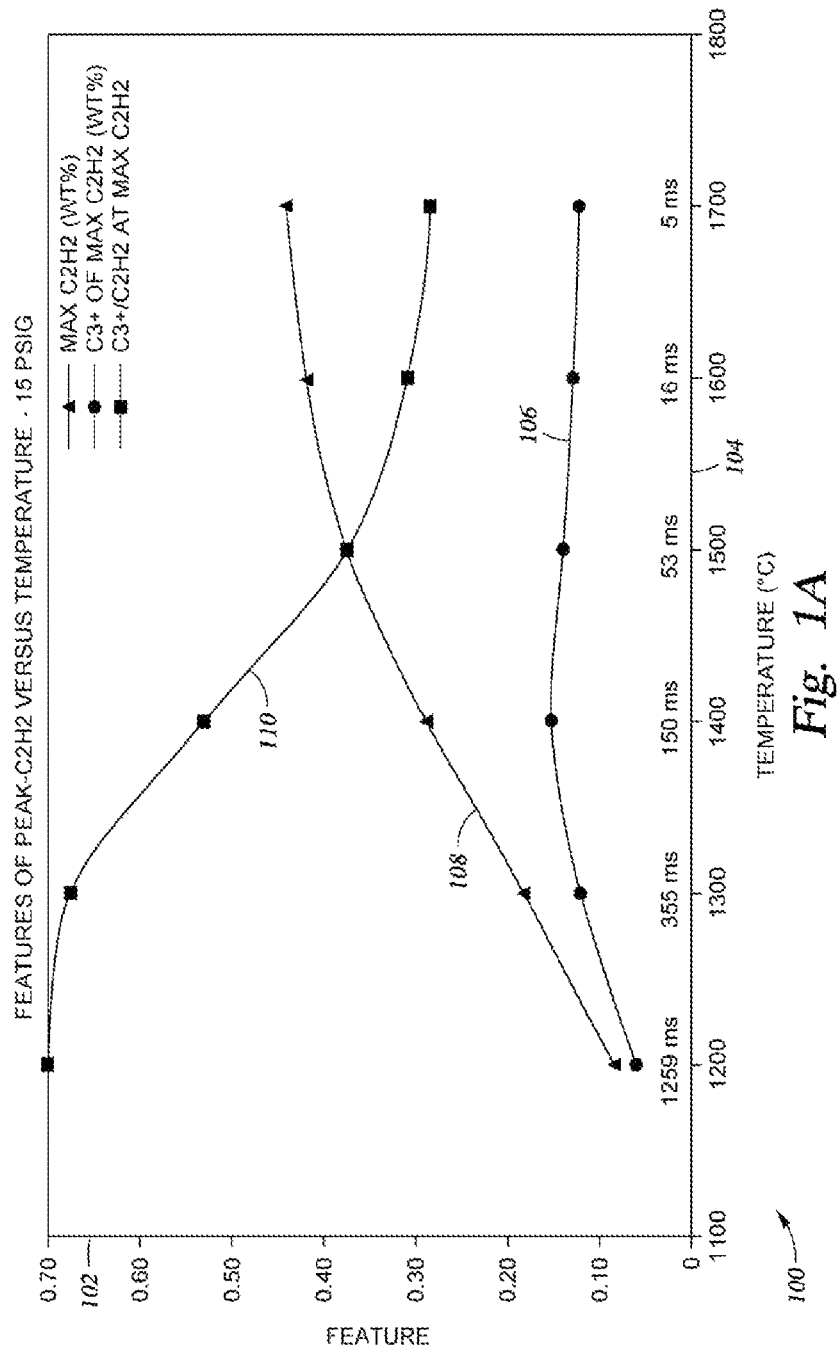
FIGS. 1A to 1F are diagrams of simulation results representing different ratios of reactor products produced at different temperatures and/or different pressures.

Although the invention is described in terms of a thermal pyrolysis process for producing acetylene and ethylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims.

DETAILED DESCRIPTION OF THE EMBODIMENTS

In contrast to conventional techniques, the present techniques provide an enhanced process for conversion of feed containing hydrocarbons to acetylene and ethylene and optionally polyolefins, while managing the composition of the streams (e.g., the amount of hydrogen in the feed or reactor product) through the process. As a specific example, the process initially manages the hydrogen content of a feed to a thermal pyrolysis reactor and processes the feed at high-severity operating conditions to produce a reactor product. Then, the process manages the composition (e.g., the acetylene content and/or the converter diluent content (e.g., hydrogen, ethylene or other suitable diluent) in at least a portion of the reactor product through the conversion process into a conversion product, which is discussed further below. Accordingly, the present techniques provide an enhancement in the processing of hydrocarbons.

The present techniques utilize a thermal or arc pyrolysis reactor configured to expose the pyrolysis feed to higher temperatures than conventional steam cracking or Wulff liquid feed pyrolysis. These higher temperatures are utilized to crack feeds that are normally unreactive or react to low value products (e.g., degraded products) at lower temperatures. As a specific example, at temperatures greater than or equal to ($\geq$) 1200.0° C., methane and aromatic components are partially cracked to yield unsaturated $C_2+$ compounds, typically acetylenes and ethylene. At temperatures $\geq$1400.0° C. or preferably $\geq$1540.0° C., aromatics and methane may be cracked at high conversion levels, with selectivity levels $\geq$50 wt % to light gas products. That is, at atmospheric pressure, higher temperature also provides selectivity to enhance the yield of unsaturated $C_2+$ compounds (e.g., yield of ethylene and acetylene). For example, the ethylene to acetylene weight ratio (E/A) may be less than or equal to ($\leq$) 0.10 or as low as 0.02 at atmospheric pressure.

To further enhance the process, higher pressure may be utilized to increase the E/A for certain operating conditions. That is, in addition to the higher temperatures, the feed may be exposed to pressures $\geq$4 psig (27 kPag), or $\geq$15 psig (103 kPag), or $\geq$36 psig (248 kPag), or $\geq$44 psig (303 kPag), or $\geq$150 psig (1034 kPag). Other aspects, such as the $C_{3+}$ to acetylene weight ratio or $C_{3+}$ to $C_2$ unsaturate ($C_2U$) weight ratio ($C_{3+}/C_2U$), may also be utilized to adjust the operating conditions, as discussed further below.

At any elevated temperature, hydrocarbon pyrolysis or hydropyrolysis produces acetylene at an intermediate residence time. As time continues, the hydrocarbons react further towards condensed species and eventually carbon (e.g., produce more coke). Thus, there is a maximum amount of acetylene, which is achieved at a specific residence time, and which is the optimum acetylene yield for a given temperature. The temperature and residence time of this maximum acetylene yield can be used to characterize thermal pyrolysis reactor performance at that temperature, in terms of the yield of $C_{3+}$ in relationship to the yield of acetylene. The yield of $C_{3+}$, as used herein, includes all $C_{3+}$ products of the pyrolysis feed, whether those products emerge from the reactor or remain within the reactor as coke. $C_{3+}$ includes, for example, products such as methyl acetylene, benzene and tar, and is specifically defined as including carbonaceous byproducts, such as coke.

To further explain the high-severity pyrolysis reactor and its associated products, various simulation results representing different ratios of reactor products produced at different temperatures and/or different pressures are provided. These simulations utilize certain feeds, such as methane, for simplicity, but the invention is not limited thereto. The maximum acetylene yield, the corresponding $C_{3+}$ yield and the acetylene to $C_{3+}$ weight ratio are described further in relation to temperature and residence time in FIGS. 1A and 1B and Table 1.

Figure 1B:
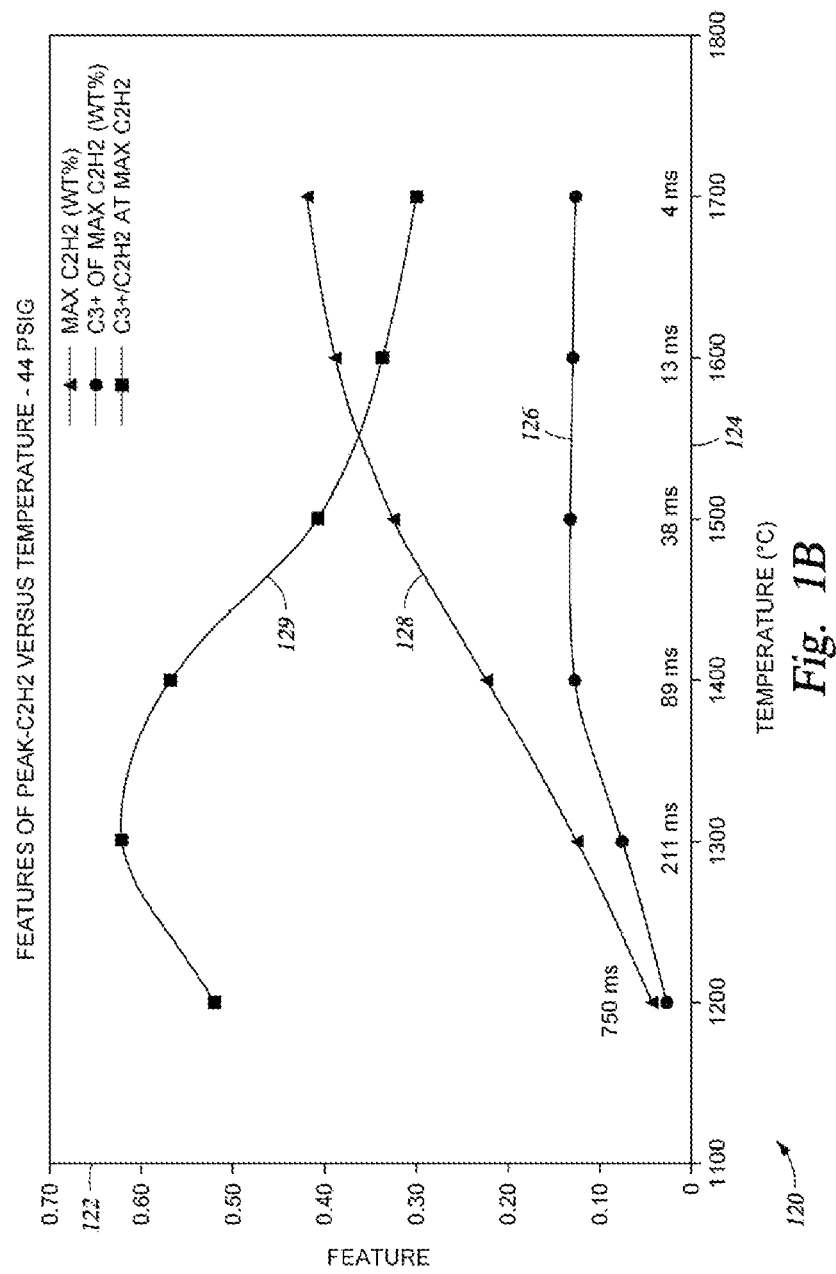

FIGS. 1A and 1B illustrate the simulation results for different weight ratios of reactor products produced at different temperatures for thermal pyrolysis of methane at an $H_2/CH_4$ molar ratio of 2. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen in a methane feed, and at 14.7 psig (101 kPag) pressure for diagram 100 and at 44 psig (303 kPag) pressure for diagram 120. All hydrocarbon products larger than $C_2$ are considered as $C_{3+}$ in this example and the product is the reaction product yield from the converted pyrolysis feed. In diagram 100, certain values for a maximum acetylene yield 108 in wt % of the product, and corresponding $C_{3+}$ yield 106 in weight percent (wt %) of the product and $C_{3+}$ to acetylene weight ratio 110 of the product are shown along the Y-axis 102 for various temperatures (in ° C.) along the X-axis 104. The $C_{3+}$ to acetylene weight ratio 110 has a peak between the temperatures of 1200° C. and 1400° C., which decreases at a slower rate as temperature increases from 1500° C. or 1540° C. Similarly, in diagram 120, certain values for a maximum acetylene yield 128 in wt % of the product, and corresponding $C_{3+}$ yield 126 in wt % of the product and $C_{3+}$ to acetylene weight ratio 129 of the product are shown along the Y-axis 122 for various temperatures (in ° C.) along the X-axis 124. The $C_{3+}$ to acetylene weight ratio 110 again has a peak within the range of 1300° C. to 1400° C., which decreases at a slower rate from 1500° C. or 1540° C. as the temperature increases. As such, operating conditions of the thermal pyrolysis reactor may be adjusted to enhance the acetylene yield for a pyrolysis feed.

This aspect is further described in Table 1, which includes simulation results for different ratios of reactor products produced at different temperatures for thermal pyrolysis of methane at an $H_2/CH_4$ molar ratio of 2. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen (as $H_2$) in a methane feed, and at 14.7 psig (101 kPag) reactor pressure. Table 1 lists the results, such as composition of the pyrolysis product (weight percent of total pyrolysis product), for operations at temperatures between 1200° C. and 2200° C.:

of the products. Residence time has a large impact on reactor volume (proportional to the reciprocal of residence time). As a result, a given unit of reactor may process more pyrolysis feed when the reactor temperature is high and residence time is low, which is shown in Table 1 as the $C_2H_2$/unit reactor volume. However, the very short residence times that achieve optimal acetylene yields at very high temperatures may place demands on certain reactor components that may exceed practicality. For example, where the pyrolysis feed is being flowed through the hot region of the pyrolysis reactor, the required gas velocity is roughly equal to the length of the hot region divided by the desired residence time. Gas velocities in flow channels and valve orifices are preferred to be less than the velocity of sound, which may result in reactor lengths that are not practical. In addition, because thermal pyrolysis involves the transfer of heat through a solid intermediary from a combustion step to a pyrolysis step, extremely short residence times may impose a heat transfer rate requirement (heat of reaction divided by reaction time) that may not be practical. As such, the design and operating conditions of the reactor may limit the maximum temperature that may be utilized to crack the given feed.

Even though maximum acetylene ($C_2H_2$) yield increases for methane with increasing temperature, the $C_{3+}$ yield is greatest for intermediate temperatures, such as 1400° C. Dividing $C_{3+}$ yield by acetylene yield gives a selectivity parameter ($C_+/C_2H_2$) that indicates how much $C_{3+}$, which is related to coke production, has to be managed per unit of acetylene produced. This selectivity parameter remains very high (e.g., ≥0.5) for temperatures below 1500° C., and drops into a lower section (e.g., ≤0.45 or ≤0.4) for temperatures at or above 1500° C.

For feeds containing high levels of aromatics or methane, temperatures below 1500° C. are not as effective for production of acetylene because of the high $C_{3+}$ yields, the low acetylene yields, and the relatively long residence times (e.g., large reactor volumes) needed for processing. Con-

TABLE 1

| | Temperature (° C.) | | | | | | | | |
|---|---|---|---|---|---|---|---|---|---|
| | 1200 | 1300 | 1400 | 1500 | 1540 | 1600 | 1650 | 1700 | 2200 |
| Max $C_2H_2$ (wt % of product) | 8.6% | 18.1% | 28.8% | 37.5% | 39.6% | 41.8% | 43.0% | 44.0% | 49.4% |
| Time of max $C_2H_2$ (sec) | 1.259 | 0.355 | 0.150 | 0.053 | 0.035 | 0.016 | 0.009 | 0.005 | 0.00006 |
| $C_{3+}$ (wt % of product) | 6.0% | 12.2% | 15.3% | 14.0% | 13.7% | 12.9% | 12.6% | 12.3% | 12.9% |
| $C_{3+}/C_2H_2$ | 0.699 | 0.673 | 0.530 | 0.372 | 0.346 | 0.308 | 0.293 | 0.281 | 0.261 |
| $C_2H_2$/unit reactor volume (relative units) | 0.068 | 0.510 | 1.928 | 7.066 | 11.31 | 26.38 | 47.8 | 92.98 | 8233 |
| $CH_4$ conversion | 29.9% | 53.4% | 73.3% | 83.1% | 84.6% | 86.9% | 88.8% | 88.7% | 96.9% |
| $H_2$ (wt % of product) | 24.2% | 27.9% | 31.2% | 32.9% | 33.2% | 33.6% | 34.0% | 33.9% | 34.8% |
| Surplus $H_2$ (wt % of prod.) | 3.5% | 6.5% | 8.9% | 10.0% | 10.1% | 10.3% | 10.6% | 10.4% | 11.0% |

As shown in this table, the maximum acetylene yield increases rapidly with temperature until 1500° C. Above this temperature, the maximum acetylene yield increases at a slower rate. Further, the residence time required to achieve this conversion decreases with increasing temperature. For instance, at 1200° C., residence times over 1 second are needed, and acetylene comprises only about 8.6 wt % of the products, while at 1700° C., residence times of about 5 milliseconds are needed and acetylene comprises 44.0 wt % versely, considering the broad range of temperature cited for methane pyrolysis, there is an advantage to operating at temperatures above 1500° C., in terms of $C_2U$ yield and $C_2$ selectivity.

In addition, as shown in Table 1, pyrolysis of hydrogen-rich feed components of the pyrolysis feed, such as methane, result in substantial yield of hydrogen ($H_2$) gas. While the feed is composed of 20 wt % $H_2$ gas, the reactor product is composed on 24 wt % to 35 wt % $H_2$ gas. Surplus hydrogen may be calculated as the amount of $H_2$ remaining after conversion to some preferred product. In Table 1, surplus $H_2$ is calculated after subtracting the stoichiometric amount of $H_2$ utilized to convert the acetylene product to ethylene. For temperatures above about 1500° C., surplus $H_2$ remains roughly constant at about 10 wt % of the reactor product. Thus, the pyrolysis of hydrogen-rich hydrocarbon components of the pyrolysis feeds results in surplus $H_2$ that is available for use in the hydrotreating and pyrolysis of hydrogen-deficient feeds or for other processes.

The high severity pyrolysis is also substantially impacted by the ratio of hydrogen ($H_2$) gas to feed hydrocarbon carbon (C), as shown in Tables 2 and 3, below. In the example of Table 2, the diluent includes only hydrogen, while in the example of Table 3, the hydrocarbon fraction is maintained at a constant 20 mol % and diluent includes a nitrogen $N_2$ concentration in addition to the a hydrogen ($H_2$) concentration. The pyrolysis of this example is for conversion of methane in an isothermal reactor at 1550° C. and at 14.7 psig (101 kPag). Residence times are selected to give 70 wt % conversion of the methane to products. All products larger than $C_2$ are considered as $C_{3+}$ in this example. Further, Table 2 lists the results, such as composition of the pyrolysis product (weight percent of total pyrolysis product) for operations at $H_2/C$ levels between 0 and 5, while Table 3 lists the results for operations at $H_2/C$ levels between 0 and 4.

TABLE 2

| $H_2/CH_4$ | 0 | 1 | 2 | 3 | 4 | 5 |
|---|---|---|---|---|---|---|
| wt % $H_2$ gas in Feed | 0.0% | 11.2% | 20.1% | 27.4% | 33.5% | 38.6% |
| wt % $N_2$ gas in Feed | 0.0% | 0.0% | 0.0% | 0.0% | 0.0% | 0.0% |
| Wt % H in total feed | 25% | 33% | 40% | 46% | 50% | 54% |
| atomic H/C in total feed | 4.0 | 6.0 | 8.0 | 10.0 | 12.0 | 14.1 |
| Time, sec | 0.004 | 0.007 | 0.011 | 0.014 | 0.018 | 0.021 |
| Conversion: | 70.0% | 70.0% | 70.0% | 70.0% | 70.0% | 70.0% |
| $C_2U$ (wt % of product) | 28.2% | 34.7% | 36.0% | 35.1% | 33.4% | 31.6% |
| $C_{3+}$ (wt % of product) | 28.2% | 15.6% | 9.3% | 6.1% | 4.4% | 3.3% |
| Hydrogen ($H_2$), wt %: | 13.5% | 23.1% | 30.7% | 37.0% | 42.2% | 46.7% |
| $C_{3+}/C_2U$ | 1.000 | 0.449 | 0.259 | 0.175 | 0.131 | 0.104 |
| E/A Ratio | 0.058 | 0.049 | 0.044 | 0.046 | 0.047 | 0.048 |
| $C_2-$ Gas MW: | 7.589 | 5.938 | 4.976 | 4.461 | 4.080 | 3.791 |
| relative $C_2$ productivity: | 509 | 280 | 168 | 111 | 78 | 57 |

TABLE 3

| | $H_2/CH_4$ | | | | |
|---|---|---|---|---|---|
| | 0 | 1 | 2 | 3 | 4 |
| wt % $H_2$ gas in Feed | 0.0% | 2.0% | 5.3% | 12.1% | 33.5% |
| wt % $N_2$ gas in Feed | 87.5% | 82.3% | 73.6% | 55.9% | 0.0% |
| wt % H in total feed | 3% | 6% | 11% | 20% | 50% |
| atomic H/C in total feed | 4.0 | 6.0 | 8.0 | 10.0 | 12.0 |
| Time, sec | 0.005 | 0.008 | 0.011 | 0.014 | 0.018 |
| Conversion: | 70.0% | 70.0% | 70.0% | 70.0% | 70.0% |
| $C_2U$ (wt % of product) | 3.8% | 6.2% | 9.5% | 15.5% | 33.4% |
| $C_{3+}$ (wt % of product) | 3.2% | 2.6% | 2.4% | 2.7% | 4.4% |
| Hydrogen ($H_2$), wt %: | 1.7% | 4.1% | 8.1% | 16.3% | 42.2% |
| $C_{3+}/C_2U$ | 0.840 | 0.423 | 0.253 | 0.174 | 0.131 |
| E/A Ratio | 0.041 | 0.030 | 0.032 | 0.040 | 0.047 |
| $C_2-$ Gas MW: | 22.415 | 17.738 | 13.148 | 8.628 | 4.080 |
| relative $C_2$ productivity: | 164 | 133 | 111 | 93 | 78 |

As shown in Table 2, high-severity pyrolysis preferentially uses a hydrogen diluent to improve $C_2U$ products. In Tables 2 and 3, the molar $H_2/CH_4$ ratio is increased from left to right, and corresponding levels for the total feed of weight percent $H_2$ gas, of atomic H/C ratio, and of total atomic H are indicated. In Table 2, in the absence of components other than $H_2$ and hydrocarbon, $C_{3+}$ and $C_{3+}/C_2U$ levels decrease substantially with increasing feed H/C, and feed H/C levels ≥5 may be preferred to provide $C_{3+}/C_2U$ levels below 0.5. High hydrogen diluent levels have a deleterious impact on reactor productivity because (i) the dilution reduces kinetic rates resulting in longer residence times (larger reactors) to achieve the same productivity, and (ii) because $H_2$ dilution reduces the amount of hydrocarbon (and hence hydrocarbon products) that are carried in each volume of gas. These effects are reflected in the relative $C_2$ productivity entry in Table 2, which shows in relative terms the impact of hydrogen dilution on amount of $C_2$ hydrocarbons that are produced in a unit of reactor volume. High hydrogen dilution may also result in debits in process equipment outside of the pyrolysis reactor due to the larger volumes of gases that have to be managed per unit of pyrolysis product produced. Thus, there is an optimum amount of hydrogen diluent at moderate levels between 0 and 5. Accordingly, the present techniques achieve a level of $C_{3+}/C_2U$ at low $H_2/C$ molar ratio and by means of high temperature pyrolysis, while other techniques require operating at high levels of $H_2/C$, which is less economical.

In Table 3, similar results are observed for feeds with substantial dilution by nitrogen (N2) gas. Remarkably, the reactor performance features, such as $C_+/C_2U$ levels are sensitive to the overall feed H/C ratio, and are not sensitive to the level of nitrogen gas dilution. For example, at an H/C ratio of 8, the $N_2$-diluted feed pyrolyzes to a $C_+/C_2U$ level of 0.253, and the undiluted to a level of 0.259. Thus, the stoichiometric parameter that controls the selectivity of thermal hydropyrolysis systems is the total atomic H/C ratio in the feed.

As shown in Table 4 below, conditions and yields for the pyrolysis of hydrogen deficient feeds may be different than those for the pyrolysis of hydrogen rich feeds shown in Table 1. A hydrogen deficient feed, in this example toluene having 8.7 wt % hydrogen content, is pyrolyzed at 1445° C., 4 psig (28 kPag) pressure, for a residence time of 0.08 seconds with a hydrogen diluent at a level of 28 moles $H_2$ gas per mole of hydrocarbon carbon. In this toluene conversion example, a high $H_2/C$ molar ratio is employed to compensate for a low pyrolysis temperature (1445° C.), while still achieving acceptable $C_{3+}/C_2U$ performance, thus illustrating features of toluene cracking. As indicated above, a more preferred operation is to pyrolyze the toluene at higher temperature and lower $H_2/C$ molar ratio.

TABLE 4

| Pyrolysis of Toluene (8.7 wt % H) | | Products: wt % of toluene feed | | Product Ratio | wt/wt |
|---|---|---|---|---|---|
| Pressure (psig) | 4 | Methane | 26% | $C_{3+}/C_2H_2$ | 0.351 |
| Temp (C.) | 1445 | Ethylene | 12% | $C_{3+}/C_2U$ | 0.283 |
| Residence time, ms | 80 | Acetylene | 49% | E/A | 0.238 |
| $H_2/C$ | 28 | $C_{3+}$ | 17% | | |
| | | $H_2$ | -5% | | |

As shown in Table 4, the pyrolysis results in a high conversion to acetylene (49 wt %) and ethylene (12 wt %), but also yields 17 wt % $C_{3+}$ materials (mostly coke and tar).

In contrast to the pyrolysis of hydrogen rich feed (Table 1), the hydropyrolysis of hydrogen deficient feed results in a consumption of hydrogen (from the $H_2$ diluent), and the production of methane (26 wt % of feed toluene) as a product. Thus, for the cracking of a hydrocarbon feed below a hydrocarbon hydrogen target level, the process involves the addition of hydrogen ($H_2$) or a hydrogen ($H_2$) rich feed or a hydrogen rich hydrocarbon feed to provide the $C_2U$ yields noted above by increasing the hydrogen content of the hydrocarbon to be above a hydrocarbon hydrogen target level and to bring the total ($H_2$ and hydrocarbon) hydrogen to carbon ratio above a total atomic hydrogen to carbon ratio target level. The hydrocarbon hydrogen target level may be a hydrogen content above 14 wt % and below 25 wt % in the hydrocarbons of the pyrolysis feed, while the total atomic hydrogen to carbon ratio target level may be a ratio between 3 and 15 in the pyrolysis feed, as described further below. Otherwise, the hydrocarbon feed converts to $C_{3+}$, not $C_2U$. Accordingly, it is advantageous to recycle the excess hydrogen ($H_2$) and methane gas that is produced from pyrolysis of hydrogen deficient feeds to be combined into the pyrolysis feed. Further, it is advantageous to recycle the methane gas that is produced in the pyrolysis of a hydrogen deficient feed to be combined with the hydrogen-rich hydrocarbon feed.

While the high-severity temperatures may be preferred if the objective of the process is to produce acetylene, variations in pressure along with the high-severity temperatures may enhance the distribution of $C_2$ compounds (e.g., yield of ethane, ethylene and acetylene) and the distribution of other light hydrocarbons (e.g., propylene, propyne, etc.). Accordingly, these pressure variations may be utilized if ethylene and/or other olefins are the preferred product. As an example, steam cracking typically utilizes lower temperature to convert ethane to ethylene and trace levels of acetylene. At atmospheric pressure, lower temperatures result in higher ethylene to acetylene (E/A) weight ratios. However, lower temperatures also provide poor conversions for methane and aromatics, which as noted above, is inefficient. At high-severity conditions (e.g., temperatures ≥1400° C. or preferably ≥1540° C., for example) aromatics and methane may be cracked at high conversion levels, with selectivity levels ≥50 wt % to light gas products. Also shown in Table 1, at temperatures ≥1400° C., selectivity levels ≥50 wt % to light gas products are achievable. For example, at 1540° C., products of methane make up 67.8 wt % of the pyrolysis product, including $H_2$, $C_2$ hydrocarbons, and $C_{3+}$.

Thus, the selectivity to $C_{3+}$ is 20 wt % (13.7 wt %/67.8 wt %), and the selectivity to lighter gas products is 80 wt %. Further, by varying the pressure from atmospheric to elevated pressures (e.g., up to 300 psig (2068 kPag)), ethylene to acetylene (E/A) weight ratios ≥0.1, ≥0.2, ≥0.4 or even ≥0.5 may be achieved. The variations of pressure at high-severity operating conditions are described below in Tables 5 and 6 and FIGS. 1C to 1F.

Table 5 includes simulation results for different ratios of reactor products produced at different pressures for different temperatures from a methane feed. Pyrolysis, in this example, is carried out under isothermal conditions at 1500° C. and at 1650° C., with 2:1 molar diluent of hydrogen in a methane feed, and at 15 psig (103 kPag) reactor pressure to 162 psig (1117 kPag) reactor pressure. All products larger than $C_2$ are considered as $C_{3+}$ in this example and the product is the reaction product yield from the converted pyrolysis feed.

TABLE 5

| 70% Isothermal Conversion Data | | | | | | | | | | Product Ratios | |
|---|---|---|---|---|---|---|---|---|---|---|---|
| Temp | P | time | | Products (weight percent) | | | | | | $C_{3+}/$ | |
| (° C.) | (psig) | (sec) | Conv. | $H_2$ | $CH_4$ | $C_2H_2$ | $C_2H_4$ | $C_{3+}$ | $C_2U$ | $C_2U$ | E/A |
| 1500 | 15 | 0.025 | 72% | 31.1 | 22.0 | 34.2 | 2.0 | 10.7 | 36.0 | 0.30 | 0.06 |
| 1500 | 36 | 0.025 | 73% | 31.1 | 21.7 | 32.7 | 3.1 | 11.3 | 36.0 | 0.32 | 0.10 |
| 1500 | 44 | 0.025 | 72% | 31.0 | 22.1 | 31.9 | 3.5 | 11.5 | 35.0 | 0.33 | 0.11 |
| 1500 | 59 | 0.025 | 71% | 30.7 | 23.3 | 30.3 | 4.1 | 11.6 | 34.0 | 0.34 | 0.14 |
| 1500 | 74 | 0.025 | 69% | 30.4 | 24.7 | 28.6 | 4.6 | 11.7 | 33.0 | 0.35 | 0.16 |
| 1500 | 103 | 0.025 | 65% | 29.7 | 27.9 | 25.4 | 5.4 | 11.5 | 31.0 | 0.37 | 0.21 |
| 1500 | 162 | 0.025 | 57% | 28.4 | 34.3 | 20.3 | 6.3 | 10.8 | 27.0 | 0.41 | 0.31 |
| 1650 | 15 | 0.0025 | 68% | 30.4 | 25.4 | 35.0 | 1.0 | 8.2 | 36.0 | 0.23 | 0.03 |
| 1650 | 36 | 0.0025 | 71% | 30.8 | 23.6 | 35.6 | 1.5 | 8.5 | 37.0 | 0.23 | 0.04 |
| 1650 | 44 | 0.0025 | 71% | 30.8 | 23.3 | 35.6 | 1.7 | 8.6 | 37.0 | 0.23 | 0.05 |
| 1650 | 59 | 0.0025 | 71% | 30.9 | 22.9 | 35.4 | 2.0 | 8.7 | 37.0 | 0.23 | 0.06 |
| 1650 | 74 | 0.0025 | 71% | 30.9 | 22.8 | 35.2 | 2.3 | 8.8 | 37.0 | 0.24 | 0.07 |
| 1650 | 103 | 0.0025 | 71% | 30.8 | 22.9 | 34.4 | 3.0 | 8.9 | 37.0 | 0.24 | 0.09 |
| 1650 | 162 | 0.0025 | 70% | 30.5 | 24.0 | 32.5 | 4.1 | 9.0 | 37.0 | 0.25 | 0.13 |

As shown in Table 5, as pressure increases from 15 psig (103 kPag) to 162 psig (1117 kPag), $C_2U$ yields in wt % of the product are roughly constant at about 33 wt % (+/−10 wt %) for 25 millisecond (ms) residence time at 1500° C. However, the E/A weight ratios improve over this increase in pressure. At 1650° C., the $C_2U$ yields in wt % of the product are again roughly constant at about 37 wt % (+/−10 wt %) for 2.5 ms, while the E/A weight ratio increases fourfold. Accordingly, the higher pressures tend to lead to higher E/A weight ratios. Further, the $C_{3+}$ yields in wt % of the product at these different temperatures and pressures also remain relatively constant at 12% for 1500° C. and 9% for 1650° C. As a result, the $C_{3+}$ to $C_2U$ weight ratio ($C_+/C_2U$) increases at slow rate with pressure at the lower temperature, while the higher temperatures provide a roughly constant $C_{3+}$ to $C_2$ unsaturate weight ratio.

From this table, the yield of $C_2U$ (e.g., acetylene and ethylene) may be optimized for certain operating conditions. That is, a specific pressure, temperature and residence time may be utilized to optimize the distribution of $C_2U$ yield. These operating conditions may be characterized by the $C_{3+}$ to $C_2U$ weight ratio along with an E/A weight ratio, which may be further explained in view of the FIGS. 1C and 1D.

Figure 1C:
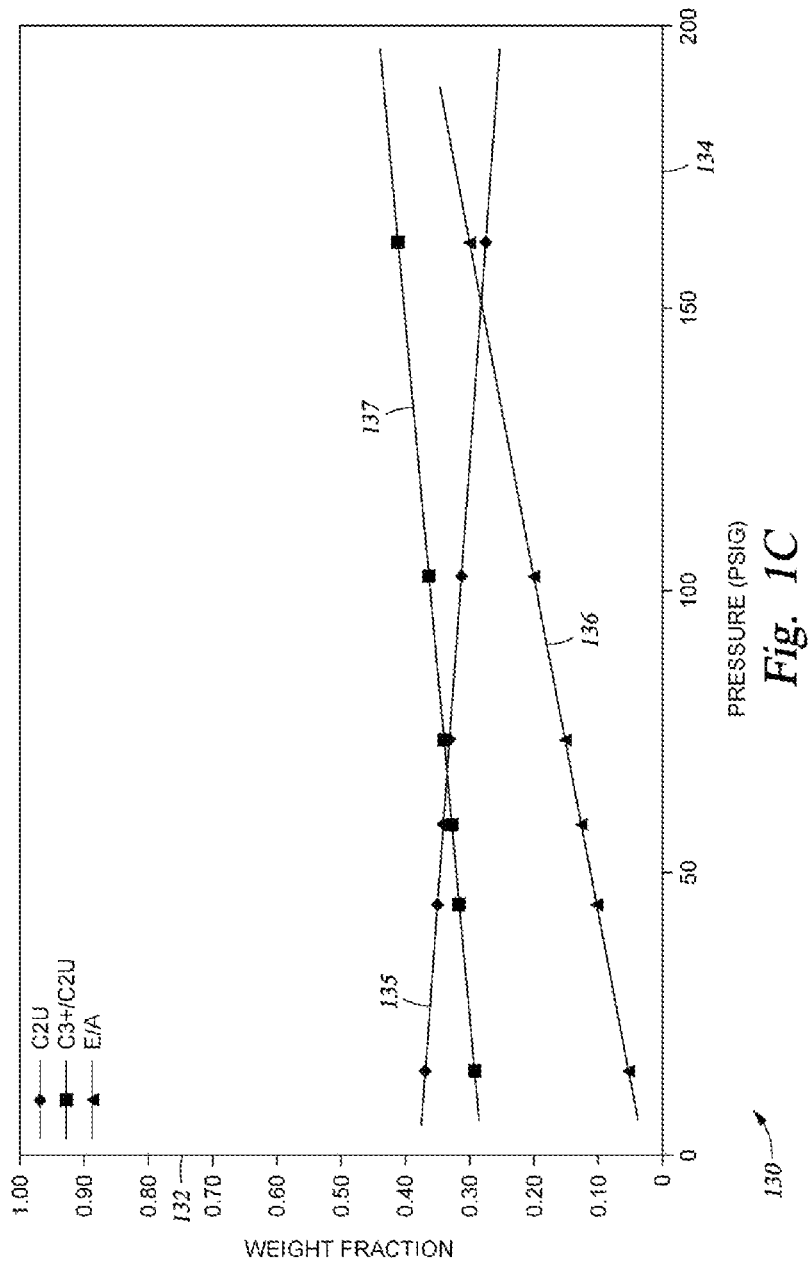
Figure 1D:
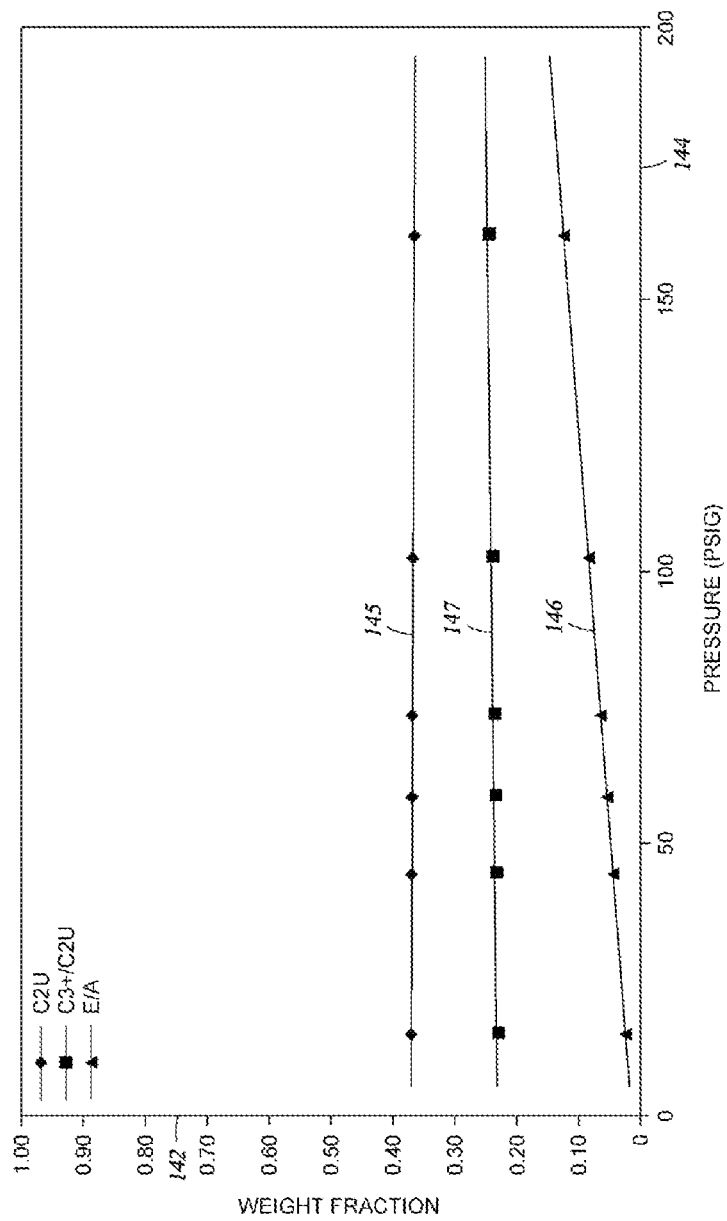

FIGS. 1C and 1D illustrate the simulation results for different ratios of reactor products produced at different pressures for certain temperatures from methane. The results of operating at the various pressures are provided for comparison of the product yields achievable at the residence times associated with the $C_2U$ yield and an E/A weight ratio for that pressure. Pyrolysis, in this example, is carried out under isothermal conditions, with 2:1 molar diluent of hydrogen in a methane feed, and at 1500° C. for diagram 130 and at 1650° C. for diagram 140. All products larger than $C_2$ are considered as $C_{3+}$ in this example and the product is the reaction product yield from the converted pyrolysis feed. In diagram 130, certain values for a $C_2U$ yield 135 in wt % of the product, ethylene to acetylene weight ratio 136, and $C_{3+}$ to $C_2U$ weight ratio 137 are shown in weight fraction (or weight ratio) along the Y-axis 132 for various pressures (in psig) along the X-axis 134. The ethylene to acetylene weight ratio 136 and $C_{3+}$ to $C_2U$ weight ratio 137 increases with increasing pressure, while the $C_2U$ yield 135 decreases slightly with increasing pressure. Similarly, in diagram 140, certain values for a $C_2U$ yield 145 in wt % of the product, ethylene to acetylene weight ratio 146, and $C_{3+}$ to $C_2U$ weight ratio 147 are shown in weight fraction (or weight ratio) along the Y-axis 142 for various pressures (in psig) along the X-axis 144. The ethylene to acetylene weight ratio 146 increases with increasing pressure, while the $C_2U$ yield 145 and $C_{3+}$ to $C_2U$ weight ratio 147 are relatively constant with increasing pressure. As such, operating conditions of the thermal pyrolysis reactor may be adjusted to enhance the acetylene yield for a given feed.

Further, as it may be appreciated, different types of thermal pyrolysis reactors may have different heat profiles. That is, some embodiments of thermal pyrolysis reactors may operate in an isothermal manner with the heat profile being relatively constant, as noted above. However, other thermal pyrolysis reactors may have a heat profile that is similar to a Gaussian curve. For example, a regenerative reactor may be characterized by an initial and final temperature of 300° C. and a peak pyrolysis gas temperature of 1700° C. for a residence time of 35 ms (≤10 ms at temperature ≥1000° C.), the pressure effect on selectivity is even more dramatic as shown in Table 5.

The variations of pressure at high-severity operating conditions for a regenerative reactor are described below in Table 6 and FIGS. 1E and 1F. Table 6 includes simulation results for different weight ratios of reactor products produced at different pressures for different temperatures from a methane feed. Pyrolysis, in this example, is carried out under regenerative conditions resulting in a Gaussian-like temperature profile with inlet and outlet around 300° C. and with peak temperature of 1704° C. in one set of simulations and of 1783° C. in the other. About 25% of the residence time of the regenerative pyrolysis profile is at temperature above 1200° C. The pyrolysis of this example is carried out with 2:1 molar diluent of hydrogen in a methane feed, and at various reactor pressures between 4 psig (28 kPag) and 162 psig (1117 kPag). All products larger than $C_2$ are considered as $C_{3+}$ in this example and the product is the reaction product yield from the converted pyrolysis feed.

TABLE 6

| 70% Regenerative Conversion Data | | | | | | | | | Product Ratios | | |
|---|---|---|---|---|---|---|---|---|---|---|---|
| Peak Temp | Pres. | time | | Products (weight percent) | | | | | | $C_{3+}/$ | |
| (° C.) | (psig) | (sec) | Conv. | $H_2$ | $CH_4$ | $C_2H_2$ | $C_2H_4$ | $C_{3+}$ | $C_2U$ | $C_2U$ | E/A |
| 1704 | 3 | 0.034 | 70% | 30.4 | 24.3 | 34.3 | 3.0 | 7.9 | 37.3 | 0.21 | 0.09 |
| 1704 | 15 | 0.034 | 72% | 30.7 | 22.2 | 33.6 | 5.0 | 8.4 | 38.6 | 0.22 | 0.15 |
| 1704 | 29 | 0.034 | 74% | 30.7 | 21.2 | 31.6 | 7.4 | 8.8 | 39.0 | 0.23 | 0.24 |
| 1704 | 36 | 0.034 | 74% | 30.6 | 21.0 | 30.5 | 8.5 | 8.9 | 39.0 | 0.23 | 0.28 |
| 1704 | 59 | 0.034 | 74% | 30.3 | 21.1 | 26.8 | 11.6 | 9.2 | 38.4 | 0.24 | 0.43 |
| 1704 | 103 | 0.034 | 71% | 29.4 | 23.1 | 20.1 | 15.6 | 9.1 | 35.7 | 0.26 | 0.78 |
| 1704 | 162 | 0.034 | 66% | 28.1 | 27.5 | 13.5 | 17.2 | 8.6 | 30.7 | 0.28 | 1.27 |
| 1783 | 15 | 0.011 | 67% | 30.0 | 26.5 | 33.4 | 3.0 | 7.1 | 36.3 | 0.20 | 0.09 |
| 1783 | 36 | 0.011 | 69% | 30.2 | 24.5 | 32.5 | 5.0 | 7.6 | 37.5 | 0.20 | 0.15 |
| 1783 | 44 | 0.011 | 70% | 30.2 | 24.2 | 31.9 | 5.8 | 7.8 | 37.6 | 0.21 | 0.18 |
| 1783 | 74 | 0.011 | 70% | 30.1 | 23.7 | 29.4 | 8.3 | 8.0 | 37.7 | 0.21 | 0.28 |
| 1783 | 103 | 0.011 | 70% | 29.8 | 23.8 | 26.7 | 10.6 | 8.1 | 37.3 | 0.22 | 0.40 |
| 1783 | 162 | 0.011 | 69% | 29.2 | 25.0 | 21.8 | 13.9 | 8.1 | 35.6 | 0.23 | 0.64 |

As shown in Table 6, as pressure increases from 3 psig (21 kPag) to 162 psig (1117 kPag), $C_2U$ yields decrease at a slow rate from 37 wt % to 31 wt % for a 33 ms residence time in a temperature profile that peaks at 1704° C. However, the E/A weight ratios increase rapidly with the increase in pressure. For the profile having peak temperature of 1784° C. and an 11 ms residence time, the $C_2U$ yields are roughly constant at about 37 wt %, while the E/A weight ratio again increases with increasing pressure. Accordingly, the higher pressures tend to lead to higher E/A weight ratios, while the $C_{3+}$ levels at these different temperatures and pressures remain relatively constant at around 8 wt % for the two profiles. As a result, the $C_{3+}$ to $C_2U$ weight ratio increases at slow rate for these different temperatures with the higher temperature providing roughly constant $C_{3+}$ to $C_2U$ weight ratio, but the E/A weight ratio increases at a larger rate. Moreover, higher pressures do not have a significant impact on $C_{3+}$ levels as the $C_{3+}$ to $C_2U$ weight ratio remains almost constant, which is an enhancement over the isothermal reactors.

From this table, the regenerative reactor may be utilized to further optimize the distribution the yield of $C_2U$ (e.g., acetylene yield relative to the ethylene yield) for certain operating conditions. That is, a specific pressure, temperature and residence time may be utilized to optimize the distribution of $C_2U$ yield along with the heat profile of the reactor. These operating conditions may be characterized by the $C_{3+}$ to $C_2U$ weight ratio along with an E/A weight ratio, which may be further explained in view of the FIGS. 1E and 1F.

At high-severity operating conditions, higher pressures in the pyrolysis reactor may also reduce the acetylene concentration in the reactor product as compared to the ethylene concentrations or other compounds. This change in concentrations is indicated by the ethylene to acetylene weight ratio, which is noted above. For example, by increasing the pyrolysis reactor from 3 psig (21 kPag) to 103 psig (710 kPag), the acetylene concentration in the reactor product is reduced by 40 wt %, which effectively dilutes the acetylene concentration in the reactor product with ethylene. However, at the higher pressures the acetylene concentrations may be problematic. This aspect is discussed further below.

Figure 1E:
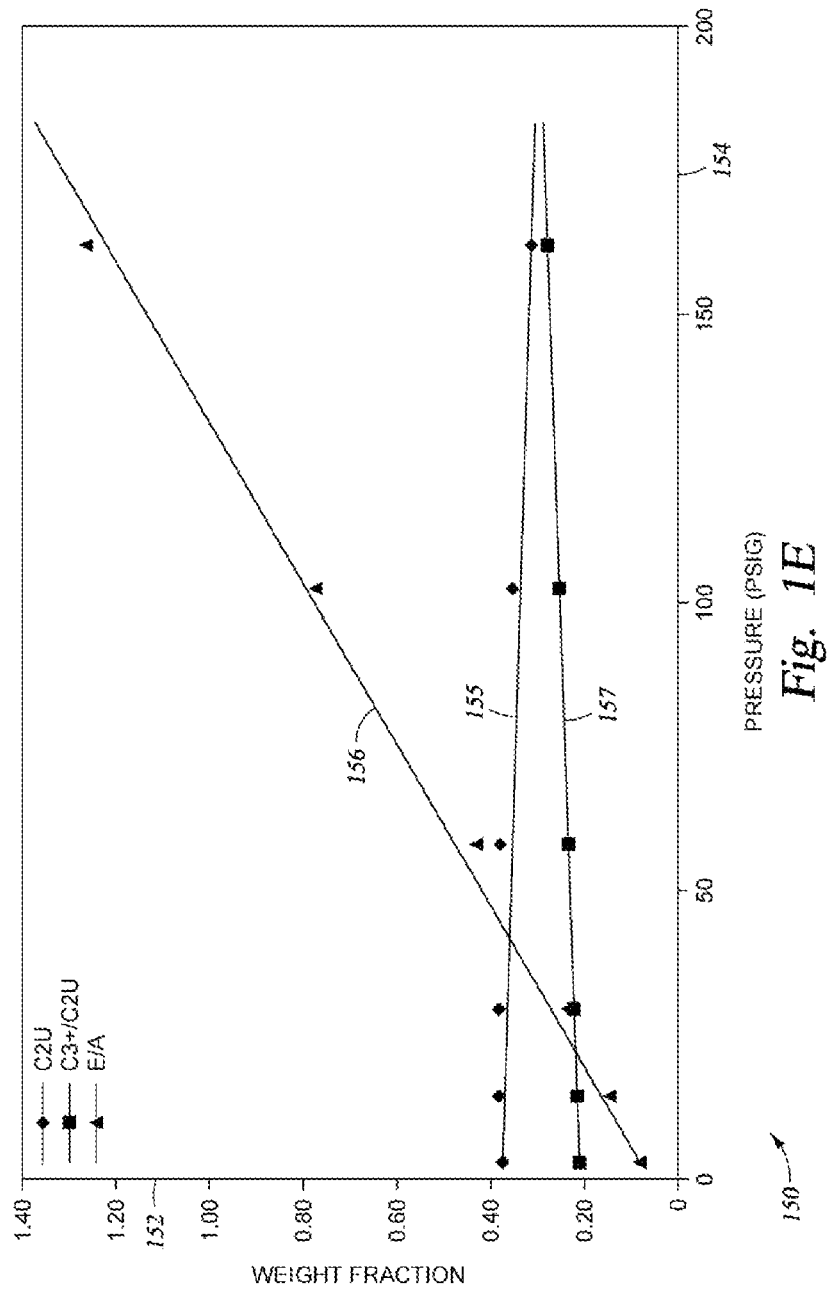
Figure 1F:
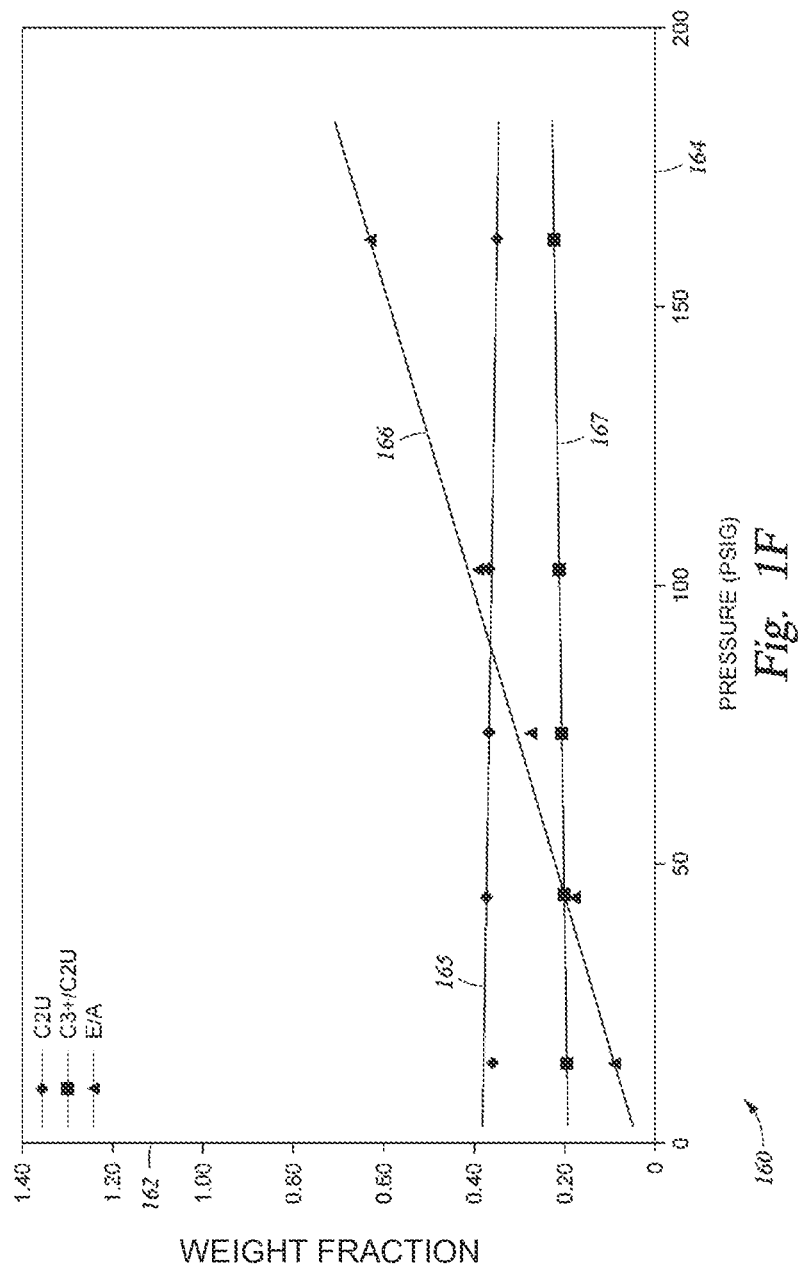

FIGS. 1E and 1F illustrate that the simulation results for different weight ratios of reactor products produced at different pressures for certain temperatures from a methane feed. The results of operating at the various pressures are provided for comparison of the product yields achievable at the residence times associated with the $C_2U$ yield and E/A weight ratio for that pressure. Pyrolysis, in this example, is carried out under regenerative reactor thermal conditions, with 2:1 molar diluent of hydrogen in a methane feed, and with a peak temperature of 1704° C. for diagram 150 and of 1784° C. for diagram 160. All products larger than $C_2$ are considered as $C_{3+}$ in this example and the product is the reaction product yield from the converted pyrolysis feed. In diagram 150, certain values for $C_2U$ yield 155 in wt % of the product, ethylene to acetylene weight ratio 156, and $C_{3+}$ to $C_2U$ weight ratio 157 are shown in weight fraction (or weight ratio) along the Y-axis 152 for various pressures (in psig) along the X-axis 154. The ethylene to acetylene weight ratio 156 and $C_{3+}$ to $C_2U$ weight ratio 157 increases with increasing pressure, while the $C_2U$ yield 155 decreases slightly with increasing pressure. Similarly, in diagram 160, certain values for $C_2U$ yield 165 in wt % of the product, ethylene to acetylene weight ratio 166, and $C_{3+}$ to $C_2U$ weight ratio 167 are shown in weight fraction (or weight ratio) along the Y-axis 162 for various pressures (in psig) along the X-axis 164. The ethylene to acetylene weight ratio 166 increases with increasing pressure, while the $C_2U$ yield 165 and $C_{3+}$ to $C_2U$ weight ratio 157 are relatively constant with increasing pressure. As such, operating conditions of the regenerative thermal pyrolysis reactor may be adjusted to enhance the distribution of the ethylene yield and/or acetylene yield for a given feed.

Although the E/A weight ratio continues to increase with increasing pressure, certain limiting factors may hinder higher pressure operations. For instance, eventually high pressure operating conditions may lead to unacceptable $C_{3+}$ to $C_2U$ weight ratios and/or lower $C_2U$ yields. Further, equipment utilized in the system may be limited to certain pressure ranges. Accordingly, preferred operating pressures may include pressures ≥4 psig (27 kPag), or ≥15 psig (103 kPag), or ≥36 psig (248 kPag), or ≥44 psig (303 kPag) or ≥103 psig (710 kPag), but may be ≤300 psig (2068 kPag), or ≤163 psig (1124 kPag), or ≤150 psig (1034 kPag). As may be appreciated, these different pressures may be combined together to form different combinations depending on the specific configuration of equipment.

In addition, it is beneficial to maintain longer residence times and lower temperatures to maximize E/A weight ratio. However, such residence times and temperatures result in higher weight ratios of $C_{3+}$ to $C_2U$. Accordingly, the design and operating conditions may be adjusted to provide a balance between the E/A weight ratio and the $C_{3+}$ to $C_2U$ weight ratio. That is, the thermal pyrolysis reactor may be operated at lower temperatures to maximize the E/A weight ratio at an efficient and operable $C_{3+}$ to $C_2U$ weight ratio. Alternatively, when lower weight ratios of E/A are preferred, the reactor may be operated at higher temperature and at lower pressure to minimize the E/A weight ratio at an efficient and operable $C_{3+}$ to $C_2U$ weight ratio. As an example, the operating conditions, such as the peak pyrolysis gas temperatures and/or pressure, of the thermal pyrolysis reactor may be adjusted based on an optimized value from an optimization function that comprises an ethylene to acetylene weight ratio and the $C_{3+}$ to $C_2$ unsaturate weight ratio.

The thermal pyrolysis reactor may be limited to certain pressures by various limitations. For instance, at higher pressures and constant residence times, mass density of the gas increases and thus requires higher heat transfer rates per unit of reactor volumes. This heat transfer rate may exceed the capability of the reactor internals or may lead to exceedingly small channels or exceedingly large numbers of channels per square inch (CPSI). Thus, these limitations may eventually lead to impractical reactor dimensions and impractically high levels of pressure drop.

After cracking the feed, the composition of the reactor product may be managed, as part of the process. This may involve managing the concentration of hydrogen, ethylene and/or acetylene. The reactor product near the exit of the reactor or upstream of any recycle may include X mole percent (mole %) of acetylene in the reactor product near the exit of the reactor. For instance, the composition in the reactor product may be controlled by two mechanisms: a light gas separation process (e.g., raw hydrogen removal) and a converter product recycle (e.g., recycling a converter recycle product, such as ethylene). As discussed above, the reactor product has ≥70 mol % hydrogen, and processing the reactor product with hydrogen levels is inefficient and expensive. The reactor product downstream of any recycle and upstream of the acetylene converter may include Y mole percent (mole %) of acetylene in the stream (e.g., the reactor product). In addition, the hydrogen and other diluents may be adjusted to improve acetylene converter selectivity and maintain a maximum acetylene concentration in a safe operating window.

The hydrogen to acetylene ratio may be adjusted for an adiabatic or isothermal fixed bed reactor, as shown by the reference, E. Morozova, Chem & Tech. of Fuels and Oils, V 12, p 268, (1976), which is summarized in Table 7 below.

TABLE 7

| $H_2$:Acetylene Molar Ratio | Methane (vol %) | Ethane (vol %) | Ethylene (vol %) | Acetylene (vol %) | $C_{3+}$ (vol %) |
|---|---|---|---|---|---|
| 20 | 0.1 | 0.4 | 96.7 | 0 | 2.8 |
| 10 | 0.1 | 0.2 | 97.4 | 0 | 2.4 |
| 5 | 0.3 | 0.2 | 96.3 | 0 | 2.4 |
| 3 | 0.2 | 0.1 | 96 | 0.2 | 2.3 |

As shown in Table 7, the high hydrogen and acetylene concentrations over convert the ethylene to ethane and reduce ethylene selectivity. Based on the present techniques, the hydrogen to acetylene ratio may be adjusted for an adiabatic or isothermal fixed bed reactor to be between 20 and 1, preferably between 10 and 2 to enhance acetylene converter selectivity. For example, a regenerative reverse flow reactor may be operated at high-severity operating conditions, where the pyrolysis of this example is carried out with 2:1 molar diluent of hydrogen in a methane feed, and at a reactor pressure of 4 psig (27 kPag) and peak pyrolysis gas temperatures ≥1650° C. with the hydrogen molar concentration about 84 mol % and the acetylene concentration about 6.6 mol % at methane conversions of at least 70%. At these operating conditions, the hydrogen gas to acetylene molar ratio is about 13. At reactor pressures of 103 psig (710 kPag) under these conditions, the hydrogen gas to acetylene molar ratio is ≥18. In an acetylene converter, hydrogen ($H_2$) molar concentrations of ≤40 mol % are preferred to avoid over conversion (e.g., to ethane). In addition, Table 7 indicates that the lower hydrogen diluent provides enhanced selectivity for acetylene conversion into ethylene. Accordingly, a preferred range of $H_2$ to acetylene for selectivity may be between 1.0 and 10.0, between 2.0 and 10.0, or between 3.0 and 8.0.

Figure 1G:
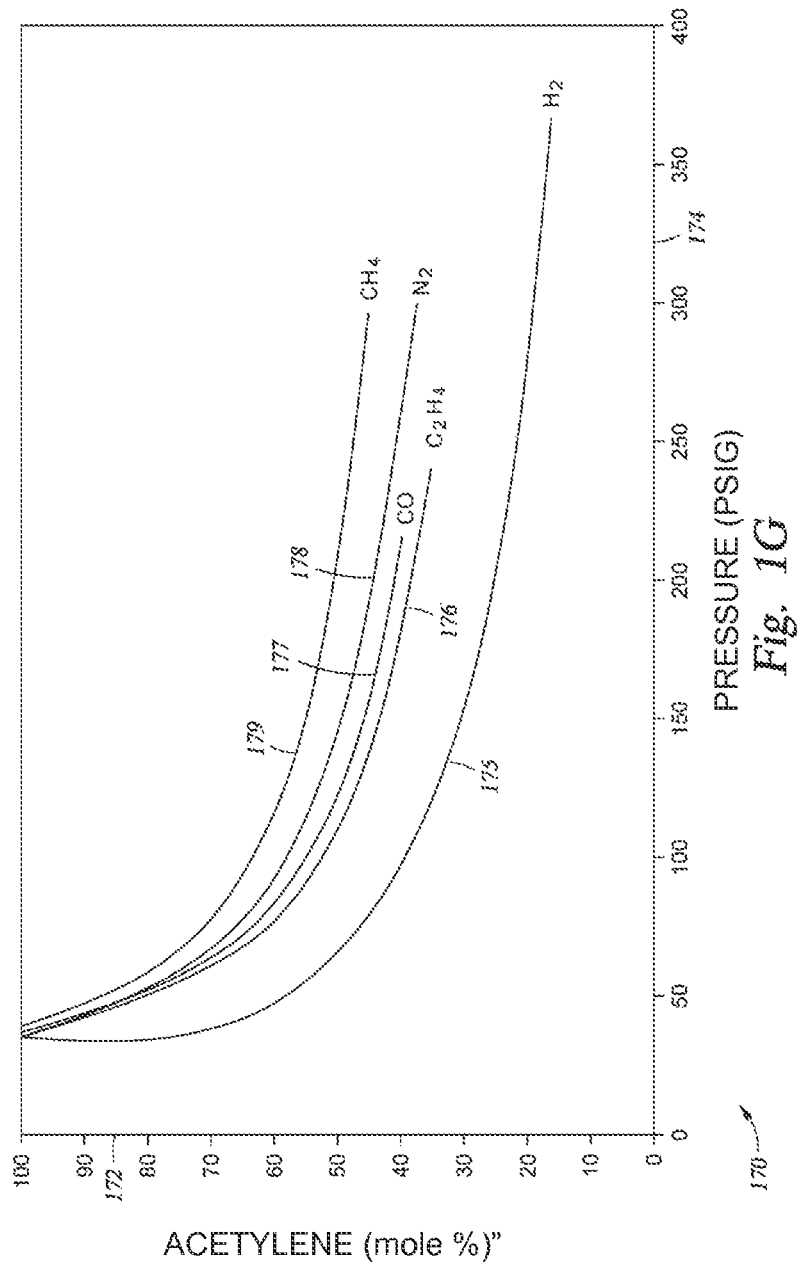
FIG. 1G is a diagram that summarizes acetylene autodecomposition curves for several binary gas blends at a range of concentration and pressures.

However, a maximum acetylene mole percent concentration may be required or preferred based on the acetylene conversion operating conditions (e.g., temperature and pressure). For example, as shown in FIG. 1G, diagram 170 summarizes ($C_2H_2$) autodecomposition curves for several binary gas blends at a range of concentrations and pressures. This example is carried out at 15° C., with a volumetric binary blend of acetylene and another gas (e.g., $H_2$, ethane, CO, $N_2$ and methane). The curve represents the limiting autodecomposition pressure for an acetylene diluent mixture that may be handled in a manner to minimize autodecomposition risks. In diagram 170, the acetylene autodecomposition curve for a hydrogen blend is shown as 175, the acetylene autodecomposition curve for a ethylene blend is shown as 176, the acetylene autodecomposition curve for a carbon monoxide blend is shown as 177, the acetylene autodecomposition curve for a nitrogen blend is shown as 178 and the acetylene autodecomposition curve for a methane blend is shown as 179 as molar percentage of acetylene along the Y-axis 172 as a function of pressures (in psig) along the X-axis 174. To operate a conversion unit, such as an acetylene converter, the molar percentage of acetylene should be maintained below the respective curves 175 to 179. That is, at lower pressures, such as 0 to 50 psig (345 kPag), the molar percentage of acetylene may reach 100%. However, at higher pressures in the acetylene converter, the molar percentage of acetylene decreases at a substantially exponential rate for each of the respective curves 175 to 179. Accordingly, to operate in an efficient regime, the acetylene molar percentage is dependent on the molar ratio of acetylene to other gases at a respective pressure. Of these other gases, the ratio of acetylene to hydrogen is more restrictive in relation to the operating conditions unlike the other gases. Accordingly, for mixtures with high concentrations of hydrogen ($H_2$) and acetylene, the acetylene mole percent concentration should be maintained below the acetylene autodecomposition curve for a hydrogen blend at a given pressure for safe operations, which may be the acetylene non-autodecomposition amount (e.g., an amount within the acetylene non-autodecomposition operating window for a given pressure and temperature).

As may be appreciated the reactor product may include two or more gases, such as acetylene, hydrogen and ethylene, for example. Accordingly, the mole percent concentration may also be maintained for ternary or more complex combinations. For these additional diluent combinations, the acetylene concentration should be maintained below the limiting acetylene concentration curve. Additional acetylene concentration curves may be determined via known processes by those skilled in the art for a specific acetylene blend.

In one or more embodiments, the acetylene to hydrogen ratio may be maintained below the acetylene autodecomposition curve for hydrogen diluent for a given pressure and temperature. The area for acetylene molar concentrations above zero and that is not above the acetylene autodecomposition curve for hydrogen diluent under certain operating conditions is the 'acetylene non-autodecomposition operating window' with an acetylene non-autodecomposition amount being a value within this operating window (depending on temperature and pressure). That is, the acetylene may be below 25 vol % of the feed, while the pressure is below 175 psig (1207 kPag) and temperature of 15° C. As may be appreciated, at higher temperatures, the acetylene autodecomposition curve for different diluents may have lower acetylene concentrations to be within the acetylene non-autodecomposition operating window for a given pressure. As temperature increases at a given pressure, the limiting acetylene concentration below the acetylene autodecomposition curve decreases. As an example for an acetylene and $N_2$ blend at 150 psig (1034 kPag), the limiting acetylene concentration is 47 vol % at 15° C., 40 vol % at 100° C. and 35 vol % at 200° C. The term 'non-autodecomposition amount' of acetylene in a mixture of acetylene and at least a second molecular or atomic species at a specified temperature and pressure means an acetylene amount ≤the amount that would automatically and spontaneously result in the acetylene's autodecomposition at the specified temperature and pressure. This operation of a converter may be performed at concentrations <90.0% of a first acetylene non-autodecomposition amount, <80.0% of a first acetylene non-autodecomposition amount, or even <60.0% of a first acetylene non-autodecomposition amount. For instance, the reactor product may include <90.0% of a first acetylene non-autodecomposition amount, then after separation of the mixture with a recycle product, the stream may include <90.0% of a second acetylene non-autodecomposition amount. The amount of converter recycle product mixed with the retained reactor product may be adjusted to maintain the mixture Y<89.0% of the second acetylene non-autodecomposition amount. Each of these acetylene non-autodecomposition amounts are based on the operating pressure and temperature of the stream.

Further, the acetylene mole percent concentration may be maintained below the acetylene autodecomposition curve for a given pressure and temperature by diluting the acetylene stream with converter product recycle and by controlling the product separation process (e.g., light gas removal process, which may remove hydrogen from the reactor product). In addition, the acetylene mole percent concentration may also be controlled by diluting the acetylene stream with converter product recycle (primarily ethylene) and by controlling the product separation process (e.g., removal of light gases) to improve acetylenes to olefins selectivity. For example, a regenerative reverse flow pyrolysis reactor may be operated at high severity operating conditions, where the pyrolysis of this example is carried out with 2:1 molar diluent of hydrogen in a methane feed, and at a reactor pressure of 4 psig (27 kPag) and peak pyrolysis gas temperatures ≥1650° C. The reactor product may have a hydrogen concentration of 85 mol %, an acetylene concentration of 6.5 mol % and a hydrogen to acetylene molar ratio of 13. The reactor product may then be compressed to 200 psig (1379 kPag) to facilitate light gas separation and acetylene conversion. At 200 psig (1379 kPag), the acetylene concentration at 6.5 mol % is an acetylene non-autodecomposition amount, but to improve acetylene conversion, hydrogen should be reduced. Accordingly, a product separation process (e.g., hydrogen removal) may be utilized to reduce the hydrogen concentration to ≤40 mol %, increasing the acetylene concentration to about 20 mol %. This separation maintains the acetylene concentration below the upper boundary of the acetylene non-autodecomposition operating window (about 26% at these conditions) while lowering the $H_2/C_2H_2$ molar ratio to a value of about 2.0. For example, less removal of $H_2$ may result in a less preferred $H_2/C_2H_2$ molar ratio for hydrogenation selectivity, while more hydrogen removal might result in an acetylene concentration that approached too closely or exceeds the non-autodecomposition boundary. To adjust the acetylene concentration, a converter recycle product (e.g., ethylene) may advantageously dilute the product separation effluent (e.g., acetylene rich product) to maintain the acetylene concentrations within the acetylene non-autodecomposition operating window in a manner that has a reduced impact on the hydrogen to acetylene molar ratio, thus enabling independent tuning of $H_2/C_2H_2$ for improved reactor selectivity and $C_2H_2$ concentration for auto-decomposition management.

As another example, when converting methane in a manner similar to the example above, the stream from the compressor may have 11.6 mole $H_2$, 1.42 mole $CH_4$ and 0.04 moles of $C_2H_4$, all per mole of $C_2H_2$. The product separation unit may be operated such that the remaining $H_2$/acetylene molar ratio (i) equals the hydrogenation target, with the limit that (ii) acetylene concentration is less than the acetylene autodecomposition curve (e.g., an acetylene non-autodecomposition amount). As a further example with the 150 psig (1034 kPag) separation pressure example, if the product separation unit selectively removes hydrogen (e.g., as a membrane separation unit), the process should be configured to remove hydrogen in excess of at least 0.88 mole of hydrogen per mole of acetylene, such that the remaining hydrogen, methane, and ethylene diluents add up to at least 70 mol % of the mixture with the acetylene concentration being below 30 mol %. For example, if the product separation unit is an absorption system that removes methane and hydrogen, then the concentration of diluent may be too low to satisfy the acetylene autodecomposition curve. Then, diluent, such as hydrogen or recycled hydrogenation products, may be used in the desorber or stripping section of the system to dilute the product acetylene concentration to 30 vol %. This diluent concentration may be at least 2.33 moles of diluent per moles of acetylene, for example. As may be appreciated, a similar diluent strategy may be used with other product separation units, such as a membrane and pressure swing adsorption.

Unless otherwise stated, all percentages, parts, ratios, etc., are by weight. Unless otherwise stated, a reference to a compound or component includes the compound or component by itself, as well as in combination with other compounds or components, such as mixtures of compounds. Unless otherwise stated, all pressures are given as gauge pressure, which is as pressures above standard atmospheric pressure (e.g., psig).

Further, when an amount, concentration, or other value or parameter is given as a list of upper preferable values and lower preferable values, this is to be understood as specifically disclosing all ranges formed from any pair of an upper preferred value and a lower preferred value, regardless whether ranges are separately disclosed.

The terms "convert" and "converting" are defined broadly herein to include any molecular decomposition, cracking, breaking apart, conversion, and/or reformation of organic molecules (hydrocarbons) in the feed, by means of at least pyrolysis heat, and may optionally include supplementation by one or more of catalysis, hydrogenation, diluents, and/or stripping agents.

As used herein, the expression "non-volatiles" may be defined broadly herein to mean substantially any resid, metal, mineral, ash, ash-forming, asphaltenic, tar, coke, and/or other component or contaminant within the feedstock that does not vaporize below a selected boiling point or temperature and which, during or after pyrolysis, may leave an undesirable residue or ash within the reactor system, which is difficult to remove. Noncombustible nonvolatiles may include ash, for example. Methods for determining asphaltenes and/or ash may include American Society of Testing and Materials (ASTM) methods, such as methods for asphaltenes may include ASTM D-6560 and D-7061 and methods for ash may include ASTM D-189, D-482, D-524, and D-2415.

As used herein, the terms "coke" and "soot" may refer to hydrocarbonaceous material that accumulates within the reactor during pyrolysis or to solid-phase hydrocarbonaceous materials that emerge from the reactor with pyrolysis effluent. The hydrocarbonaceous material that accumulates within the reactor during pyrolysis may also be defined as the fraction of the pyrolysis feed that remains in a thermal pyrolysis reactor and thus does not emerge from the reactor as pyrolysis effluent. Coke and soot are components of the reactor product, which are included for $C_{3+}$ product for pyrolysis selectivity. The terms "$C_3^+$" and "$C_{3+}$" mean all products of the pyrolysis feed having more than three carbon atoms, which include coke and soot, whether those products emerge from the reactor or remain within the reactor. The reactor product that does emerge may be referred to as the reactor effluent, which is at least a portion of the reactor product.

The term "pyrolysis feed" means the composition, which may be a mixture, subjected to pyrolysis. In one embodiment, the pyrolysis feed is derived from a hydrocarbon feed (e.g., by separation of a portion from the hydrocarbon feed and optional addition of diluents).

As used herein, the "hydrocarbon feed" contains hydrocarbons (C bound to H) and may contain (i) minor components of heteroatoms (<10 wt %) covalently bound to hydrocarbons and (ii) minor components of heteroatoms (<10 wt %) not bound to hydrocarbons (e.g., $H_2O$), wherein these weight percents are based on the weight of the hydrocarbon feed. The term "hydrocarbons in the hydrocarbon feed" or "hydrocarbons of the hydrocarbon feed" means molecules within the hydrocarbon feed that contain at least hydrogen and carbon and, optionally, heteroatoms covalently bound to a portion of such molecules. Weight percents of hydrogen and carbon, as used to characterize the hydrocarbon feed, are typically provided as a percent of the hydrocarbons in the hydrocarbon feed. The hydrocarbon feed may include, by way of non-limiting examples, one or more of Fischer-Tropsch gases, methane, methane containing streams such as coal bed methane, biogas, associated gas, natural gas and mixtures or components thereof, steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, hydrocarbon streams derived from plant or animal matter, and/or any mixtures thereof.

As used herein, the expression "advantaged feed" means a feed that has a lower cost (per ton or per heating value) than Brent reference crude oil and may include, by way of non-limiting examples, one or more methane containing feeds and one or more high-aromatic containing streams. Some examples may include one or more of Fischer-Tropsch gases, methane, methane containing streams such as coal bed methane, biogas, associated gas, natural gas and mixtures or components thereof, steam cracked gas oil and residues, gas oils, coker naphtha, steam cracked naphtha, catalytically cracked naphtha, hydrocrackate, reformate, raffinate reformate, natural gasoline, Fischer-Tropsch liquids, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, and/or any mixtures thereof.

The term "hydrogen content" means atomic hydrogen bound to carbon and/or heteroatoms covalently bound thereto and which excludes molecular hydrogen ($H_2$) in the hydrocarbon feed expressed as a weight percent based on the weight of the hydrocarbons in the hydrocarbon feed. Hydrogen content as applied to pyrolysis feed or reactor feed are expressed as an ASTM weight percent of hydrocarbons in the respective feed. As used herein, the expression "low hydrogen content feed" or "low hydrogen content hydrocarbon feed" means a feed with a hydrogen content of ≤about 14 wt %. The hydrogen content of hydrocarbon feeds, reactants and products for present purposes can be measured using any suitable protocol, e.g., ASTM D4808-01(2006) Standard Test Methods for Hydrogen Content of Light Distillates, Middle Distillates, Gas Oils, and Residua by Low-Resolution Nuclear Magnetic Resonance Spectroscopy or ASTM D5291-10 Standard Test Methods for Instrumental Determination of Carbon, Hydrogen, and Nitrogen in Petroleum Products and Lubricants. Examples of the low hydrogen content hydrocarbon feeds include one or more of steam cracked gas oil and residues, gas oils, heating oil, diesel, gasoline, coker naphtha, steam cracked naphtha, catalytically cracked naphtha, reformate, raffinate reformate, distillate, crude oil, atmospheric pipestill bottoms, vacuum pipestill streams including bottoms, heavy non-virgin hydrocarbon streams from refineries, vacuum gas oil, heavy gas oil, atmospheric resid, heavy residuum and mixtures thereof. The low hydrogen content hydrocarbon feedstock may have a nominal end boiling point of at least 400° F. (204° C.), (e.g., ≥400° F., such as in excess of 1200° F. and even in excess of 1500° F.) and commonly has a nominal end boiling point of at least 500° F. (260° C.). Some preferred hydrocarbon feedstocks include crude oil, atmospheric and vacuum resids, tars, fuel oils and cycle oils. Such heavier, more aromatic feeds are typically lower cost, per unit weight, but may yield lower acetylene and ethylene yields and higher carbon or tar yields. Especially preferred feeds include aromatic feed, gas oils, cracked gas oils, crude, atmospheric resid feed, vacuum resid feed, tars, coal tars and heavy feed containing pitch. Due to the high aromatic content of the heavier feeds, the feeds have low hydrogen content (typically <about 11 wt % atomic hydrogen content). During pyrolysis, the hydrogen deficient feeds may form tar, coke, or soot.

The pyrolysis feed, as described further below, is the feed to the thermal pyrolysis reactor, and may contain one or more hydrocarbon feeds as well as a hydrogen ($H_2$) containing feed. The pyrolysis feed may include hydrogen gas ($H_2$) in an amount that provides a preferred ratio of hydrogen gas ($H_2$) moles to the total moles of carbon (C) in the hydrocarbon components of the pyrolysis feed. The ratio of hydrogen to carbon ($H_2$/C) may be from 0.0 or 0.1 to 5.0, such as 0.0, 0.1, 1.0, 2.0, 3.0, 4.0, 5.0, or values in between.

Combining the hydrogen content of the hydrogen gas to the hydrogen and carbon contents of the hydrocarbon components of the pyrolysis feed may result in a total atomic ratio of hydrogen (H) to carbon (C) in the pyrolysis feed that is from 3 to 15. The weight percent of total hydrogen in the pyrolysis feed may be greater than that in the hydrocarbon feed. For example, the weight percent of total hydrogen in the pyrolysis feed may be between 8 wt % and 54 wt %.

As used herein, the expression "combustion feed" means the two or more individual feeds that are to be combined to form a combustion reaction or a mixture of two or more feeds, such as a combustion fuel that does not contain oxidants (e.g., $O_2$) or non-combustible non-volatiles and a combustion oxidant that may include an oxygen or oxygen containing fluid. The combustion fuel may include, by way of non-limiting examples, one or more of Fischer-Tropsch gases, methane, methane containing streams such as coal bed methane, biogas, associated gas, natural gas and mixtures or components thereof, synthesis gas (mixtures of CO and $H_2$), and hydrogen. The combustion oxidant may include, but are not limited to, air, oxygen or mixtures thereof. Any of the combustion feed, fuel, or oxidant may additionally include non-combustible but volatile diluents such as $N_2$, $CO_2$, $H_2O$, and/or other inert gases.

The term "reactor", as used herein, refers to equipment used for chemical conversion. As such, several items identified as reactors may be combined to become a single entity that is also identified as a reactor, in that individual and combined entities may all be characterized as equipment used for chemical conversion. The regenerative reverse-flow thermal pyrolysis reactors described herein may comprise first and second reactor entities, for example as described in U.S. Patent App. Pub. No. 20070191664.

The term "pyrolysis reactor", as used herein, refers to a system for converting hydrocarbons by means of at least pyrolysis chemistry. As used herein, the pyrolysis reactor may include pyrolysis chemistry alone (e.g., in the absence of oxygen for the conversion), or may also include combustion chemistry, including combustion chemistry that occurs along with the pyrolysis chemistry as in a partial combustion reactor. The pyrolysis reactor may include one or more reactors and/or associated equipment and lines. A region, as used herein, refers to a location within the pyrolysis reactor, which may include one or more reactors and/or associated equipment and lines. The region may include a specific volume within a reactor, a specific volume between two reactors and/or the combination of different disjointed volumes in one or more reactors. The regenerative reverse-flow thermal pyrolysis reactors described herein may comprise first pyrolysis reactor and second pyrolysis reactor, for example as described in U.S. Patent App. Pub. No. 20070191664.

As used herein, the "thermal pyrolysis reactor" includes at least predominantly pyrolysis chemistry. Pyrolysis or pyrolysis chemistry, such as the conversion of hydrocarbons to unsaturates such as ethylene and acetylene is an endothermic process requiring addition of heat. The terms crack and cracking may be used interchangeably with the terms pyrolyse and pyrolysis. In a thermal pyrolysis reaction, ≥50%, ≥80%, or ≥90%, of this heat is provided by heat transfer via solid surfaces such as tubulars or bed materials. Any combustion chemistry that occurs within the pyrolysis stream of a thermal pyrolysis reactor provides a minority of the endothermic heat of pyrolysis, such as ≤50%, ≤20%, or ≤10% of the endothermic heat of pyrolysis.

The term "high-severity operating conditions" means pyrolysis conditions resulting in the conversion of the a pyrolysis feed comprising hydrocarbons to make a product having an acetylene content ≥10.0 wt % based on the weight of the hydrocarbons in the pyrolysis feed. The operating conditions for a thermal pyrolysis reactor may be characterized by a severity threshold temperature that divides low-severity operating conditions in thermal pyrolysis reactors from high-severity operating conditions in thermal pyrolysis reactors. The severity threshold temperature is defined as the lowest temperature at which the feed to the reactor may react at a residence time ≤0.1 sec (second) to make at least 10 wt % acetylene as a percent of the hydrocarbons in the feed evaluated at the given operating conditions of the process. The high-severity operating conditions for a thermal pyrolysis reactor may be characterized as peak pyrolysis gas temperatures that are greater than the severity threshold temperature. The low-severity thermal pyrolysis reactor may be characterized as pyrolysis gas temperatures that are less than the severity threshold temperature and no pyrolysis gas temperatures that exceed the severity threshold temperature. For example, for the thermal conversion of methane at a pressure of 14.7 psig (101 kPag) and with 2:1 molar ratio of hydrogen diluent, the threshold temperature is about 1274° C. for this process. At temperatures at or above 1274° C., yields of acetylene can exceed 10 wt % of the starting methane, at some time ≤0.1 seconds. Conversely, at temperatures below 1274° C., there are no times ≤0.1 seconds for which yields of acetylene reaches 10 wt % of the starting methane.

According to one or more embodiments of the present techniques, an enhanced process is provided for the production of $C_2U$ (e.g., acetylene and ethylene), which are useful for manufacturing polyolefins and other petrochemical products. The process may include various stages, such as feed preparation, pyrolysis, recovery and further processing, such as separation of the polymer grade monomer and polymerization to polyethylene. In one or more of these stages, the process manages the amount of hydrogen to enhance the process. The thermal pyrolysis reactor may involve operating conditions that are below a specific selectivity threshold, such as a $C_{3+}$ to acetylene weight ratio ≤0.5, or ≤0.45 or ≤0.4. Operation at low levels of $C_{3+}$/acetylene is desirable both to improve process economics and to improve process operability. Economics are improved by low $C_{3+}$/acetylene weight ratio because $C_{3+}$ products produced by high-severity pyrolysis are less valuable than the acetylene product. Further, operability is improved by low $C_{3+}$/acetylene weight ratio because $C_{3+}$ products may include substantial amounts of coke, whose production may hinder operations. Specifically, coke produced in excess amounts may result in an inability to maintain the thermal pyrolysis reactor channels available for fluid flow, and coke produced in excess amounts may result in heat release (during combustion or regeneration steps), which is greater than the heat amounts that can be used in the process or reactor. At least a portion of the reactor product may be further processed to recover polyolefins (e.g., polyethylene), benzene or other final products.

Further, in one or more embodiments of the present techniques, an enhanced process is provided for the production of a specific distribution of $C_2U$ (e.g., acetylene yield and ethylene yield), which are useful for manufacturing polyolefins and other petrochemical products. In particular, the present techniques may involve operating conditions that may include a $C_{3+}$ to $C_2U$ weight ratio ≤0.5, or ≤0.4, or ≤0.3. These operating conditions may be utilized to manage the amount of ethylene and acetylene for further processing. By managing the size and capacity of the equipment for acetylene conversion, the process units may be smaller and involve less capital expense. Further, by operating at certain pressure ranges, the use of compression for recovery stages may be minimized or eliminated.

In addition to operating the thermal pyrolysis reactor at different operating conditions, the present techniques may involve managing the hydrogen content of the feeds and products to enhance the process. That is, hydrogen may be managed for feeds to the thermal pyrolysis reactor and reactor products from the thermal pyrolysis reactor may be managed through the conversion (e.g., hydrogenation) process to enhance the overall process. Hydrogen and carbon levels in hydrocarbon feeds, as used to manage the hydrogen level of the pyrolysis feed, such as in the terms of equation e1 and e2, are related to hydrogen contents but are expressed as parameters as a weight percent of the entire streams that are being mixed to form the pyrolysis feed. The hydrogen parameter for any feed means the weight of hydrogen bound to carbon and/or heteroatoms covalently bound thereto in the feed, expressed as a weight percent of the feed. The carbon parameter of any feed means the weight of carbon bound to hydrogen and/or heteroatoms covalently bound thereto in the feed, expressed as a weight percent of the feed. Hydrogen and carbon parameters are proportional to hydrogen and carbon contents, and the parameter can be calculated from the respective content by multiplying by the weight fraction of hydrocarbons in the feed. As such, changes that effect the hydrogen or carbon content may similarly change the respective parameter. In particular, the hydrogen and carbon parameters of a first hydrocarbon feed may be determined via a calculation prior to the feed being provided to the unit, may be obtained from information about the feed, or may be based on measurements of the feed. These hydrogen and carbon parameters are abbreviated herein as HHC1 and CHC1, respectively. The weight based rate (WT1) of the first hydrocarbon feed may be provided or adjusted to a certain level.

If the feed hydrogen parameter (HHC1) is below a hydrocarbon hydrogen target level (abbreviated HHCT), such as a hydrogen parameter of 6 wt % (weight percent) to 20 wt %, or between 12 wt % to 18 wt %, the hydrogen parameter may be adjusted to increase the hydrogen parameter of the pyrolysis feed. This adjustment may involve combining the first hydrocarbon feed with a second hydrocarbon feed and optionally with a hydrogen ($H_2$) containing stream. The amounts of added second hydrocarbon feed and hydrogen ($H_2$) containing stream may be calculated as the amounts needed to result in a pyrolysis feed that achieves the hydrocarbon hydrogen target level (HHCT), and also that achieves the total atomic hydrogen to carbon ratio target level (abbreviated HCRT), which may be from about 3 to about 15. Hydrocarbon hydrogen target level (HHCT) is a target level of hydrocarbon hydrogen content in the pyrolysis feed, given on the same basis (wt % of feed) as the hydrogen parameters. The total atomic hydrogen to carbon ratio target level (HCRT) is a target level for the pyrolysis feed for the ratio of the total weight of atomic hydrogen contained in molecular $H_2$ and in hydrocarbons of the pyrolysis feed, divided by the weight of carbon in the hydrocarbons of the pyrolysis feed.

The second hydrocarbon feed may also be characterized in terms of hydrogen and carbon parameters, expressed as weight percents of the second hydrocarbon feed, and abbreviated as HHC2 and CHC2, respectively. A hydrogen ($H_2$) containing stream may be characterized in terms of the weight percent $H_2$ gas in the stream (abbreviated HH2D) as well as the weight percent of any hydrocarbon content (HCD), which may be further characterized as the weight percent of hydrogen and carbon that is present in any hydrocarbons in the stream, expressed as weight percent of total hydrogen ($H_2$) containing stream and abbreviated HHCD and CHCD, respectively.

Given a pyrolysis feed target for hydrocarbon hydrogen level (HHCT) and total atomic hydrogen to carbon ratio (HCRT), and given a weight based rate (WT1) of first hydrocarbon feed, the weight based rate (WT2) of second hydrocarbon feed and weight based rate (WTD) of hydrogen ($H_2$) containing stream may be calculated by solving the following equations e1 and e2.

$$HHC1*WT1+HHC2*WT2+HHCD*WTD=HHCT*(WT1+WT2+WTD*HCD) \quad (e1)$$

$$(12*(HHC1*WT1+HHC2*WT2+(HH2D+HHCD)*WTD))/(CHC1*WT1+CHC2*WT2+CHCD*WTD)=HCRT \quad (e2)$$

The following is an example of how these equations may be used. The weight based rate (WT1) of the first hydrocarbon feed is 1 kilogram/hour (kg/hr) flow rate of a first hydrocarbon feed that is a hydrogen deficient hydrocarbon feed having hydrogen parameter (HHC1) of 10 wt % and carbon parameter (CHC1) of 90%. A second hydrocarbon feed, methane gas in this example, has a hydrogen parameter (HHC2) of 25 wt % and carbon parameter (CHC2) of 75 wt %. A hydrogen ($H_2$) containing stream is available that is composed of 95 mole percent (mol %) hydrogen and 5 mol % methane. Such a stream has a hydrogen ($H_2$) content (HH2D) of 70.4 wt %, a hydrocarbon content (HCD) of 29.6 wt %, and a hydrocarbon hydrogen and carbon content (HHCD, CHCD) of 7.4 wt % and 22.2 wt % of the total $H_2$-containing stream, respectively. For a hydrocarbon hydrogen level target (HHCT) of 16 wt % and total atomic hydrogen to carbon ratio target (HCRT) of 8.0, the two equations e1 and e2 may be solved to prescribe a weight based rate (WT2) of the second hydrocarbon feed that is 0.386 kg/hr and a weight based rate (WTD) of hydrogen ($H_2$) containing stream that is 0.947 kg/hr. Equations e1 and e2 are robust and reliably provide flow rate solutions for practical pyrolysis feed situations. In certain examples, the solution of the equations e1 and e2 may indicate that the second hydrocarbon stream or the hydrogen ($H_2$) containing stream has a flow rate of zero. That is an acceptable solution, and simply means that the indicated stream is not needed to satisfy the pyrolysis feed target specifications, such as the atomic hydrogen to carbon ratio (HCRT) and hydrocarbon hydrogen level (HHCT). If provided with impractical situations, the equations typically generate a negative value for a flow rate. For example, if the hydrocarbon hydrogen target level (HHCT) is set above the hydrogen parameters both hydrocarbon feeds (HHC1 and HHC2), there is no combination of the streams that can satisfy the target level. Similarly, if the total atomic hydrogen to carbon ratio target level (HCRT) is set below the atomic hydrogen to carbon ratio level of the reactor feed, there is no positive amount of hydrogen ($H_2$) containing stream that can be added to lower the total H/C level. Thus, negative flow values are an indication that the pyrolysis feed situation can not be solved for the target levels and feeds provided.

As an example of managing the hydrogen for the thermal pyrolysis reactor, two hydrocarbon feeds may be combined with a hydrogen diluent or hydrogen ($H_2$) containing stream prior to cracking within the thermal pyrolysis reactor. In particular, the first hydrocarbon feed may have a hydrogen parameter level below 20 wt %, or below 14% while the second hydrocarbon feed may have a hydrocarbon content level above 14% or more likely above 20 wt %. The weight based rate of first hydrocarbon stream may be ≥5 wt % of the combined first and second hydrocarbon streams. First and second hydrocarbon streams are combined to form a reactor feed, wherein the first hydrocarbon feed is ≥5 wt % of the reactor feed and the second hydrocarbon feed is between the remaining portion of the reactor feed and 5 wt % of the reactor feed. A hydrogen ($H_2$) containing stream may be combined with the hydrocarbon stream(s) to form a pyrolysis feed having a total atomic hydrogen to carbon (H/C) ratio of the combined feeds from 3 to 15. In other instances, when there are minimal components other than hydrogen and hydrocarbon, the weight percent of total hydrogen in the pyrolysis feed may be between 8 wt % and 54 wt %. The resulting pyrolysis feed is exposed to high-severity operating conditions in a thermal pyrolysis reactor to produce a reactor product comprising hydrogen, ethylene and acetylene. This thermal pyrolysis reactor may be operated under pressures and temperatures to obtain the specific ratios, such as E/A weight ratio or $C_{3+}/C_2U$ weight ratios, as noted above.

The combining of the first hydrocarbon feeds may be performed in various methods, which are known to those skilled in the art. Each of the three streams may be mixed simultaneously, or mixed pair-wise in any sequence. If the hydrogen ($H_2$) containing stream is produced using a separation process that benefits from sweep flow, such as a membrane, absorption, or absorption system, then a fraction of one or more of the hydrocarbon streams may be used as the sweep or diluent stream. Likewise, if the first hydrocarbon stream is produced in a separation process that benefits from a gaseous stream, for example, to aid in vapor liquid separation, some fraction of the second hydrocarbon stream or hydrogen ($H_2$) containing stream may be used as part of that process. In another embodiment, a fraction of the second hydrocarbon stream and/or hydrogen ($H_2$) containing stream may be used to strip the first hydrocarbon stream from a base hydrocarbon stream that contains non-volatiles.

Further, as discussed above, the operating conditions that provide low $C_{3+}/C_2U$ or low E/A weight ratios typically yielded high concentrations of hydrogen ($H_2$) gas relative to the $C_2U$ concentration levels in the reactor product. For methane containing feeds at 70 wt % conversion, hydrogen ($H_2$) gas concentrations may range from 20 wt % to 40 wt % and $C_2U$ may range from 30 wt % to 50 wt %. In mole percent (mol %), $H_2$ concentrations may be ≥70 mol % of the reactor product and $C_2U$ levels may be as high as 20 mol % $C_2U$ of the reactor product. In the examples of Tables 2, 3, 5, and 6 that have $C_{3+}/C_2U$ values in the preferred range of ≤0.5, the reactor product has a weight ratio of $H_2$ to $C_2U$ of between 0.65 and 1.5. Adjusting for molecular weight gives an $H_2/C_2U$ molar ratio between about 8 and 20, and consequently a molar ratio of $H_2$ to acetylene that is somewhat higher.

Accordingly, high concentrations of $H_2$ gas in the reactor product have to be managed to efficiently and selectively convert the acetylene into ethylene. Although more moderate levels of $H_2$ gas may be preferred to aid in subsequent acetylene conversion reactions, high molar concentrations of $H_2$ gas are difficult to compress to reach preferred operating conditions necessary to convert acetylenes into olefins and may also effect the converter selectivity of acetylenes to olefins. Regardless, a portion of $H_2$ gas is preferentially removed via a product separation process (e.g., a hydrogen ($H_2$) or light gas separation process) prior to converting the acetylenes into olefins. For instance, a hydrogen $H_2$ removal process may preferentially reduce the $H_2$ gas level to ≤50 mol % or more preferentially ≤40 mol % (to improve acetylene converter selectivity). However, if the acetylene conversion process is operated at pressure ≥75 psig (517 kPag) in the mixed or vapor phase, low levels of $H_2$ gas (or conversely high levels of acetylenes) should be avoided to reduce the risk of acetylene autodecomposition. Accordingly, a non-autodecomposition operating window for managing levels of diluent (e.g., hydrogen ($H_2$)), while processing the reactor product from the reactor (e.g., practicing high severity pyrolysis) is used to control diluent gas concentration levels to be below the concentrations on the acetylene autodecomposition curve (e.g., the minimum $H_2$ concentration, which is typically the most limiting diluent).

Accordingly, the operating conditions of the arc or thermal pyrolysis reactor and the recovery stage may include processes to manage the hydrogen content of the feeds and products throughout the process. That is, the operational settings of the equipment may be adjusted to manage the hydrogen through the process. These adjustments may include changing the operating settings to change the pressure within the reactor and/or the temperature within the reactor, or in subsequent units, such as a converter. The adjustments may also include increasing the heat generated by providing different combustion feeds to the thermal pyrolysis reactor. Further, the operational settings may be adjusted based on the composition (e.g., hydrogen, ethylene or acetylene content) of the stream (e.g., feed or product at the various stages). The present techniques may be further understood with reference to the FIGS. 2 to 4, which are discussed below.

Figure 2:
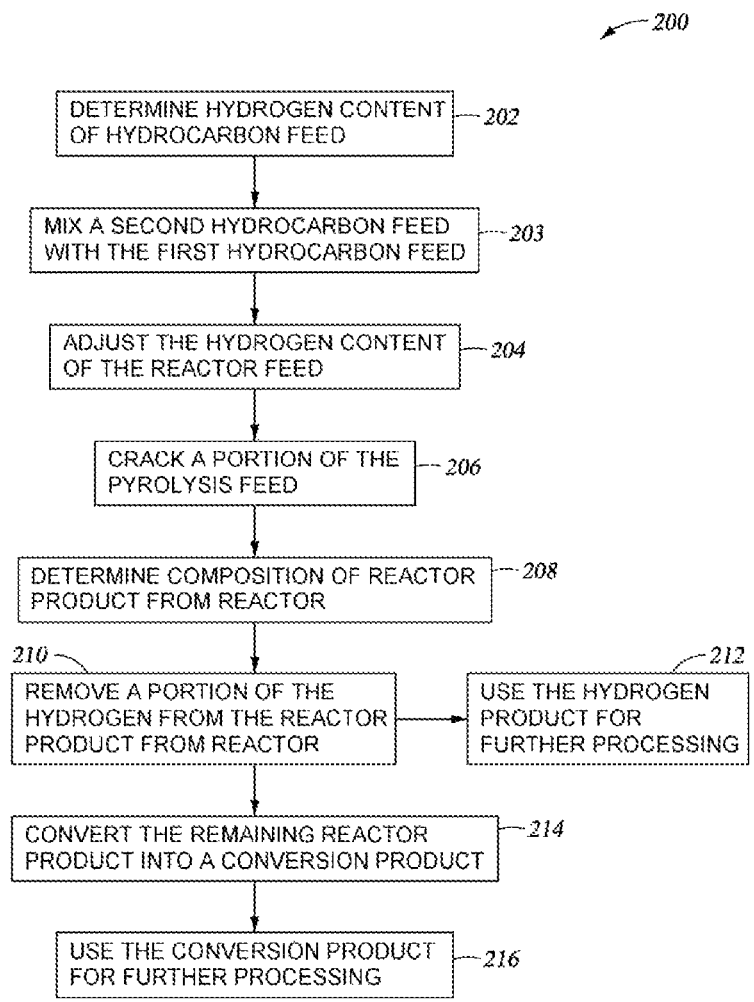
FIG. 2 is a simplified process flow diagram illustrating an embodiment of the present techniques.

To begin, an exemplary embodiment of the present techniques is illustrated in the block flow diagram 200 of FIG. 2. In this flow diagram 200, a process is described for the production of ethylene or propylene, which subsequently may be used in the manufacture of polyolefins, such as polyethylene. In this block diagram, the process includes various stages, which may involve managing the hydrogen content of the feed and products, as noted below. For instance, a feed preparation stage is described in blocks 202, 203 and 204. A cracking stage is described in block 206, which involves cracking the pyrolysis feed in a thermal pyrolysis reactor, which produces a reactor product. Then, a recovery stage is described in blocks 208 to 216, which further processes the reactor product or reactor effluent to produce acetylene, ethylene and/or propylene. In this process, the feed preparation stage and recovery stage may involve managing the amount of hydrogen utilized in these or subsequent stages to further enhance the process.

At block 202, a hydrogen content and/or parameter of a first hydrocarbon feed is determined. The first hydrocarbon feed may also have a hydrogen content level below 20 wt % of the first hydrocarbon feed, ≤16 wt % of the first hydrocarbon feed, ≤14 wt % of the first hydrocarbon feed or ≤12 wt % of the first hydrocarbon feed. This first hydrocarbon feed may include one or more high-aromatic containing streams, aromatic gas oil, steam cracked gas oil and residues, atmospheric pipestill bottoms, vacuum pipestill streams, any mixtures thereof, and/or any other low hydrogen content hydrocarbon feed. The determination of the hydrogen content level may include obtaining information about the hydrocarbon feed, providing the hydrocarbon feed to a hydrogen measurement device such as nuclear magnetic resonance spectroscopy, or other suitable technique.

Then, at block 203, a second hydrocarbon feed may be mixed with the first hydrocarbon feed to form a reactor feed. The process may include blending the first hydrocarbon feed with the second hydrocarbon feed, such as methane or other hydrogen rich feeds, to provide the blended hydrocarbon mixture. The feeds may be preferentially mixed in the vapor phase and/or may be heated to allow mixing in the vapor phase. The feeds may be mixed in a manifold, sparger, a vaporizer, stripper or heated vapor liquid separator or other suitable mixing unit. Further, the second hydrocarbon feed may be used to vaporize and/or strip the first hydrocarbon feed to form a vapor phase that is the reactor feed. The second hydrocarbon feed has a higher hydrogen content than the first hydrocarbon feed to form the reactor feed. The second hydrocarbon feed may include, by way of non-limiting examples, one or more of Fischer-Tropsch gases, methane, methane containing streams such as coal bed methane, biogas, associated gas, natural gas and mixtures or components thereof. The amount of the second hydrocarbon feed may be adjusted to raise the hydrocarbon hydrogen parameter of the pyrolysis feed to be at the hydrocarbon hydrogen target level and/or at the total atomic hydrogen to carbon ratio target level, as discussed above. These feeds may be combined to form a reactor feed, wherein the first hydrocarbon feed is ≥5 wt % of the reactor feed, ≥25 wt % of the reactor feed, ≥35 wt % of the reactor feed. The second hydrocarbon feed is between the remaining portion of the reactor feed and 5 wt % of the reactor feed. That is, the first hydrocarbon feed may range from 5 wt % to 95 wt % of the reactor feed, from 25 wt % to 75 wt % of the reactor feed, or 35 wt % to 65 wt % of the reactor feed, while the second hydrocarbon feed is between the remaining portion and 5 wt % of the reactor feed, between the remaining portion and 25 wt % of the reactor feed, or between the remaining portion and 35 wt % of the reactor feed, respectively. The proportion of first and second hydrocarbon feed may be set such that the hydrocarbons of the reactor feed have a hydrogen parameter that equals the hydrocarbon hydrogen level target (HHCT).

At block 204, the hydrogen content and/or parameter of the pyrolysis feed may be further adjusted. The adjustment of the pyrolysis feed may include combining the reactor feed with a hydrogen ($H_2$) containing stream that has higher hydrogen content than the hydrocarbon feed to form a pyrolysis feed. The amount of the hydrogen ($H_2$) containing stream may be controlled to raise the hydrogen parameter of the reactor feed to within the total atomic hydrogen to carbon ratio target level. The hydrogen parameter of the pyrolysis feed may be adjusted to have a total atomic hydrogen to atomic carbon (H/C) ratio of the hydrogen ($H_2$) and hydrocarbon of the pyrolysis feed is between 3 and 15, between 5 and 12, or between 6 and 9. In some instances, particularly when the pyrolysis feed has limited components beyond hydrogen gas and hydrocarbons, the pyrolysis feed may be adjusted by means of adjusting the flow rate of hydrogen ($H_2$) containing feeds, to achieve a specific hydrogen threshold, such as an atomic hydrogen amount of ≥20 wt % and ≤54 wt % of the pyrolysis feed, or an atomic hydrogen amount of ≥25 wt % or ≤54 wt % of the pyrolysis feed, for example. Further, the process may involve adjusting effective partial pressure of the reactor feed, for example by adjusting the pressure of the reactor feed. In certain embodiments, the process may involve measuring the hydrogen content of the hydrocarbon feed(s) to determine the hydrogen and carbon parameter and adjust the amount of hydrogen ($H_2$) containing stream total atomic hydrogen to carbon ratio target (HCRT), as discussed previously. The hydrogen ($H_2$) containing stream may include hydrogen from a source external to the process, hydrogen from a recycle product, or other suitable hydrogen source. The hydrogen ($H_2$) containing stream may include hydrogen ($H_2$) or steam, for example. If a hydrocarbon feed material contains non-volatiles and the second hydrocarbon feed contains volatiles, a portion of the second hydrocarbon feed and/or the hydrogen ($H_2$) containing stream may be combined with said hydrocarbon feed material in or prior to a heated vapor liquid separator to strip or flash or volatilize a portion of said hydrocarbon feed material, thus facilitating separating said hydrocarbon feed material into a volatile portion that is the first hydrocarbon feed and a non-volatile residue.

After the feed preparation stage, the pyrolysis feed is cracked in block 206. The cracking of the pyrolysis feed may involve the use of a thermal pyrolysis reactor to convert the pyrolysis feed into a reactor product. The reactor product includes one or more $C_2U$, and optionally includes hydrogen ($H_2$), methane, ethane, methyl acetylene, diacetylene, and $C_{3+}$ products (e.g., benzene, tars, soot, etc.). The reactor product includes components that emerge from the reactor and those that remain within the reactor, if any, as a result of pyrolysis (e.g., coke may remain in the reactor and later emerge as a portion of the combustion products). The amount of coke remaining in the reactor may be determined from a mass balance of the process. This cracking may include exposing the pyrolysis feed to high-severity operating conditions in the thermal pyrolysis reactor to produce the reactor product comprising hydrogen, ethylene and acetylene. The thermal pyrolysis reactor may be utilized at high-severity operating conditions that manage the $C_{3+}$ to $C_2U$ weight ratio ≤0.5, or ≤0.4, or ≤0.3, while the ethylene to acetylene weight ratio is ≥0.08, or ≥0.1, or ≥0.2 or ≥0.5. Further, the reactor may be operated at operating conditions that produce a reactor product that has $C_{3+}$/acetylene weight ratio of ≤0.5, or <0.45, or ≤0.4. The $C_2U$ components (e.g., acetylene and ethylene) of the reactor product may represent ≥20 wt %, or ≥50 wt %, or ≥80 wt %, or ≥90 wt % of the total $C_{2+}$ gas phase components of the reactor product. Further, the thermal pyrolysis reactor may include any of a variety of thermal pyrolysis reactors, such as a regenerative reverse flow reactor, as described in U.S. Ser. No. 11/643, 541. Other embodiments may include a thermal pyrolysis reactor, as described in U.S. Pat. No. 7,491,250, U.S. Ser. No. 61/349,464 and U.S. Patent App. Pub. Nos. 20070144940, 20070191664 and 20080142409. The thermal pyrolysis reactor may operate at operating conditions comprising a $C_{3+}$ to acetylene weight ratio ≤0.5, or ≤0.45, or <0.4. Further, the peak pyrolysis gas temperature of the thermal pyrolysis reactor may be equal to or above 1540° C., between 1450° C. and 1900° C., and/or between 1540° C. and 1800° C. The residence time for the at least a portion of the first pyrolysis feed within the thermal pyrolysis reactor may be between 0.5 second and 0.001 second. The process may involve pressures ≥3 psig (21 kPag), or ≥15 psig (103 kPag), or ≥36 psig (248 kPag), or ≥44 psig (303 kPag) or ≥103 psig (710 kPag), but may be ≤300 psig (2068 kPag), or ≤163 psig (1124 kPag), or ≤150 psig (1034 kPag). Further, for a regenerative reverse flow reactor, the pressure in the pyrolysis step may be similar or different to the pressure in the combustion step (e.g., at lower or higher pressure than the pyrolysis step).

At least a portion of the reactor product may be conducted away for storage or further processing. Optionally, one or more upgrading processes may be included in the recovery stage, as shown in blocks 208 to 216. At block 208, the composition of the reactor product or reactor effluent (e.g., acetylene concentration, hydrogen concentration and/or ethylene concentration) may be determined. The determination may be based on the composition of the pyrolysis feed provided to the pyrolysis reactor along with the operating conditions, or may be based on measurements from a measurement device.

At block 210, a hydrogen product is removed from the at least a portion of the reactor product. The removed hydrogen product may be a portion of the hydrogen in the reactor product. The removal of the hydrogen product may be adjusted based on the composition of the reactor product or may be based on a predetermined separation amount for the process. The hydrogen separation process may include different separation mechanisms along with a basic wash, for example caustic wash or amine scrubbing, to conduct the hydrogen products away from the reactor product. The hydrogen separation processes may include pressure swing adsorption, membranes, cryogenic distillation, electrochemical separation, liquid absorption, and/or liquid phase absorption and light gas desorbtion. The membrane inlet pressure or the pressure swing adsorption inlet pressure may be between 150 psig (1034 kPag) and 250 psig (1724 kPag), while the liquid phase absorption and light gas desorbtion may be performed at pressures between 50 psig (345 kPag) and 250 psig (1724 kPag). As a specific embodiment, the separation of a hydrogen product from the reactor product may be performed via a membrane, wherein the operating conditions provide a product having an acetylene mole percent concentration (e.g., an acetylene non-autodecomposition amount) within the acetylene non-autodecomposition operating window and/or may be adjusted to balance the selectivity of the acetylene into ethylene along with the acetylene non-autodecomposition amount that is within the acetylene non-autodecomposition operating window (e.g., optimized to satisfy the different factors).

The hydrogen product may be used for further processing in block 212. Specifically, the hydrogen product may be used as the hydrogen ($H_2$) containing (e.g., diluent feed into the thermal pyrolysis reactor), as a feed stripping medium, as a feed to a hydrotreater, as a fuel for the thermal pyrolysis reactor, or as a byproduct. A portion of or all of the hydrogen product may be provided as the hydrogen ($H_2$) containing.

At block 214, the remaining reactor product (e.g., the acetylene rich product) may optionally be provided to a conversion process, such as an acetylene conversion process. The remaining reactor product may be provided in the vapor phase, liquid or a mixture of vapor and liquid phase, and may be subjected to an acetylene conversion process that is performed by a catalyst. For instance, if the conversion process is an acetylene conversion process, it may include acetylene hydrogenation in an isothermal, slurry or adiabatic catalytic reactor, or other suitable conventional techniques. The catalytic reactor may employ group VI or VIII catalyst, catalyst bimetal or trimetal blends on an alumina, silica or other support, as is well known in the art.

At block 216, the conversion product, which may include ethylene, may optionally be used for further processing. The further processing may include conducting away the conversion product to storage or provide it for further processing in a purification process. The purification process may include (multistage) distillation or refrigerated distillation including a demethanator tower and $C_2$ splitter. Should additional upgrading or purification of the conversion products be desired, purification systems, such as that found in *Kirk-Othmer Encyclopedia of Chemical Technology*, 4th edition, Volume 9, John Wiley & Sons, 1996, pg. 894-899, may be used. In addition, purification systems, such as that described in *Kirk-Othmer Encyclopedia of Chemical Technology*, 4th edition, Volume 20, John Wiley & Sons, 1996, pg. 249-271, may also be used. Other examples may be found in U.S. Pat. Nos. 6,121,503; 5,960,643; 5,364,915; 5,238,892; 5,280,074; 5,288,473; 5,102,841; 4,956,426; 4,508,842; and EP Patent No. 0612753; and EP Patent No. 0012147.

Optionally, the upgraded product is conducted away for storage or for further processing, such as conversion into polyethylene. This may involve ethylene polymerization, which may include both the gas phase and solution polymerization methods, which conventional processes may be employed in the practice of the present techniques. As an example, U.S. Pat. Nos. 6,822,057; 7,045,583; 7,354,979 and 7,728,084 describe different ethylene polymerization processes that may be utilized. Also, the conversion product, such as an ethylene product, may be provided for other processes or used commercially as a final product. These processes may include generating ethylene glycol or other products. As an example, the ethylene stream may be treated, separated and polymerized to form plastic compositions, which may include polyolefins, particularly polyethylene. Any conventional process for forming polyethylene may be used, while catalytic processes are preferred. Particularly preferred are metallocene, Ziegler/Natta, aluminum oxide and acid catalytic systems. Examples may include U.S. Pat. Nos. 3,258,455; 3,305,538; 3,364,190; 5,892,079; 4,659,685; 4,076,698; 3,645,992; 4,302,565; and 4,243,691. In general, these methods involve contacting the ethylene product with a polyolefin-forming catalyst at a pressure and temperature effective to form the polyolefin product.

Beneficially, the proposed process provides various enhancements over previous techniques. For instance, by using high-severity conditions (e.g., higher temperatures) in the pyrolysis stage of the process, the present techniques may enhance $C_2$ selectivity. That is, the pyrolysis stage may crack the pyrolysis feed at residence times that are lower than other lower temperature processes. As a result, the pyrolysis feed is more efficiently cracked and the reactor size may be smaller (e.g., less capital expense and more efficient).

Further still, by managing the hydrogen content of the thermal pyrolysis reactor, different hydrocarbon feeds having low hydrogen content may be utilized by the process. That is, the hydrocarbon feed that is changed into the pyrolysis feed may be derived from a broader range of hydrocarbon feeds with lower hydrogen contents (e.g., heavy aromatic gas oils, atmospheric resids and tars). These feeds may be combined with higher hydrocarbon feeds, such as methane, which do not typically react in at low-severity conditions or react to lower value products. Thus, the high-severity conditions as provided in the present process may be used to convert at high levels the hydrocarbon feed along with the second hydrocarbon feed into valuable $C_2$ products. As such, the process may utilize a broad range of hydrocarbon feeds that foul or are unreactive in other process. In addition, managing the hydrogen content and/or parameter of the reactor feed may be used to control the levels of excess hydrogen production. Excess hydrogen production can be minimized by using a higher level of lower hydrogen content hydrocarbon feed or maximized by using a higher level of a hydrogen rich hydrocarbon feed. For example, excess hydrogen can be minimized by use of a lower setting for the hydrocarbon hydrogen level target (HHCT), such as between 12% and 20%, or between 14% and 18%. In another example, excess hydrogen can be maximized by use of a higher setting for the hydrocarbon hydrogen level target (HHCT), such as between 16% and 24%, or between 18% and 22%.

Further, the process may optionally involve other processing steps in the preparation stage and recovery stage. In the preparation stage, various feed preparation processes may be used to form the pyrolysis feed. For example, the feed preparation processes optionally include removal of impurities or contaminants prior to cracking. The feed preparation processes may include one or more of water removal units, acid gas removal units (e.g., caustic or amine treater units), dehydration units (e.g., glycol units), nitrogen removal units, demetalation, visbreaking, coking and/or vapor/liquid separators. The impurities or contaminants, which may include one or more of carbon dioxide, carbon monoxide, sulfur species, oxygenates and non volatiles (e.g., metal), may be conducted away from the process.

In the recovery stage, various recovery processes may be used to manage the reactor product. For example, between blocks 206 and 210, the reactor product may be compressed or may be subjected to a product removal process. The separation processes may remove one or more bottom products comprising liquids or solids, such as higher boiling point materials (e.g., contaminates, solids or impurities) from the $C_2U$ in reactor product. The separation process may include a tar and/or solid removal process, compression, adsorption, distillation, washing, and drying of the reactor product, and/or any combination of one or more of these processes. The compression may include compressors that operate at outlet pressures pressure from 50 psig (345 kPag) to 400 psig (2758 kPag), or more preferably from 150 psig (1034 kPag) to 300 psig (2068 kPag). The use of compressors depends upon the operating pressure of the thermal pyrolysis reactor.

Further, as noted above, the hydrogen separation process may result in an acetylene-rich product or stream and an acetylene-lean product or stream (e.g., hydrogen product), which may involve separating different products from the reactor product in the recovery stage after block 206. For instance, the acetylene-rich product may include ≥50 wt % of the acetylene from the reactor product, ≥70 wt % of the acetylene from the reactor product, ≥85 wt % of the acetylene from the reactor product, or even ≥95 wt % of the acetylene from the reactor product. The acetylene-lean product may include from 0 wt % to the remaining portion of the acetylene that is not in the acetylene-rich product.

As part of this separation process, the reactor product may pass through one or more separations to form other products, such as a light gas separation or a heavy separation in addition to the hydrogen product. For instance, after block 206, different light gas products (e.g., a portion of the light gas in the reactor product other than hydrogen) may be separated as light gas products and the remaining reactor product may form an acetylene-rich product. The light gas separation process may include different separation mechanisms along with a basic wash, for example caustic wash or amine scrubbing, to conduct the light gas products away from the reactor product. For other embodiments, the light gas separation mechanisms may include pressure swing adsorption, membranes and/or cryogenic distillation, electrochemical separation and liquid absorption. The light gas separation mechanisms may be used to separate carbon monoxide, methane, nitrogen or other light gases. The light gas products, such as methane, separated from the remaining portion of the reactor product may be used in combination with or as an addition to the diluent feed, as a fuel for the thermal pyrolysis reactor, or as a byproduct. The light gases may contain a fraction of the methane separated from the reactor product or cracked stock. Further, in some embodiments, the light gas separation may include additional stages or units to remove one or more of carbon dioxide ($CO_2$), hydrogen sulfide ($H_2S$), and water ($H_2O$) but also may include other reactive impurities. In particular, carbon dioxide and hydrogen sulfide, if present, may be removed by washing the stream with a solution of alkali or a salt of an amine or organoamine. If water is present, it may be removed by a methanol treatment, such as described in Belgian Patent No. 722,895. Other methods for removing water are adsorption and extraction by diethylene glycol. Various exemplary embodiments of this process are described further below.

Optionally, after block 206 but before block 212, a heavy product separation process may conduct away a product of condensables from the reactor product. The condensables may include vaporized liquids that condense, such as benzene, or are separated via cooled separations for example, adsorption, vapor liquid separators, flash drums, etc. Certain exemplary embodiments of this process are described further below in FIGS. 3 to 4.

Figure 3:
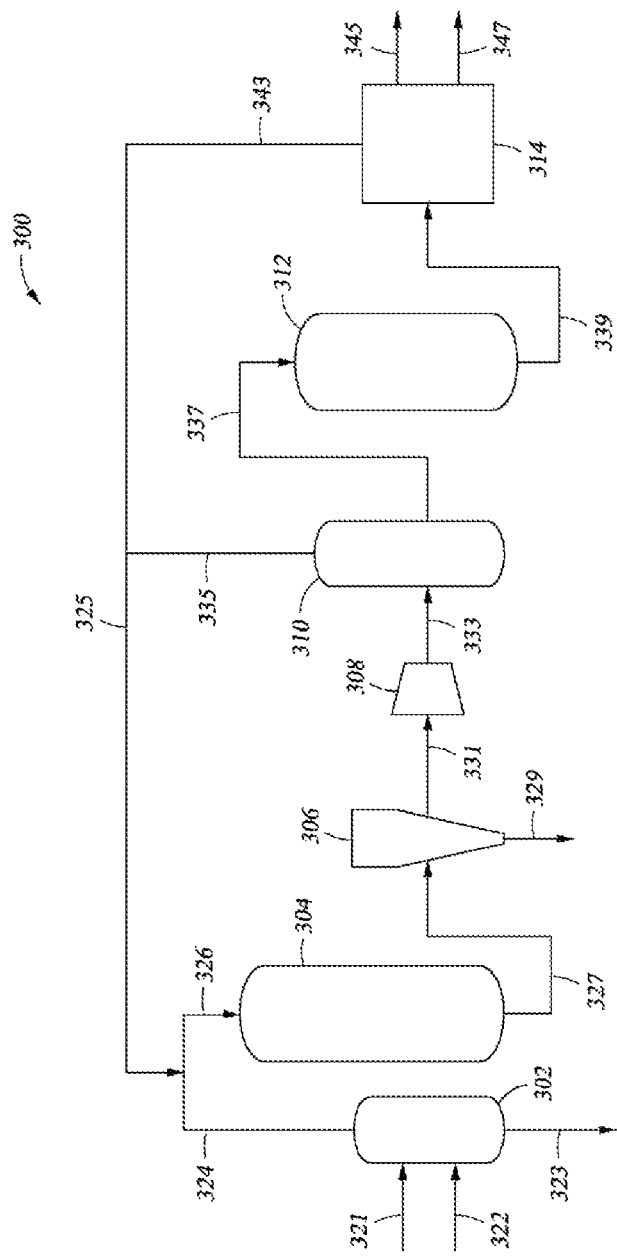
FIG. 3 is a simplified diagrammatic illustration of an exemplary process for converting a hydrocarbon feed into polyolefins in accordance with an embodiment of the present techniques.

FIG. 3 is a simplified diagrammatic illustration 300 of an exemplary process for converting hydrocarbon-containing feedstock to conversion product in accordance with an embodiment of the present techniques. In this illustration 300, a particular configuration of unit operations (i.e. units) are coupled together to convert a hydrocarbon-containing feedstock to a product, such as polyethylene or polypropylene. These units may include a feed separation unit 302, a thermal pyrolysis reactor 304, a solid removal unit 306, a compressor 308, a hydrogen separation unit 310, a converter 312 and an upgrading unit 314. In particular for this configuration, the feed preparation stage may include the feed separation unit 302 the cracking stage may include the thermal pyrolysis reactor 304; and the recovery stage may include the solid removal unit 306, the compressor 308, the hydrogen separation unit 310, the converter 312 and the upgrading unit 314. The process will now be explained in more detail.

A hydrocarbon-containing feedstock is provided via line 321 to the feed separation unit 302. The hydrocarbon-containing feedstock may be a hydrocarbon feed having a hydrogen content level ≤20 wt %, ≤16 wt %, ≤14 wt %, or ≤12 wt % of the hydrocarbon-containing feedstock or may specifically be a low hydrogen content feed, which may include non-volatiles, such as crude, atmospheric resid, vacuum resid, and/or other streams containing asphaltenes, for example. The hydrocarbon feedstock can comprise, e.g., ≥10.0 wt. % hydrocarbon, based on the weight of the hydrocarbon feedstock, e.g., ≥50.0 wt. %, such as ≥75.0 wt. %. In at least one embodiment, the hydrocarbon-containing feedstock may include non-volatiles, which are materials that are not in the gas phase (i.e. are components that are in the liquid or solid phase) at the temperature, pressure and composition conditions of the inlet to the pyrolysis reactor. The feed separation unit 302 may be used to separate the hydrocarbon-containing feedstock into a vapor product which is the first hydrocarbon feed and a bottoms product (e.g., solid/liquid product) that may contain a substantially portion or all of the non-volatile content of the hydrocarbon-containing feedstock. Examples of equipment suitable for separating the vapor product from the bottoms product include a knockout drum (e.g., substantially any vapor-liquid separator), a flash drum, distillation column/unit, flash drum having a heating means within the drum, a knockout drum having heating means within the knock-out drum, and combinations thereof. During separation, the temperature of the feed separation unit 302 is maintained between 50° C. to 750° C. or preferably 100° C. to 515° C., which may be adjusted to control the separation level within the feed separation unit 302. Depending on the hydrocarbon-containing feedstock, the vapor product may be readily separated from the remaining non-volatiles. Without separation, the non-volatiles removed as bottoms product remain in the hydrocarbon-containing feedstock as part of the first hydrocarbon feed, and may foul downstream lines or units. The bottoms product, which may include non-volatiles, may be withdrawn or removed from the feed separation unit 302 as a bottoms product or stream via line 323, which may be further processed or utilized for fuel for the thermal pyrolysis reactor 304 or other units. The vapor product, which is the reactor feed, may be withdrawn from the feed separation unit 302 as an overhead stream via line 324. Non-combustible non-volatiles (e.g., ash; ASTM D-189) are preferably limited to ≤2 parts per million weight (ppmw) on reactor feed, more preferably ≤1 ppmw. Combustible non-volatiles (e.g., tar, asphaltenes, ASTM D-6560) may be present at concentrations below 5% of the reactor feed, preferably at concentrations below 1%, more preferably at concentrations below 100 ppmw, and most preferably at concentrations below 10 ppmw of the total feed to the pyrolysis reactor, as long as the presence of the combustible non-volatiles do not result in excessive (e.g., ≥2 or ≥1 ppmw) concentrations of non-combustible non-volatiles. Carbon and hydrogen compositions as well as weight-based rate of the first hydrocarbon feed may be measured, or may be calculated via material balance on the feed separation unit. For example, if the weight-based rate of hydrocarbon-containing feedstock is 1000 kg/hr and the weight-based rate of solid/liquid product is 100 kg/hr, then the weight-based rate of first hydrocarbon feed may be calculated by difference as 900 kg/hr. Similarly, if the hydrocarbon-containing feedstock has a measured hydrogen parameter of 12 wt % and the solid/liquid product has a measured hydrogen parameter of 6%, then the hydrogen parameter of the first hydrocarbon feed may be calculated by hydrogen mass balance as (1000*12−100*6)/900=12.67%. Thus, in addition to protecting the pyrolysis reactor from potentially detrimental effects of non-volatiles in the feed, the feed separation unit 302 contributes to the control and management of hydrogen in the pyrolysis reactor and process system. As a first example, the hydrocarbon feed may comprise crude oil and crude oil components. As a second example, the pyrolysis feed may comprise substantially methane (e.g., ≥50 wt %, ≥75 wt %, or ≥90 wt % of the pyrolysis feed).

Along with the hydrocarbon-containing feedstock, a second hydrocarbon feed may be provided to the feed separation unit 302 via line 322. The second hydrocarbon feed may be derived from or may include another hydrocarbon feed having a higher hydrogen content than the first hydrocarbon feed, such as methane or methane combined with other components. The second hydrocarbon feed preferably contains no non-volatiles (e.g., is preferably volatile), and more preferably has a hydrogen parameter above 16 wt %, and may be used to increase the hydrogen parameter of the first hydrocarbon feed to form a reactor feed, which has a hydrogen parameter that is higher than the first hydrocarbon feed. As noted above, the amount of second hydrocarbon feed provided to the feed separation unit 302 may be based on a determined hydrogen content and/or parameter level, which may be based on obtained information about the first and second hydrocarbon feed or a measured hydrogen amount in the first and second hydrocarbon feed. A hydrogen measurement device, which may include nuclear magnetic resonance spectrometer (NMR), gas chromatograph (GC) or specific gravity/boiling curve analyzer may be configured to measure the hydrogen content of the feeds, feedstock, and/or bottoms product. The second hydrocarbon feed may be used to facilitate the separation in the feed separation unit 302, for example by reducing stream viscosity or by providing additional vapor flow to strip volatiles out of the feedstock and into the vapor phase. The second hydrocarbon feed is also used to adjust reactor and pyrolysis feed hydrogen parameter, as discussed below.

The reactor feed in line 324 may be combined with a hydrogen ($H_2$) containing stream, which may be a portion of the hydrogen product in line 325, to form the pyrolysis feed in line 326 that is provided to the thermal pyrolysis reactor 304. The hydrogen ($H_2$) containing stream may be added to the reactor feed by mixing the feed into the stream in line 324 to form a combined stream in line 326. Alternately (not shown on FIG. 3), some portion of the hydrogen ($H_2$) containing stream may be combined with the second hydrocarbon feed before that feed's introduction into the feed separating unit 302 and/or may be added directly to the feed separating unit 302. Regardless, the pyrolysis feed may include the three streams (e.g., the first and second hydrocarbon feeds and the hydrogen ($H_2$) containing stream). Furthermore, the first hydrocarbon feed may not ever be present as an isolated stream. That is, the first hydrocarbon feed is the material that has been vaporized out of the hydrocarbon-containing feedstock; may be calculated as shown above based on the flows and composition of the hydrocarbon-containing feedstock provided via line 321 and the bottoms product 323; but may only be present (in lines 324 and 326) as a vapor-phase mixture with the second hydrocarbon feed and optionally portions of the hydrogen ($H_2$) containing stream.

The hydrogen ($H_2$) containing stream may be used to further adjust the hydrogen parameter of the reactor feed to form the pyrolysis feed having a hydrogen parameter above a certain threshold, such as a total atomic hydrogen to carbon ratio target (HCRT). The second hydrocarbon feed may be used to further adjust the hydrogen parameter of the reactor feed to have a hydrogen parameter at or above a certain threshold or certain target, such as a hydrocarbon hydrogen target (HHCT). Used together, the flows and properties of all three components of the pyrolysis feed (the first and second hydrocarbon feed and the hydrogen ($H_2$) containing stream) may be employed to simultaneously achieve both the total atomic hydrogen to carbon ratio target (HCRT) and the hydrocarbon hydrogen target (HHCT), for example using equations e1 and e2 described above. Computed flows and properties for the first hydrocarbon feed (based on calculated or measures flows and properties of the hydrocarbon-containing feedstock and bottoms product) may be used in equations e1 and e2. The total atomic hydrogen to carbon ratio target level may include a specific target level, such as between 3 and 15, between 5 and 12, or between 6 and 9. The hydrocarbon hydrogen target may include a specific target level, such as a hydrogen parameter between 14 wt % and 25 wt %, or between 12 wt % and 18 wt %, between 15 wt % and 20 wt %, or between 16 wt % and 18 wt %.

The hydrogen management approach may be used in several ways. For example, there may be a certain amount (weight based rate) of hydrocarbon-containing feedstock that is desired to be cracked, and the equations e1 and e2 can be used to compute how much added second hydrocarbon feed and hydrogen ($H_2$) containing feed should be added to reach some pyrolysis reactor target that may crack the volatile portion of the hydrocarbon-containing feedstock within the known performance guidelines of the pyrolysis unit. For example, it may be known that the pyrolysis feed should be at a minimum hydrocarbon hydrogen target and total atomic hydrogen to carbon ratio target to achieve the desired conversion, $C_{3+}/C_2U$ weight ratios and E/A weight ratios. Equations e1 and e2 are then used to compute how much of second hydrocarbon feed and hydrogen ($H_2$) containing feed have to be added to reach the desired target levels.

As a second example, the hydrogen management approach may be used to manage the amount of surplus hydrogen that is produced in the process. For example, it may be desired to crack a second hydrocarbon feed having high hydrogen content, but desired not to produce a large excess of hydrogen after accounting for other processing units needs, such as acetylene conversion. In such an example, the hydrocarbon hydrogen level target may be set at a level that results in the desired amount of excess hydrogen, such as between about 14 and 18 wt %; the hydrogen to carbon ratio target level may be set at a level required to achieve pyrolysis unit performance, such as between 6 and 9, and then equations e1 and e2 may be used to compute how much of the first hydrocarbon feed and the hydrogen ($H_2$) containing feed should be added to reach the desired target levels. Regardless of hydrogen management approach for the pyrolysis reactor, the choices that are made in hydrocarbon hydrogen target and total atomic hydrogen to carbon ratio target directly influence the level of hydrogen ($H_2$) gas present in the pyrolysis product (for example see impact of HCRT shown in Table 2 and 3). Thus, levels for hydrocarbon hydrogen target and total hydrogen to carbon ratio target impact the hydrogen management choices and strategies that may be used for product separation unit 310, as discussed below.

The thermal pyrolysis reactor 304, as noted above, may include a regenerative reverse flow reactor or other suitable reactor, as noted above in the discussions above and further below. Accordingly, the thermal pyrolysis reactor 304 may have different piping configurations to provide combustion feed (e.g., fuel) and the pyrolysis feed separately, depending on the specific configuration.

The reactor effluent or the reactor product from the thermal pyrolysis reactor 304 is conducted away via line 327 to the solid removal unit 306 and other recovery stage units. The solid removal unit 306 may include water scrubbing, oil scrubbing, cyclone separation, electrostatic separation, filtration, and/or moving bed adsorption. As may be appreciated, each of these systems may be combined together in one or more units to overcome certain limitations within the system. For instance, water scrubbing is effective to remove solid carbon black and other solids, but it limits the recovery of heat in the effluent. Oil scrubbing may be utilized for heat recovery, but it may present problems with fouling and emulsion formation. Cyclone separation may be limited to remove solid carbon, but not other smaller or fine solids. Electrostatic separation may have problems with clogging and short-circuiting due to carbon deposit buildup. Adsorption and filtration are limited to handling small amounts of solids and may be problematic for larger amounts of solids. As a result, one or more of these techniques may be coupled together in series to provide the separation. The solid-liquid phase of the reactor product may be conducted away from solid removal unit 306 as a bottoms product, which may be a bottoms stream, via line 329. The bottoms product may include carbon black, soots, and/or heavy aromatic oils and/or tars. If the bottoms product is "dry", it may be handled via filtration or electrostatic separation; if sticky or wet, it may be better handled via washing (oil or water) or absorption. The bottoms product may be recycled to the thermal pyrolysis reactor or may be used as a fuel (in the reactor or process). The remaining portion of the reactor effluent or reactor product may be withdrawn from solid removal unit 306 as an overhead stream via line 331 and passed to the compressor 308.

The compressor 308 may receive the vapor product from the solid removal unit 306 and compress the product and provide the compressed product via 333 to the hydrogen separation unit 310. The compressor 308 may compress to the vapor product to a pressure from 50 psig (345 kPag) to 400 psig (2758 kPag), or more preferably from 150 psig (1034 kPag) to 300 psig (2068 kPag). For other embodiments, the pressure may be adjusted for hydrogen ($H_2$) removal (e.g., pressure swing adsorption, hydrogen membrane and/or cryogenic distillation, electrochemical separation) and acetylene hydrogenation.

Once compressed, different products, such as hydrogen products may be separated from the reactor product in the product separation unit 310. Specifically, the process may include a hydrogen removal step that passes a hydrogen product via line 335. The product separation unit 310 may include the different units (not shown) along with caustic wash, amine scrubber and/or other treatments. Other separation processes, similar to those discussed above, may be combined with the product separation unit 310, which may include steps to remove different products (e.g., $CO_2$, $H_2S$ and/or $H_2O$) from the process. The reactor product may be recovered from the product separation unit 310 as via line 337 and passed to the converter 312, while the impurities may be withdrawn as products via line (not shown), which may be further processed for the different impurities. The reactor product in line 337 may be combined with other diluents and/or recycle products (not shown) and may be referred to as the conversion reactor feed, which may be Y mole % of acetylene per mole of the total stream 337.

Optionally, the converter 312 may receive the reactor product (e.g., $C_2U$ stream or products comprising acetylene and ethylene) from the product separation unit 310. If the converter is an acetylene converter (A/C), it may selectively hydrogenate the acetylene to ethylene without significantly hydrogenating the ethylene to ethane. The acetylene converter may include a hydrogenation unit, and optionally may further include a compressor, stream recycle components, desorption unit and/or separation unit.

In one embodiment, a conversion product of ≥50 wt % of ethylene may be conducted away from the converter 312 to storage or for further processing. As an example, the conversion product may be passed to the upgrading unit 314 via line 339. The upgrading unit may include a purification unit, which may include a demethanator tower (to remove $H_2$, $CH_4$, $N_2$ and CO) and a $C_2$ splitter to remove ethane and upgrade ethylene to polymer grade ethylene. The purification unit may also include $C_2$ or $C_3$ refrigeration train, compression and additional distillation towers. This upgrading unit 314 may separate the conversion product from the converter 312 into one or more products and an upgraded product, such as an ethylene stream. The one or more products, which are provided to line 347, may include different light gas products (e.g., carbon monoxide, nitrogen, methane, and the like) or heavier products (e.g., ethane and $C_{3+}$ streams). A portion of the recovered products (e.g., hydrogen and/or methane) may be recycled for processing again in the thermal pyrolysis reactor 304 via line 343. Further, if the upgraded product is an ethylene stream, it may be provided to the ethylene polymerization unit (not shown) via line 345. The ethylene polymerization unit may be a catalytic reactor, which may include a gas catalyst and/or a liquid catalyst. The process may involve a catalyst, solvent and the feed stream, as discussed above.

In this embodiment, the reactor product may comprise hydrogen, ethylene, and X mole % acetylene per mole of reactor product. This may include the stream within the lines 327, 331 and 333, under conditions including subjecting the reactor product to solid separation and compression. Then, the reactor product may be subjected to hydrogen separation in a hydrogen separation unit 310. The portion of the reactor product in line 337, which may be referred to as the conversion reactor feed, may have Y mole % of acetylene per mole of the portion of the reactor product and have a hydrogen to acetylene molar ratio in the range of from 1.0 and 10.0. The portion of the reactor product may then react with a catalyst in a converter operated in at least partially in the vapor phase to form a conversion product comprising 0.0 mole % to Z mole % acetylene per mole of the conversion product, wherein Y>Z. To maintain proper operating conditions in this process, X<90.0% of a first acetylene non-autodecomposition amount, and Y<90.0% or <89.0% of a second acetylene non-autodecomposition amount.

In some embodiments, a portion of the acetylene in the reactor product may optionally be combined with other process steps to form other products. In particular, the portion of the acetylene may be an intermediate product or precursor in a process within a chemical plant, in route to other preferred products, such as vinyl esters, ethylene, acetaldehyde, propanal, propanol, acrylic acid, and/or the like.

Figure 4:
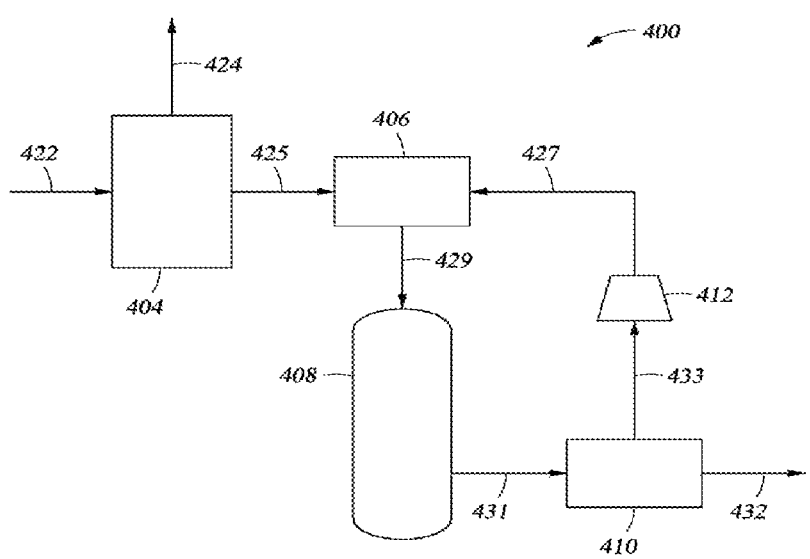
FIG. 4 is a simplified diagrammatic illustration of an exemplary recovery configuration comprising a separation unit and converter in accordance with an embodiment of the present techniques.

FIG. 4 is a simplified diagrammatic illustration of an exemplary recovery configuration 400. In this illustration 400, a particular configuration of units are coupled together to convert a reactor product into an acetylene rich stream and a hydrogen product. The hydrogen separation unit 404, a mixer 406 a converter 408, a splitter 410 and a compressor 412. This process may include units similar to those above and may be coupled to the units described above in FIGS. 2 to 3. The process will now be explained in more detail.

A reactor product is provided via line 422 to the hydrogen separation unit 404. The reactor product, which may be reactor effluent from a pyrolysis reactor (e.g., one or more of the pyrolysis reactors noted above), may include ethylene, hydrogen and acetylene. The hydrogen separation unit 404, which may be one embodiment of the product separation unit 310 of FIG. 3, may include different separation mechanisms to conduct the hydrogen product away from the reactor product. Similar to the discussion above, the hydrogen separation unit 404 may be coupled with other units (not shown) to remove impurities or separate other products. The remaining reactor product (e.g., acetylene rich product) may be recovered from the hydrogen separation unit 404 via line 425 and provided to a mixing unit 406, while the hydrogen product may be provided via line 424 for further processing, as noted above. Specifically, the hydrogen product may be used as the hydrogen ($H_2$) containing stream (e.g., diluent feed into the thermal pyrolysis reactor), as a feed stripping medium, as a feed to a hydrotreater, as a fuel for the thermal pyrolysis reactor, or as a byproduct. The hydrogen separation mechanisms may include pressure swing adsorption, membranes and/or cryogenic distillation, and/or electrochemical separation. As a specific embodiment, the separating a hydrogen product from the reactor product that may involve providing an acetylene rich product having an acetylene to diluent molar ratio within the acetylene non-autodecomposition operating window.

The mixing unit 406 may combine the acetylene along with a converter recycle product provided via line 427, which may include ethylene or other suitable products. The mixing unit 406 may include a manifold, sparger or other suitable unit that combines the converter recycle product with the acetylene-rich product. The converter recycle product may be used to control the acetylene level within a preferred range and/or to control the acetylene to ethylene exotherm and selectivity. The mixture is then provided via line 429 to a converter 408, which may be any suitable converter. The mixture in line 429 may be referred to as the conversion reactor feed, which may be Y mole % of acetylene per mole of the total stream 429.

The converter 408 may receive the reactor product (e.g., acetylene-rich product or $C_2U$ products comprising acetylene and ethylene) from the mixing unit 406. If the converter 408 is an acetylene converter (A/C), it may selectively hydrogenate the acetylene to ethylene without significantly hydrogenating the ethylene to ethane and/or without producing significant levels of green oil. The acetylene converter may operate at feed levels ranging from 0.5 to 30 mol % acetylene, or ranging from 0.5 to 15 mol % acetylene. The acetylene converter may operate at pressures from 32 psig (221 kPag) to 400 psig (2758 kPag), at inlet temperatures of 50° C. to 300° C. and may utilize catalyst comprising group VI or VIII catalysts. Conversion levels for the hydrotreater may range from 70 wt % to 100 wt % acetylene conversion and may have selectivity to ethylene from 70 wt % to as high as 98 wt % ethylene. The acetylene converter may include an optional finishing acetylene converter to convert remaining levels of acetylene at 100 wt % conversion of the acetylene. This finishing acetylene converter may be in fluid communication with the one or more units, such as the acetylene converter or other units downstream of the acetylene converter. The acetylene converter may include a hydrogenation unit.

The conversion product from the converter 408 may be provided via 431 to a splitter 410. The splitter 410 may separate or divide a portion of the conversion product into a converter recycle product, while the remaining conversion product may be conducted away via line 432 for further processing, as noted above. The splitter 410 may be a joint in the pipes or lines, a flow regulation unit, a manifold or other suitable unit. For instance, the remaining conversion product may be provided to an upgrading unit, such as upgrading unit 314 of FIG. 3.

The converter recycle product may be passed via line 433 to an optional compressor 412. The compressor 412 may be similar to the compressors noted above. The compressor may compress the converter recycle product to have a pressure that matches the inlet pressure. These pressures may include of 32 psig (221 kPag) to 400 psig (2758 kPag) or more preferably from 100 psig (689 kPag) to 300 psig (2068 kPag). Once compressed the converter recycle product may be provided to the mixer 406 via line 427.

This process may utilize readily available vapor, liquid or mixed phase acetylene converter technology by maintaining the $H_2$ and acetylene levels within the acetylene non-autodecomposition operating window. By selectively removing $H_2$ gas with a membrane, the stream pressure of the reactor product is maintained and the selectivity of conversion of acetylenes to olefins in the converter is improved. As discussed above, lower $H_2$ to acetylene ratios may improve selectivity to ethylene and may reduce ethane with commercially available raw gas or front end converters and catalysts. That is, if an excess of hydrogen gas is removed in the reactor product that contains high levels of acetylene (e.g., ≥5 mol % as expected for a high severity pyrolysis reactor), the risk of acetylene detonation or autodecomposition is increased. Further, this process avoids the need for adsorption solvents to maintain acetylene in a dilute form (e.g., maintain the acetylene in liquid phase) for high levels of acetylene. Finally, this example offers the recycle of converter product (primarily ethylene) to further control the molar acetylene level, to maintain high acetylene selectivity and avoid an exothermic catalyst runaway.

In this embodiment, the reactor product may comprise hydrogen, ethylene, and X mole % acetylene per mole of reactor product. This may include the reactor product in lines 422 or 425, which may vary at the respective locations. The reactor product may be combined with a recycle product in mixing unit 406. As such, the portion of the reactor product (e.g., the conversion reactor feed, which may include recycle streams and/or diluents) in line 429 may have Y mole % of acetylene per mole of the portion of the reactor product and have a hydrogen to acetylene molar ratio in the range of from 1.0 and 10.0. The portion of the reactor may then react with a catalyst in a converter operated in at least partially in the vapor phase to form a conversion product comprising 0.0 mole % to Z mole % acetylene per mole of the conversion product, wherein Y>Z. To maintain proper operating conditions in this process, X<90.0% of a first acetylene non-autodecomposition amount, and Y<90.0% or <89.0% of a second acetylene non-autodecomposition amount.

As a specific example, the hydrogen separation unit 404 may be a hydrogen membrane, while the converter 408 may be an acetylene converter. The reactor product may include 84 mol % of $H_2$, 8 mol % of $C_1$, 6 mol % of acetylene, 1 mol % of ethylene and 1 mol % of $C_{2+}$, which may at a temperature of 52° C. and at a pressure of 183 psig (1263 kPag). A hydrogen membrane advantageously provides the retentate at or near membrane feed pressure to preserve pressure required for the acetylene converter, but reduces the pressure of the permeate (hydrogen). For a typical membrane operation, the hydrogen membrane may be configured to remove a portion of the hydrogen product that has hydrogen purity of ≥90 wt % of the hydrogen product, ≥95 wt % of the hydrogen. The hydrogen product may include 99 mol % of $H_2$, which may be at a temperature of 52° C. and at a pressure of 30 psig (207 kPag). The acetylene rich product may include 43 mol % of $H_2$, 28 mol % $C_1$, 23 mol % acetylene, 5 mol % ethylene and 1 mol % $C_{2+}$, which may at a temperature of 52° C. and at a pressure of 183 psig (1262 kPag). At the mixing unit 406, the acetylene rich product may be combined with a converter recycle product that includes 21 mol % of $H_2$, 40 mol % $C_1$, 0 mol % acetylene, 36 mol % ethylene and 3 mol % $C_{2+}$, which may be at a temperature of 52° C. and at a pressure of 186 psig (1282 kPag). Once mixed, the mixture from the mixing unit 306 may include 25 mol % of $H_2$, 37 mol % of $C_1$, 3 mol % of acetylene, 31 mol % ethylene and 4 mol % ethane and $C_{3+}$, which may at a temperature of 52° C. and at a pressure of 183 psig (1262 kPag).

Accordingly, in one or more of the embodiments, a control mechanism may be utilized to manage the hydrogen through the process from the hydrocarbon feed into the final product. The control mechanism may include a process control unit coupled to one or more measurement devices that measure operational data (e.g., temperature, hydrogen content, composition, pressure, and the like) and one or more control units for adjusting operational settings (e.g., amount fuel provided to the pyrolysis reactors, amount of hydrogen ($H_2$) containing stream combined with the reactor feed, amount of second hydrocarbon feed combined with the hydrocarbon feed, pressure for the different units or the like). The process control unit, measurement devices and/or control units may communicate with each other via a physical and/or wireless means.

The process control unit may include a computer system along with one or more monitors and input/output components. The computer system may include memory to store sets of instructions and operational data and a processor to execute the instructions and access the operational data. In this system, operational settings may be adjusted to manage or refine the processing of the feeds within the system and to manage the operating parameters. For instance, operational settings may be adjusted in the system to further refine the amount of second hydrocarbon feed combined with the hydrocarbon feed in the feed separation unit 302. These operating parameters may include monitored values, which are stored as operational data in the memory, and utilized by the processor in executing one or more sets of instructions to monitor the hydrogen content and flow of hydrocarbons through the system, to adjust operational settings, and other similar operations.

Along with the process control unit, the control mechanism may include different types of measurement devices, such as a temperature measurement device and a composition measurement device that can measure hydrogen and carbon content, ethylene content and/or acetylene content. The temperature measurement device, which may include a thermocouple, may be configured to measure the temperature of the hydrocarbon feed prior to the feed separation (e.g., prior to feed separation unit 302) and/or the temperature of the reactor feed from the feed separation (e.g., prior to feed separation unit 302). The composition measurement device, which may include a nuclear magnetic resonance spectrometer (NMR), gas chromatograph (GC), specific gravity/boiling curve analyzer or a offline correlation of specific gravity and simulated distillation, may be configured to measure the hydrogen and carbon content of the hydrocarbon feed prior to the feed separation (e.g., prior to feed separation unit 302), the hydrogen content of the reactor feed before the combining of the hydrogen ($H_2$) containing stream with the reactor feed (e.g., after the feed separation unit 302 in line 324), the hydrogen and carbon content of the reactor product prior to hydrogen separation (e.g., prior to product separation unit 310 or hydrogen separation unit 404) and/or the hydrogen and carbon content of the remaining reactor product prior to the converter (e.g., prior to converter 312 and/or converter 408).

The one or more control units may include different control units to adjust different operational settings. For example, a second hydrocarbon feed control unit may be utilized or configured to adjust the amount of the second hydrocarbon feed mixed with the first hydrocarbon feed (e.g., in the feed separation unit 302). That is, the second hydrocarbon feed control unit may include one or more valves (e.g., a valve on line 322) to adjust the flow rate being mixed with the first hydrocarbon feed. Also, a reactor hydrogen control unit may be utilized and configured to adjust the amount of a hydrogen ($H_2$) containing stream mixed with the reactor feed prior to being passed to the thermal pyrolysis reactor. That is, the reactor hydrogen control unit may include one or more valves (e.g., a valve on line 325) or a line diverting the hydrogen product to adjust the flow rate of the hydrogen ($H_2$) containing stream being mixed with the reactor feed. Further still, an acetylene hydrogen control unit may be utilized and configured to adjust the amount of hydrogen removed as a hydrogen product from the reactor product. That is, the acetylene hydrogen control unit may include one or more valves (e.g., a valve on line 335 or line 343 or on line 624) to adjust the pressure of the reactor product or hydrogen product, which adjusts the amount of hydrogen product being separated from the reactor product.

The present techniques may monitor certain operating parameters and adjust operational settings to provide an enhanced process. For instance, the control mechanism may include one or more composition measurement device configured to measure hydrogen and carbon content of the feeds and streams that are combined to form a pyrolysis feed prior to the thermal pyrolysis reactor. The control mechanism may also include a process control unit having a set of instructions stored in memory and accessed via a processor, which are configured to (i) receive operational parameters (e.g., hydrogen parameter or composition of the feeds and streams) from the one or more composition measurement device(s) coupled to line 324; (ii) to calculate the amount of second hydrocarbon streams and/or amount of hydrogen ($H_2$) containing stream to be supplied to the pyrolysis feed via line 325; and (iii) provide an indication to a reactor hydrogen control unit to adjustment to the flow rate of the feeds and streams based on the determined flow rate. The adjustment of flow rates for the second hydrocarbon streams and hydrogen ($H_2$) containing stream may be based on equations (e1) and (e2) discussed above.

As another example, the control mechanism may include composition measurement device configured to measure composition (e.g., hydrogen content, ethylene content and/or acetylene content) of the reactor product prior to the product separation unit 310. The control mechanism may also include a process control unit having a set of instructions stored in memory and accessed via a processor, which are configured to (i) receive operational parameters (e.g., hydrogen parameter, ethylene content, acetylene content and/or composition of the reactor product) from the composition measurement device coupled to line 333; (ii) to calculate the amount of hydrogen product to be supplied to the reactor feed via line 325 or to calculate the amount of hydrogen product that needs to be removed from the reactor product so that the acetylene non-autodecomposition amount is within the acetylene non-autodecomposition operating window or enhance the selectivity of the converter; and (iii) provide an indication to a hydrogen control unit to adjust the flow rate of line 422 and/or 424 or the flow rate of 333 and/or 335.

Similar to the discussion above, a process control mechanism may include different configurations to manage hydrogen through the pyrolysis reactor and/or through the converter. For the pyrolysis reactors, the control mechanism may include a composition measurement device configured to measure hydrogen and carbon content of the reactor feed prior to the pyrolysis reactor 304 in line 324 or feed separation unit 302. The control mechanism may also include a process control unit having a set of instructions stored in memory and accessed via a processor, which are configured to (i) receive operational parameters (e.g., hydrogen parameter or composition of the reactor feed) from the composition measurement device; (ii) to calculate the amount of hydrogen ($H_2$) containing stream to be supplied to the reactor feed; and (iii) provide an indication to a reactor hydrogen control unit to adjustment to the flow rate of the hydrogen ($H_2$) containing stream being provided via line 325 based on the determined flow rate. Further, the process control unit may have an additional set of instructions stored in memory and accessed via a processor, which are configured to (iv) calculate the amount of hydrogen product to be removed from the reactor product at the product separation unit 310; and (v) provide an indication to a hydrogen removal control unit to adjustment to the amount of hydrogen removed from the reactor product.

As an example, the process control unit may include a set of instructions that when executed by the processor are configured to: i) obtain a weight based rate (WT1) of a first hydrocarbon feed having a carbon parameter (CHC1) and a hydrogen parameter (HHC1); ii) obtain a carbon parameter (CHC2) and a hydrogen parameter (HHC2) of a second hydrocarbon feed; iii) obtain a hydrogen gas content (HH2D) and a hydrocarbon content (HCD) of a hydrogen ($H_2$) containing stream, wherein the hydrocarbon content (HCD) has a hydrocarbon hydrogen (HHCD) and a carbon parameter (CHCD) as a weight percent of total hydrogen ($H_2$) containing stream; and iv) calculate a weight based rate (WT2) of the second hydrocarbon feed and a weight based rate (WTD) of the hydrogen ($H_2$) containing stream to achieve a predetermined hydrocarbon hydrogen target level (HHCT) and a total atomic hydrogen to carbon target ratio level (HCRT) for the pyrolysis feed. Then, the set of instructions may algebraically solve equations e1 and e2, which are noted above, to determine the weight based rate (WT2) and the weight based rate (WTD). The determined hydrocarbon hydrogen target level (HHCT) may be between 12 wt % to 25 wt %, or between 15 wt % to 20 wt %, while the total atomic hydrogen to carbon target ratio level (HCRT) may be between 3 and 15, between 5 and 12 or between 6 and 9. The weight based rate (WT2) may be between 0 wt % and 95 wt % of the combined the weight based rate (WT1) and the weight based rate (WT2).

To manage the process, the process control unit may communicate with other control units and/or measurement devices. For instance, the process control unit may adjust the flow rate of at least one of the second hydrocarbon feed or the hydrogen ($H_2$) containing stream based on one of the determined weight based rate (WT2), the weight based rate (WTD), and any combination thereof. As a specific example, the process control unit may transmit one or more signals to one or more flow control units to the adjust the amount of the second hydrocarbon feed mixed with the first hydrocarbon feed based on the calculated weight based rate (WT2) and/or adjust the amount of the hydrogen ($H_2$) containing stream mixed with the reactor feed based on the calculated weight based rate (WTD). Further, measurement devices may be utilized to measure the carbon parameter (CHC1) and the hydrogen parameter (HHC1) and provide it for storage in the memory.

As may be appreciated the process control unit, measurement devices and control units may be coupled to various equipment in the embodiments noted above. For instance, another specific configuration, the process may include a mixing unit, a thermal pyrolysis reactor and a process control unit. The mixing unit may be configured to combine a first hydrocarbon feed, a second hydrocarbon feed and a hydrogen ($H_2$) containing stream into a pyrolysis reactor, while the thermal pyrolysis reactor is configured to expose at least a portion of a pyrolysis feed to a peak pyrolysis gas temperature equal to or above 1400° C. within the thermal pyrolysis reactor to produce a reactor product comprising ethylene and acetylene. The process control unit may be in communication with the mixing unit and include a processor coupled to memory that stores a set of instructions accessible by the processor and when the set of instructions are executed by the processor, the set of instructions are configured to: i) calculate a weight based rate (WT2) of the second hydrocarbon feed; ii) calculate a weight based rate (WTD) of the hydrogen ($H_2$) containing stream, wherein the calculation of the weight based rate (WT2) and the weight based rate (WTD) are based on a weight based rate (WT1) of the first hydrocarbon feed having a carbon parameter (CHC1) and a hydrogen parameter (HHC1) and a predetermined hydrocarbon hydrogen target level (HHCT) and a total atomic hydrogen to carbon target ratio level (HCRT) for the pyrolysis feed. The set of instructions stored in the memory may further be configured to: iii) provide a weight based rate (WT1) of the first hydrocarbon feed having a carbon parameter (CHC1) and a hydrogen parameter (HHC1); provide a carbon parameter (CHC2) and a hydrogen parameter (HHC2) of the second hydrocarbon feed; iv) provide a hydrogen gas content (HH2D) and a hydrocarbon content (HCD) hydrogen ($H_2$) containing stream, wherein the hydrocarbon content (HCD) has a hydrocarbon hydrogen (HHCD) and a carbon parameter (CHCD) as a weight percent of total hydrogen ($H_2$) containing stream; and v) calculate the weight based rate (WT2) and the weight based rate (WTD) to achieve a predetermined hydrocarbon hydrogen target level (HHCT) and a total atomic hydrogen to carbon target ratio level (HCRT) for the pyrolysis feed, which may solve the equations e1 and e2; and transmit one or more flow rate signals based on one of the calculated weight based rate (WT2), the calculated weight based rate (WTD), and a combination thereof. Also, a flow control unit may be in communication with the process control unit and the mixing unit and configured to: a) receive the one or more flow rate signals; and b) adjust one of the flow rate of the second hydrocarbon feed, the flow rate of the hydrogen ($H_2$) containing stream, and any combination thereof. Further, a composition measurement device may be in communication with the process control unit and configured to: a) measure at least one of the carbon parameter (CHC1), the hydrogen parameter (HHC1), and any combination thereof and b) transmit one or more measurement signals based on the at least one of the carbon parameter (CHC1), the hydrogen parameter (HHC1), and any combination thereof.

Moreover, in addition to the control mechanisms above, the control mechanism may also include instructions and equipment to account for the converter recycle product, which may influence the amount of hydrogen removed as the hydrogen product. Accordingly, the control mechanism may include a composition measurement device coupled to one or more lines and units between the pyrolysis reactor and the mixing unit 406. The composition measurement device in communication with the process control unit may be configured to measure the composition (e.g., acetylene concentration, hydrogen concentration and/or ethylene concentration) of the reactor product prior to the converter 408. The process control unit may have having a set of instructions stored in memory and accessed via a processor, which are configured to (i) receive operational parameters (e.g., data or signals about the composition of the reactor product) from the composition measurement device; (ii) to calculate the amount of recycle converter product to be supplied to the acetylene rich product via mixing unit 406 to be an acetylene non-autodecomposition amount that is within the non-autodecomposition operating window; and (iii) provide an indication to converter recycle control unit to adjust the outlet pressure of the splitter 410 to match the inlet pressure of the converter 408.

The thermal pyrolysis reactor may include a severity threshold temperature that divides low-severity thermal pyrolysis reactors from high-severity thermal pyrolysis reactors that is defined as the lowest temperature at which the pyrolysis feed can react to make at least 10 wt % acetylene at a residence time ≤0.1 sec. The high-severity thermal pyrolysis reactor includes pyrolysis gas temperatures that are greater than the severity threshold temperature, while the low-severity thermal pyrolysis reactor include pyrolysis gas temperatures that are less than the severity threshold temperature and no pyrolysis gas temperatures that exceed the severity threshold temperature. For example, for the thermal conversion of methane at a pressure of 14.7 psig and with 2:1 molar ratio of hydrogen diluent, the threshold temperature is about 1274° C. At temperatures at or above 1274° C., yields of acetylene can exceed 10 wt % of the starting methane, at some time ≤0.1 seconds. Conversely, at temperatures below 1274° C., there are no times ≤0.1 seconds for which yields of acetylene reaches 10 wt % of the starting methane.

Although the units of FIGS. 3 to 4 are shown as respective single and separate units, each of these units can alternatively comprise a plurality of units. For example, a separation unit may include more than one knockout drums, separators, and/or flash drums. Accordingly, different embodiments may utilize different units in this manner. Further, some additional embodiments, which are discussed further below, may be utilized in these embodiments of FIGS. 2 to 4.

The thermal pyrolysis reactors of the present techniques may be operated at different temperatures based on the specific operation and process variations. The different thermal pyrolysis reactors may include specific mechanisms and processes to heat the pyrolysis feed. Accordingly, each reactor may include different means for measuring the temperature of that specific process.

As a specific example for a thermal pyrolysis reactor, the pyrolysis stream is heated by a solid material, which is heated by a combustion reaction. Usually, the solid material forms the channels that the pyrolysis stream travels through. The combustion reaction of combustion feed that heats the solid material may heat via convective and/or radiative mechanisms. In these reactors, the highest temperatures are observed in the stream that is heating the solids (e.g., combustion stream). At any location, the solid material has a temperature that is lower than that of the combustion stream from which it receives heat, while the pyrolysis stream being heated by the solid material has a temperature that is lower than the solid material. The specific temperature of the combustion stream, pyrolysis stream or solid material depends on its location within the reactor and on the configuration and/or operation of the pyrolysis reactor.

In certain thermal pyrolysis reactors (e.g., steam cracking furnace configuration), the heating and the pyrolysis process occur simultaneously, for example with a combusting stream on one side of partition (typically a wall or tubular) and the pyrolysis stream on the other side. Such reactors operate at or near steady state. The partition between the combustion feed and the pyrolysis feed has real physical dimensions and the temperature is not equal at every location. For example, on the combustion side, temperatures may be hottest near a flame region, and on the pyrolysis side temperatures increase with heat addition until some maximum temperature is reached. Steady state in these systems means that, at any given location relative to the fixed partition, temperatures remain relatively steady. However, the gases that travel through the reactor are heated and cooled by the chemistry and heat transfer that takes place in the reactor. The term "peak pyrolysis gas temperature" means the maximum temperature achieved by the bulk pyrolysis stream gases as they travel through the pyrolysis reactor (e.g., cracking region or radiant region). One skilled in the art will appreciate that temperatures immediately proximate to the partition may be higher, and may, in some infinitesimal layer, actually approach the solid temperature. However, the pyrolysis temperature referred to herein should be considered a bulk gas temperature, which is a temperature that could be measured by a device (such as a thermocouple) that is not in contact with the solid material. For example, if the gas is traveling through tubulars in a thermal pyrolysis reactor, the bulk gas temperature may be taken as the average temperature over any tubular cross-section, and the peak pyrolysis gas temperature as the highest cross-sectional-average temperature of the pyrolysis stream.

In a thermal pyrolysis regenerative reactor system, the heating and pyrolysis occur in sequential steps. First, a heating step, usually a combustion reaction or combustion step, is used to heat the solid material. Second, a pyrolysis step is carried out that absorbs heat from the solid material to effect a chemical reaction. The solid material may be in fixed orientation or in moving orientation. If moving, the solid is typically moved from a heating region to a pyrolysis region. Moving-solid systems appear to be step-wise from the perspective of the moving solid, however the gas streams may be at steady state in any absolute location, and temperatures are defined very much as discussed for thermal pyrolysis furnace-type reactors. When the solid material is in fixed orientation, a regenerative system may use valves to alternate introduction of pyrolysis and heating streams into the solid-containing region. The solid material may be designed to facilitate the process of heat addition and removal. Checker bricks, tiles and monoliths may be used as the solid materials within the reactor. Such materials form a network of passages that are used by the gases in each step to transit the region containing solid material. The heat addition step leaves a profile of temperatures in the solid material, that is, a temperature that varies along the path by which the gases transit the solid material. The shape of that profile depends on many factors, including if and where a heat release (combustion) reaction occurs, the initial temperature distribution, the duration of the heating step, the flow rate and inlet temperature of the gas stream, and the heat capacity and transfer properties of the gas and solid material. On average, the solid material is hottest at the end of the heating step. The pyrolysis step consumes heat and reduces average solid material temperature. The pyrolysis step changes the profile of temperatures in the solid material, in a way that depends on many factors, including where the heat consumption (pyrolysis) reaction occurs, the initial temperature distribution, the duration of the pyrolysis step, the flow rate and inlet temperature of the gas stream, and the heat capacity and transfer properties of the gas and solid. Fixed-solid regenerative pyrolysis reactors are not at steady state. That is, at any given location, the temperature changes. However, these reactors may be in a periodic steady state, meaning that the same cycling of temperatures occurs over and over as the reactor oscillates between heating and pyrolysis.

In a reverse-flow regenerative system, a reversal occurs in the direction of transit of the gases through the region that contains the solid material, and this reversal occurs in between the heating and pyrolysis steps. In some embodiments, reversal occurs between every step, and in other embodiments reversal occurs in alternating step changes. Regardless, the flow reversal enables substantial heat exchange between the incoming gas of one step and the outgoing gas of the alternate step. This results in a reactor that has highest temperatures near the middle of the flow path, and relatively cool temperatures at both ends of the reactor.

In a regenerative pyrolysis system, peak pyrolysis gas temperature is determined as follows. The peak pyrolysis gas temperature typically is experienced by the gases at the beginning of the pyrolysis step, because the solid material is typically at its highest temperature at the beginning of the pyrolysis step. One skilled in the art will appreciate that temperatures immediately proximate to the solid material may be higher, and may, in some infinitesimal layer, actually approach the solid temperature. However, the pyrolysis temperature referred to herein should be considered a bulk gas temperature, which is a temperature that may be measured by a device (such as a thermocouple) that is not in contact with the solid material. For example, if the gas is traveling through channels in a checkerbrick, tile or honeycomb solid material, the bulk gas temperature could be taken as the average temperature over any channel cross-section, and the peak pyrolysis gas temperature as the highest cross-sectional-average temperature of the pyrolysis stream.

Thermal pyrolysis reactors may also be characterized in terms of the residence time of pyrolysis gases in the reactor. Residence time is most generally defined as the time required for some average non-reacting molecule to pass through the pyrolysis reactor or furnace. Residence time may be further defined to be the time spent within the actively heated or cooled portions of the reactor or furnace. This includes time spent within tubulars or heat transfer solids of a furnace or regenerative reactor, respectively, but excludes residence time spent in headers or other means of conveyance to or from the actively heated or cooled regions of the furnace or reactor. Additionally, the high-severity residence time is defined as the time that pyrolysis stream components are exposed to temperatures above the severity threshold. An exact calculation of residence time requires measurements with tracer compounds (such as radioactive additives to the feed) or requires a specific knowledge of the temperature and composition of the pyrolysis stream at all times as it passes through the pyrolysis reactor. For the purposes of the present application, residence time (in either form) may be approximated using interpolation and extrapolation of discreet composition and temperature measurements, and/or using model-based estimations of temperature and composition, as is known in the art.

The one or more embodiments herein may include the conversion of feedstocks into higher value hydrocarbons, such as acetylene, at different temperatures. These temperatures may include high reformation temperature, which in the past has been a significant barrier to commercialization and efficiency. The pyrolysis reactor according to the present techniques is a higher temperature hydrocarbon pyrolysis reactor that operates at higher temperatures than steam cracking reactors used in commercial steam cracking operations. For example, naphtha steam cracking operations typically operate at furnace radiant coil outlet temperatures of ≤about 815° C., which corresponds to the peak pyrolysis gas temperature. However, in the present techniques, the thermal pyrolysis reactor may operate at peak pyrolysis gas temperatures of at least 1200.0° C., at least 1700.0° C., at least 2000.0° C., preferably at least 1400.0° C., at least 1500.0° C., or more preferably at least 1540.0° C. That is, the peak pyrolysis gas temperature ranges may include temperatures between 1200.0° C. and 2200.0° C., between 1450.0° C. and 1700.0° C., between at least 1500.0° C. to 1675.0° C., or between 1540.0° C. to 1650.0° C. In some reactions, it may even be still more preferable to expose the pyrolysis feed to heat using very short residence times, such as ≤0.1 second, to a temperature in excess of 1600.0° C. Pyrolysis reactions that benefit from reaction or conversion of methane that may be a part of the pyrolysis feed, typically involve peak pyrolysis gas temperatures in excess of 1400.0° C. for the methane to react or convert. An exemplary preferred process may pyrolyze the feed stream within the reactor, such as at peak pyrolysis gas temperatures of from 1540.0° C. to 2200.0° C., and more preferably from 1600.0° C. to 1800.0° C. Exemplary residence times preferably may be short, such as ≤0.5 second, ≤0.3 second and preferably ≤about 50 milliseconds or in the range of 0.5 seconds to 0.001 seconds. High severity residence times are preferably ≤0.05 seconds, and more preferably ≤0.02 seconds.

As described earlier, achieving any peak pyrolysis gas temperature involves the existence of a solid temperature that is heated to a higher temperature, and a combustion gas temperature that is a higher temperature than the solid temperature. In one or more embodiments of the present techniques, the maximum temperature of the solid elements in the thermal pyrolysis system (e.g., tubulars for furnaces or heat transfer solids for regenerative systems) is between about 5° C. and about 500° C. higher than the peak pyrolysis gas temperature. In a preferred embodiment, the maximum temperature of the solid elements in the thermal pyrolysis system is between 10° C. and 100° C. higher than the peak pyrolysis gas temperature. Reverse flow regenerative reactors may also include some amount of quenching by means of heat removal to the heat transfer solids. In reverse flow regenerative reactor embodiments of the present techniques, the pyrolysis gas may be cooled to a temperature between 100° C. and 1000° C. by means of heat removal to the heat transfer solids in the reactor, and more preferably cooled to a temperature between 300° C. and 550° C.

In other embodiments, the thermal pyrolysis reactor may be a regenerative reverse flow reactor or regenerative pyrolysis reactor. Regenerative pyrolysis reactors are well suited for processing volatized or volatizable feedstocks that are substantially free of non-volatile components, such as metals, and other residual or nonvolatizable components, which would otherwise lay down, ash, and/or build up in the reactor. Examples of such reactors may be found in U.S. Patent Application Publication Nos. 2007/0144940 and 2008/0142409. These references, which are incorporated by reference, teach a regenerative bed reverse flow reactor wherein the location of the exothermic reaction is controlled. The regenerative reactor bed is regenerated by supplying a first reactant through a first channel to a first regenerative bed and a second reactant through a second channel in the first regenerative bed, combining first and second reactants in a gas mixer, and reacting to produce a heated reaction product which is passed through a second regenerative bed to transfer heat thereto. Other examples may be found in U.S. Patent Application Publication No. 2009/0008292 and 2009/008292; U.S. Pat. No. 7,491,250 U.S. Patent Application Publication No. 2009/008292; and U.S. Patent Application Ser. No. 61/349,464, which are each incorporated by reference. These examples may include U.S. Ser. Nos. 11/643,541; 12/119,762; 12/121,353; and 61/349,464.

Further, the temperature within the pyrolysis reactor may also involve large swings in temperatures. Accordingly, pyrolysis reactors materials have to be designed with withstand these temperature swings. That is, in the proposed configuration, pyrolysis reactors may have components or internals, such as valves, tubes, conductive monoliths, thin-walled honeycombs, bead-beds, mixers, quench media, and other reactor components, regardless of whether simple or complex shaped, that are directly associated with the pyrolysis reaction. These components made of different materials able to withstand these larger temperature swings. As a specific example, a regenerative reverse flow reactor may include different materials for its internal components. Examples of such material are described in U.S. Ser. Nos. 12/099,251; 12/277,056; 12/467,832; 12/772,757; and 12/623,046.

As an example, U.S. Ser. No. 11/643,541 (U.S. Patent Application Publication No. 2007/0191664), which is incorporated by reference, describes a process and high severity regenerative thermal pyrolysis reactor utilized to manufacture acetylene from a methane or hydrocarbon-containing feed. These process steps and/or pyrolysis reactor may be utilized in one or more of the embodiments described above. For instance, the process may include a reactor system that includes (i) a first (quenching) reactor comprising a first end and a second end, and (ii) a second reactor comprising primary end and a secondary end, the first and second reactors oriented in a series relationship with respect to each other such that the secondary end of the second reactor is proximate the second end of the first reactor. The process may include a two-step process wherein heat is (1) added to the reactor media via in-situ combustion step and (2) removed from the reactor media via in-situ endothermic pyrolysis step. The combustion step may involve passing a first and second combustion reactant (combustion feeds) separately but simultaneously through the first (quenching) reactor, by supplying a first reactant through a first channel in the first reactor and supplying at least a second reactant through a second channel in the first reactor, such that the first and second reactants are supplied to the first reactor from the first end of the first reactor. The combustion step may further involve combining the first and second reactants at the second end of the first reactor and reacting the combined reactants to produce a heated reaction product; passing the heated reaction product through the second reactor to transfer at least a portion of the heat from the reaction product to the second reactor, and recovering an exhaust gas from the second reactor. Preferably, the combining is enhanced by a reactant (combustion feed) mixer that mixes the reactants to facilitate substantially complete combustion/reaction at the desired location, with the mixer preferably located between the first and second reactors. Thereafter, the endothermic pyrolysis step, which may be carried out at a pressure between about 5 pounds per square inch absolute (psia) (35 kPa absolute (kPaa)) up to about 45 psia (310 kPaa), supplies methane or other hydrocarbon through the heated second reactor to the first reactor, in flow direction the opposite to that of the heating (combustion) step, to convert at least a portion of the methane into acetylene; passing the supplied methane and the produced acetylene through the first reactor to quench the methane and the produced acetylene; and recovering the produced acetylene. The process may further include supplying hydrogen in the second reactor during the pyrolysis step to moderate the reaction of the methane or other hydrocarbons in the feed. Hydrogen may be used in molar ratio to methane of 0 to 5, preferably of 1 to 3 during the pyrolysis step. In a preferred embodiment, the media in the first reactor includes one or more honeycomb monolith structures that provide flow channels for the first and second reactant. The process may further include media of the first or second reactor that has wetted surface area between 50 and 3000 ft$^{-1}$, heat transfer coefficient $\geq 0.02$ cal/cm$^3$ s ° C., and bulk heat capacity $\geq$about 0.10 cal/cm$^{3}$° C., and may be comprised of honeycomb monoliths having 40 to 80% open frontal area and between about 50 and 2000 channels per square inch. The process may further include compressors, blowers, or fans to supply air as one combustion feed during the combustion step, which may be carried out at a pressure between about 15 psia (103 kPaa) and 45 psia (310 kPaa); may include expansion turbines to recover mechanical energy from higher pressure exhaust gases; and may include recycle of exhaust gases (EGR) to the combustion feed for combination with the air, for example to reduce the oxygen content and the adiabatic flame temperature of the combustion feed. Noncombustible gases, for example $H_2O$, $CO_2$, and $N_2$, may be added to the combustion feed to reduce combustion temperature. The combustion step may comprise a first and second reactant that are a fuel gas and an oxidant that are maintained substantially separated as they pass through the first reactor and which combust or burn when combined. By substantially separated is meant that at least 50%, and more preferably 75% or 90% of the potential combustion that may occur after the axial transit of the first reactor. The process may further include a mixer that is comprised of multiple mixer segments, each preferably having similar cross-sectional area and length and each preferably accepting flow during the combustion step from roughly equal numbers of first and second channels, representing roughly equal proportions of first and second reactant, and having a characteristic L/D between 0.1 and 5.0. Preferably, the mixer has a total volume 20% of the total volume of mixer plus flow regions in first and second reactor, and preferably has a geometric void volume $\leq 20\%$ of the void volume in mixer plus first and second reactor. The process may further include a cycle time that includes the time spent in combustion step plus time spent in pyrolysis step plus any time needed to switch between steps. Typical cycle times may be between 1 and 240 seconds, or between 2 and 60 seconds, and without expectation that combustion and pyrolysis steps have equal durations.

The embodiments of the present techniques may also comprise different embodiments, such as in the following exemplary paragraphs:

1. A hydrocarbon conversion method comprising: exposing a pyrolysis feed under thermal pyrolysis high-severity operating conditions to produce a reactor product comprising hydrogen, ethylene, and X mole % acetylene per mole of reactor product; reacting at least a portion of the reactor product with a catalyst in a converter operated in at least partially in the vapor phase to form a conversion product comprising 0.0 mole % to Z mole % acetylene per mole of the conversion product, the portion of the reactor product comprising Y mole % of acetylene per mole of the portion of the reactor product and the portion of the reactor product having a hydrogen to acetylene molar ratio in the range of from 1.0 and 10.0; and wherein (i) X<90.0% of a first acetylene non-autodecomposition amount, (ii) Y<90.0% of a second acetylene non-autodecomposition amount, and (iii) Y>Z.

2. The method of paragraph 1, comprising separating from the conversion product a converter recycle product comprising ethylene, and combining the converter recycle product with the retained portion of the reactor product upstream of the reacting.

3. The method of paragraph 2, comprising: determining the X mole % acetylene per mole of reactor product; and adjusting the amount of converter recycle product mixed with the retained reactor product to maintain the mixture Y<89.0% of the second acetylene non-autodecomposition amount.

4. The method of paragraph 2 or 3, comprising: determining the retained reactor product's hydrogen content; and adjusting the flow rate of at least one of (i) the converter recycle product based on the X<90.0% of a first acetylene non-autodecomposition amount or (ii) the hydrogen content level in second product.

5. The method of paragraph 1, comprising separating hydrogen from the reactor product upstream of the reacting.

6. The method of paragraph 5, wherein the hydrogen is separated by means of a membrane.

7. The method of paragraph 6, wherein the membrane inlet pressure is between 150 psig (1034 kPag) and 250 psig (1724 kPag).

8. The method of paragraph 5, wherein the hydrogen is separated by means of pressure swing adsorption.

9. The method of paragraph 8, wherein the pressure swing adsorption inlet pressure is in the range of 150 psig (1034 kPag) and 250 psig (1724 kPag).

10. The method of paragraph 5, wherein the hydrogen is separated by means of liquid phase absorption and light gas desorbtion.

11. The method of paragraph 10, wherein the liquid phase absorption and light gas desorbtion is performed at pressures in the range of 50 psig (345 kPag) and 250 psig (1724 kPag).

12. The method of any one of paragraphs 5 to 11, comprising: determining the reactor product's hydrogen content; and adjusting the amount of hydrogen separated from the reactor product to regulate the reactor product's hydrogen content.

13. The method of paragraph 2, comprising compressing the conversion recycle product prior to combining the converter recycle product with the retained portion of the reactor product.

14. The method of any one of paragraphs 1 to 13, wherein the thermal pyrolysis high-severity operating conditions include exposing the pyrolysis feed to pressures of $\geq 36$ psig (248 kPag) in the exposing.

15. The method of any one of paragraphs 1 to 14, further comprising producing the pyrolysis feed by combining at least a portion of the separated hydrogen and a reactor feed, the pyrolysis feed having an atomic hydrogen to carbon (H/C) molar ratio in the range of from 5 to 15 at a location upstream of the exposing.

16. The method of any one of paragraphs 1 to 15, wherein the thermal pyrolysis high-severity operating conditions comprise peak pyrolysis gas temperature $\geq 1450.0°$ C.

17. The method of any one of paragraphs 1 and 16, wherein the reactor product has a $C_+$ to $C_2$ unsaturate weight ratio $\leq 0.5$.

18. The method of any one of paragraphs 1 to 16, wherein the reactor product has a $C_{3+}$ to acetylene weight ratio $\leq 0.45$.

19. The method of any one of paragraphs 1 to 18, further comprising polymerizing at least a portion of the conversion product.

20. The method of any one of paragraphs 5 to 11, further comprising mixing a combustion feed with at least a portion of the separated hydrogen and reacting the combustion feed along with the at least a portion of the separated hydrogen to heat a pyrolysis reactor for the exposing.

21. The method of any one of paragraphs 1 to 20, wherein the thermal pyrolysis high-severity operating conditions comprise peak pyrolysis gas temperature is in the range of $1600.0°$ C. to $1800.0°$ C., and wherein the exposing is for a residence time in the range of 0.5 seconds to 0.001 seconds.

22. The method of any one of paragraphs 1 to 21, wherein the exposing is performed in a regenerative reverse flow pyrolysis reactor and wherein the method further comprises: exothermically reacting a first combustion feed with a second combustion feed to heat a region at least partially within the pyrolysis reactor; removing combustion products from the pyrolysis reactor; and heating the pyrolysis feed using at least a portion of the heat generated by the exothermic reaction.

23. An apparatus for processing hydrocarbons comprising: a hydrogen separation unit configured to separate a reactor product into a hydrogen product and an acetylene rich product; a mixing unit in fluid communication with the hydrogen separation unit and configured to combine the acetylene rich product with a conversion recycle product to form a mixture; and a converter in fluid communication with the mixing unit and configured to react the mixture with a catalyst to form a conversion product comprising olefins.

24. The apparatus of paragraph 23, comprising a thermal pyrolysis reactor in fluid communication with the hydrogen separation unit and configured to expose a pyrolysis feed to a peak pyrolysis gas temperature $\geq 1540.0°$ C. within the thermal pyrolysis reactor to produce a reactor product comprising ethylene and acetylene.

25. The apparatus of any one of paragraphs 23 to 24, comprising a polymerization unit in fluid communication with the converter and configured to convert at least a portion of the conversion product into polyethylene.

26. The apparatus of any one of paragraphs 23 to 25, comprising a splitter in fluid communication with the converter and the mixing unit and configured to separate the conversion recycle product from the conversion product.

27. The apparatus of paragraph 23, comprising a compressor in fluid communication with the mixing unit and the splitter, the compressor being configured to compress at least a portion of the conversion recycle product.

28. The apparatus of any one of paragraphs 23 to 25, comprising an ethylene source in fluid communication with the mixer, the ethylene source being configured to provide the conversion recycle product.

29. The apparatus of any one of paragraphs 23 to 28, wherein the hydrogen separation unit comprises a hydrogen membrane.

30. The apparatus of any one of paragraphs 23 to 28, wherein the hydrogen separation unit comprises a pressure swing adsorption unit.

31. The apparatus of any one of paragraphs 24 to 30, comprising one or more lines providing fluid communication between the hydrogen separation unit and the thermal pyrolysis reactor, at least one of the lines being configured to add a portion of the hydrogen product to a combustion feed being provided to the thermal pyrolysis reactor, wherein the thermal pyrolysis reactor is configured to react the portion of the hydrogen product and the combustion feed to heat the thermal pyrolysis reactor.

32. The apparatus of any one of paragraphs 24 to 30, comprising one or more lines providing fluid communication between the hydrogen separation unit and the thermal pyrolysis reactor, at least one of the lines being configured to combine a portion of the hydrogen product with a reactor feed to form the pyrolysis feed prior to the thermal pyrolysis unit.

33. The apparatus of any one of paragraphs 24 to 30, comprising one or more lines providing fluid communication between the hydrogen separation unit and the thermal pyrolysis reactor, at least one of the lines being configured to add a first portion of the hydrogen product to a combustion feed being provided to the thermal pyrolysis reactor and comprising one or more lines providing fluid communication between the hydrogen separation unit and the thermal pyrolysis reactor and configured to add a second portion of the hydrogen product to a reactor feed to form the pyrolysis feed prior to the thermal pyrolysis unit.

34. The apparatus of any one of paragraphs 23 to 33, wherein the thermal pyrolysis reactor is a regenerative reverse flow reactor that comprises: a reactor body, wherein the reactor body forms a reaction region within the reactor body; a packing material disposed at least partially within the reaction region; and one or more valve assemblies coupled to the reactor body and in flow communication with the reaction region and configured to control fluid flow of the at least a portion of the pyrolysis feed between a location external to the reactor body and within the reaction region.

35. The apparatus of any one of paragraphs 24 to 34, comprising: an acetylene measurement device configured to measure the acetylene volume percent of the acetylene rich product; and a mixing flow rate unit configured to adjust the amount of converter recycle product mixed with the acetylene rich product to maintain the mixture at an acetylene non-autodecomposition amount.

36. The apparatus of paragraph 35, comprising a process control unit in communication with the mixing flow rate unit and the acetylene measurement device, the control device being configured to determine the acetylene volume percent of the acetylene rich product and provide an indication to the mixing flow rate unit to adjust the amount of converter recycle product mixed with the acetylene rich product.

37. The apparatus of any one of paragraphs 24 to 36, comprising: a hydrogen content measurement device configured to measure the hydrogen content of the reactor product; and a hydrogen separation control unit configured to adjust the amount of hydrogen product removed from the at least a portion of the reactor product in the hydrogen separation unit.

38. The apparatus of paragraph 37, comprising a process control unit in communication with the hydrogen content measurement device and the hydrogen separation control unit, the process control unit being configured to determine the hydrogen content of the reactor product and provide an indication to the hydrogen separation control unit to adjust the amount of hydrogen product separated from the reactor product.

While the present invention has been described and illustrated with respect to certain embodiments, it is to be understood that the invention is not limited to the particulars disclosed and extends to all equivalents within the scope of the claims.

The invention claimed is:

1. A hydrocarbon conversion method comprising:
exposing a pyrolysis feed under thermal pyrolysis high-severity operating conditions in a regenerative pyrolysis reactor to produce a reactor product comprising hydrogen, ethylene, and X mole % acetylene per mole of reactor product, wherein the thermal pyrolysis high-severity operating conditions include (i) a Gaussian-like temperature profile, and (ii) a severity threshold temperature, (iii) a residence time in the range of from 0.5 seconds to 0.001 seconds, and (iv) a peak pyrolysis gas temperature that is greater than the severity threshold temperature;
reacting at least a portion of the reactor product with a catalyst in a converter operated in at least partially in the vapor phase to form a conversion product comprising 0.0 mole % to Z mole % acetylene per mole of the conversion product, the at least a portion of the reactor product comprising Y mole % of acetylene per mole of the at least a portion of the reactor product and the at least a portion of the reactor product having a hydrogen to acetylene molar ratio in the range of from 1.0 and 10.0; and
wherein (i) X<90.0% of a first acetylene non-autodecomposition amount, (ii) Y<90.0% of a second acetylene non-autodecomposition amount, and (iii) Y>Z.

2. The method of claim 1, further comprising separating from the conversion product a converter recycle product comprising ethylene, and combining the converter recycle product with the at least a portion of the reactor product upstream of the reacting.

3. The method of claim 2, comprising: determining the X mole % acetylene per mole of reactor product; and adjusting the amount of converter recycle product mixed with the at least a portion of the reactor product to maintain the mixture Y<89.0% of the second acetylene non-autodecomposition amount.

4. The method of claim 2, further comprising:
determining the hydrogen content of the at least a portion of the reactor product; and adjusting the flow rate of at least one of
  (i) the converter recycle product, based on the X≤90.0% of a first acetylene non-autodecomposition amount, or
  (ii) the hydrogen to or from the at least a portion of the reactor product.

5. The method of claim 1, further comprising separating hydrogen from the reactor product upstream of the reacting.

6. The method of claim 5, wherein the hydrogen is separated by means of a membrane.

7. The method of claim 5, further comprising: determining the hydrogen content of the reactor product; and adjusting the amount of hydrogen separated from the reactor product to regulate the hydrogen content of the reactor product.

8. The method of claim 2, further comprising compressing the converter recycle product prior to combining the converter recycle product with the at least a portion of the reactor product.

9. The method of claim 1, wherein the peak pyrolysis gas temperature is ≥1450.0° C.

10. The method of claim 1, wherein the reactor product has a $C_{3+}$ to $C_2$ unsaturate weight ratio ≤0.5.

11. The method claim 1, further comprising polymerizing at least a portion of the conversion product.

* * * * *